(12) United States Patent
Ellard et al.

(10) Patent No.: US 9,079,914 B2
(45) Date of Patent: Jul. 14, 2015

(54) FUSED AMINODIHYDRO-OXAZINE DERIVATIVES

(75) Inventors: John Mark Ellard, Hatfield (GB); Christopher Neil Farthing, Hatfield (GB); Adrian Hall, Hatfield (GB)

(73) Assignee: Eisai R&D Management Co., Ltd., Tokyo (JP)

( * ) Notice: Subject to any disclaimer, the term of this patent is extended or adjusted under 35 U.S.C. 154(b) by 349 days.

(21) Appl. No.: 13/386,092

(22) PCT Filed: Jul. 21, 2010

(86) PCT No.: PCT/EP2010/060587
§ 371 (c)(1),
(2), (4) Date: Apr. 27, 2012

(87) PCT Pub. No.: WO2011/009898
PCT Pub. Date: Jan. 27, 2011

(65) Prior Publication Data
US 2012/0202804 A1 Aug. 9, 2012

(30) Foreign Application Priority Data
Jul. 22, 2009 (GB) .................................. 0912778.8

(51) Int. Cl.
*C07D 498/04* (2006.01)
*A61K 31/5365* (2006.01)
(52) U.S. Cl.
CPC .................................. *C07D 498/04* (2013.01)
USPC ........................................ 514/230.5; 544/91
(58) Field of Classification Search
CPC ........................... C07D 498/04; A61K 31/5365
USPC ............................................ 544/91; 514/230.5
See application file for complete search history.

(56) References Cited

U.S. PATENT DOCUMENTS

| | | | |
|---|---|---|---|
| 3,227,713 A | 1/1966 | Behner et al. | |
| 3,235,551 A | 2/1966 | Schubert et al. | |
| 7,189,715 B2 | 3/2007 | Jerussi et al. | |
| 7,648,983 B2 | 1/2010 | Audia et al. | |
| 8,158,620 B2 | 4/2012 | Suzuki et al. | |
| 8,198,269 B2 | 6/2012 | Motoki et al. | |
| 8,338,407 B2 | 12/2012 | Hall et al. | |
| 8,426,584 B2 | 4/2013 | Mitasev et al. | |
| 8,501,733 B2 | 8/2013 | Motoki et al. | |
| 2004/0110743 A1 | 6/2004 | Miyamato et al. | |
| 2006/0052406 A1 | 3/2006 | Fisher et al. | |
| 2006/0111370 A1 | 5/2006 | Zhu et al. | |
| 2007/0021454 A1 | 1/2007 | Coburn et al. | |
| 2007/0287692 A1 | 12/2007 | Wu et al. | |
| 2008/0139538 A1 | 6/2008 | McGaughey et al. | |
| 2008/0200445 A1 | 8/2008 | Zhu et al. | |
| 2009/0082560 A1 | 3/2009 | Kobayashi et al. | |
| 2009/0209755 A1 | 8/2009 | Suzuki et al. | |
| 2010/0075957 A1 | 3/2010 | Tamura et al. | |
| 2010/0093999 A1 | 4/2010 | Motoki et al. | |
| 2010/0160290 A1 | 6/2010 | Kobayashi et al. | |
| 2010/0317850 A1 | 12/2010 | Suzuki et al. | |
| 2011/0009395 A1 | 1/2011 | Audia et al. | |
| 2011/0152253 A1 | 6/2011 | Motoki et al. | |
| 2011/0207723 A1 | 8/2011 | Motoki et al. | |
| 2012/0094984 A1 | 4/2012 | Suzuki et al. | |
| 2012/0190672 A1 | 7/2012 | Hall et al. | |
| 2012/0190848 A1 | 7/2012 | Mitasev et al. | |

(Continued)

FOREIGN PATENT DOCUMENTS

| EP | 1 942 105 | 7/2008 |
|---|---|---|
| EP | 2 233 474 | 9/2010 |

(Continued)

OTHER PUBLICATIONS

Abdel-Magid et al., "Reductive Amination of Aldehydes and Ketones with Sodium Triacetoxyborohydride. Studies on Direct and Indirect Reductive Amination Procedures," *J. Org. Chem.*, 61(11):3849-3862 (1996).

(Continued)

*Primary Examiner* — Kahsay Habte
(74) *Attorney, Agent, or Firm* — Fish & Richardson P.C.

(57) ABSTRACT

A compound represented by the general formula:

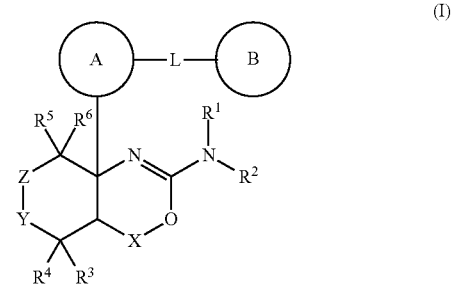

or a pharmaceutically acceptable salt thereof or a solvate thereof, wherein Ring A is a $C_{6-14}$ aryl group or the like, L is —$NR^eCO$— or the like (wherein $R^e$ is a hydrogen atom or the like), Ring B is a $C_{6-14}$ aryl group or the like, X is a $C_{1-3}$ alkylene group or the like, Y is a single bond or the like, Z is a $C_{1-3}$ alkylene group or the like, $R^1$ and $R^2$ are each independently a hydrogen atom or the like, and $R^3$, $R^4$, $R^5$ and $R^6$ are independently a hydrogen atom, a halogen atom or the like, has an Aβ production inhibitory effect or a BACE1 inhibitory effect and is useful as a prophylactic or therapeutic agent for a neurodegenerative disease caused by Aβ and typified by Alzheimer-type dementia.

28 Claims, No Drawings

(56) References Cited

U.S. PATENT DOCUMENTS

| | | |
|---|---|---|
| 2012/0202828 A1 | 8/2012 | Castro Pineiro et al. |
| 2013/0197244 A1 | 8/2013 | Mitasev et al. |
| 2013/0203740 A1 | 8/2013 | Hall et al. |

FOREIGN PATENT DOCUMENTS

| | | |
|---|---|---|
| JP | 09-067355 | 3/1997 |
| JP | 2004-149429 | 5/2004 |
| WO | WO 01/87293 | 11/2001 |
| WO | WO 02/096897 | 12/2002 |
| WO | WO 2004/014843 | 2/2004 |
| WO | WO 2004/043916 | 5/2004 |
| WO | WO 2005/058311 | 6/2005 |
| WO | WO 2005/097767 | 10/2005 |
| WO | WO 2006/041404 | 4/2006 |
| WO | WO 2006/041405 | 4/2006 |
| WO | WO 2006/059234 | 6/2006 |
| WO | WO 2006/138264 | 12/2006 |
| WO | WO 2007/011810 | 1/2007 |
| WO | WO 2007/049532 | 5/2007 |
| WO | WO 2007/114771 | 10/2007 |
| WO | WO 2007/139230 | 12/2007 |
| WO | WO 2008/073365 | 6/2008 |
| WO | WO 2008/133273 | 11/2008 |
| WO | WO 2008/133274 | 11/2008 |
| WO | WO 2009/067081 | 5/2009 |
| WO | WO 2009/091016 | 7/2009 |
| WO | WO 2010/013302 | 2/2010 |
| WO | WO 2010/013794 | 2/2010 |
| WO | WO 2010/038686 | 4/2010 |
| WO | WO 2011/005738 | 1/2011 |
| WO | WO 2011/009897 | 1/2011 |
| WO | WO 2011/009898 | 1/2011 |
| WO | WO 2012/003274 | 1/2012 |
| WO | WO 2012/093148 | 7/2012 |
| WO | WO 2012/098461 | 7/2012 |
| WO | WO 2012/100179 | 7/2012 |

OTHER PUBLICATIONS

Ames et al., "Methods for detecting carcinogens and mutagens with the *Salmonella*/mammalian-microsome mutagenicity test," *Mutat. Res.*, 31:347-364 (1975).

Aranyos et al., "Novel Electron-Rich Bulky Phosphine Ligands Facilitate the Palladium-Catalyzed Preparation of Diaryl Ethers," *J Am Chem Soc.*, 121(18):4369-4378 (1999).

Arnone et al., An Enantiospecific Entry to Fluoro Substituted Aminocyclopentanols through Intramolecular Nitrile Oxide, Nitrone, and Oxime Cycloaddition Reactions, *Tetrahedron: Asymmetry* 5(6):1019-1028 (1994).

Aschwanden et al., "Reduction of 2,3-dihydroisoxazoles to beta-amino ketones and beta-amino alcohols," *Org. Lett.*, 7(25):5741-5742 (2005).

Barange et al., "A Remarkable Accelerating Effect of Ag-Salt on Intramolecular Cyclization of o-(1-Alkynyl)benzenesulfonamides," *J. Org. Chem.*, 72(22):8547-8550 (2007).

Barlow et al., "Intervalence Transitions in the Mixed-Valence Monocations of Bis(triarylamines) Linked with Vinylene and Phenylene—Vinylene Bridges," *J. Am. Chem. Soc.*, 127(48):16900-16911 (2005).

Berge et al., "Pharmaceutical salts," *J. Pharm. Sci.*, 66:1-19 (1977).

Bobrov et al., "Interaction of Quinone Oxide with Thiourea" *Chemistry and Chemical Technology*, 33(10):15-18 (1990) (original and English language translation).

Brzostwska et al., "Chiral Prodyes: Synthesis and Full Characterization of (S)-1-Phenylethylamides of the Optically Active Q-Methyldihydrofluoresceins," *Heterocycles*, 32(10):1968-1972 (1991).

Butler et al., "A Facile Synthesis of New 5H-Indazolo[3,2-b]benzo[d]-1,3-oxazines via One-Pot Intramolecular Bis-heterocyclizations," *J. Org. Chem.*, 73(1):234-240 (2008).

Chakrabarty et al., "DBU, a highly efficient reagent for the facile regeneration of (hetero)arylamines from their acetamides and benzamides: influence of solvent, temperature, and microwave irradiation," *Synth. Commun.*, 32(2):265-272 (2002).

Coates et al., "Annelative ring expansion via intramolecular [2+2] photocycloaddition of .alpha.,.beta.-unsaturated .gamma.-lactones and reductive cleavage: synthesis of hydrocyclopentacyclooctene-5-carboxylates," *J. Org. Chem.*, 47(19):3597-3607 (1982).

Cohen et al., "Synthesis of 2-Amino-5,6-dihydro-4H-1,3-thiazines and Related Compounds by Acid Catalyzed Cyclization of Allylic Isothiuronium Salts," *Journal of Heterocyclic Chemistry*, 14:717-723 (1977).

Crisp and Meyer, "Palladium-catalyzed, carbonylative, intramolecular coupling of hydroxyvinyl triflates. Synthesis of substituted .alpha.,.beta.-butenolides," *J. Org. Chem.*, 57(25):6972-6975 (1992).

Cross et al., International Union of Pure and Applied Chemistry (IUPAC) Rules for the Nomenclature of Organic Chemistry, Section E, Stereochemistry, *Pure & Applied Chemistry*, 45:11-30 (1976).

Danheiser et al., "An annulation method for the synthesis of highly substituted polycyclic aromatic and heteroaromatic compounds," *J. Am. Chem. Soc.*, 112(8):3093-3100 (1990).

De Lucca et al., "Discovery and Structure—Activity Relationship of N-(Ureidoalkyl)-Benzyl-Piperidines As Potent Small Molecule CC Chemokine Receptor-3 (CCR3) Antagonists," *J. Med. Chem.*, 45(17)3794-3804 (2002).

Edwards et al., "Application of Fragment-Based Lead Generation to the Discovery of Novel, Cyclic Amidine β-Secretase Inhibitors with Nanomolar Potency, Cellular Activity, and High Ligand Efficiency," *J. Med. Chem.*, 50(24):5912-5925 (2007).

Fang et al., "Synthesis, Antibacterial, and Cytotoxic Evaluation of Certain 7-Substituted Norfloxacin Derivatives," *J. Med. Chem.*, 43(20):3809-3812 (2000).

Forman et al., "Differential Effects of the Swedish Mutant Amyloid Precursor Protein on β-Amyloid Accumulation and Secretion in Neurons and Nonneuronal Cells," *The Journal of Biological Chemistry*, 272(51):32247-32253 (1997).

Fuller et al., "Succinct Synthesis of β-Amino Acids via Chiral Isoxazolin," *J. Am. Chem. Soc.*, 127(15):5376-5383 (2005).

Fuller et al., "Synthesis and Structural Characteristics of Geminally Disubstituted β-Amino Acids," *SYNLETT.*, 8:1409-1413 (2004).

Fulop et al., "Synthesis of Stereoisomers 2-Phenylimino-3,1-Perhydro-Benzoxazines and 3, 1-Perhydrobenzothiazines," *Org Prep Proced Int'l*, 20:73-82 (1988).

Glenner et al., "Alzheimer's Disease: Initial report of the purification and characterization of a novel cerebrovascular amyloid protein," *Biochemical and Biophysical Research Communications*, 120(3):885-890 (1984).

Gloor et al., "Molecular and cellular permeability control at the blood-brain barrier," *Brain Res. Rev.*, 36:258-264 (2001).

Gong et al., "Alzheimer's disease-affected brain: Presence of oligomeric Aβ ligands (ADDLs) suggests a molecular basis for reversible memory loss," *Proceeding National Academy of Science USA*, 100(18):10417-10422 (2003).

Gouras et al., "Intraneuronal Aβ42 Accumulation in Human Brain," *American Journal of Pathology*, 156(1):15-20 (2000).

Green et al., "Mutagen testing using TRP+ reversion in *Escherichia coli*," *Mutat. Res.*, 38:3-32 (1976).

Greene and Wuts, "Protective Groups in Organic Chemistry, Second Edition", *John Wiley & Sons* p. 327-330 (1991).

Greene and Wuts, "Protective Groups in Organic Chemistry, Third Edition", *John Wiley & Sons*, p. 17-245 (1999).

Greene and Wuts, "Protective Groups in Organic Chemistry, Third Edition", *John Wiley & Sons*, p. 506-507 (1999).

Greene and Wuts, "Protective Groups in Organic Chemistry, Third Edition", *John Wiley & Sons*, P. 293-329 (1999).

Greene and Wuts, "Protective Groups in Organic Chemistry, Third Edition", *John Wiley & Sons*, p. 494-572 (1999).

Greene and Wuts, "Protective Groups in Organic Chemistry, Third Edition", *John Wiley & Sons*, p. 642-643 (1999).

Greene and Wuts, "Protective Groups in Organic Chemistry, Third Edition", *John Wiley & Sons*, p. 531-537 (1999).

Greene et al., "Protective Groups in Organic Chemistry, Third Edition," *John Wiley & Sons*, 404-408 (1999).

(56) References Cited

OTHER PUBLICATIONS

Greene et al., "Protective Groups in Organic Chemistry, Third Edition," *John Wiley & Sons*, 518-525 (1999).
Gu et al., "Facile One-Pot Synthesis of 6-Monosubstituted and 6,12-Disubstituted 5,11-Dihydroindolo[3,2-b]carbazoles and Preparation of Various Functionalized Derivatives," *J. Org. Chem.*, 72(19):7207-7213 (2007).
Hall et al., "Comparative pharmacokinetic-pharmacodynamic responses in rat and cynomolgus monkey for a novel BACE inhibitor ER-901356," 11th *Int'l Conf on Alzheimer's & Parkinson's Diseases (AD/PD 2013)*, 4 pages, (Mar. 6-10, 2013).
Han et al., "Diverse Synthesis of Novel Bisterpyridines via Suzuki-Type Cross-Coupling," *Org. Lett.*, 9(4):559-562 (2007).
Hassner et al. "Stereochemistry. 82. Conformation of fused five-membered heterocyclic rings derived from the intramolecular oxime olefin cycloaddition reaction," *J. Org. Chem.*, 58(17):4539-4546 (1993).
Hassner, "Interamolecular Oxime Olefin Cycloadditions. Stereospecific Formation of Functionalized Pyrrolidines," *Tetrahedron Letters*, 29 (41):5313-5316 (1988).
He et al., "Utility of unbound plasma drug levels and P-glycoprotein transport data in prediction of central nervous system exposure," *Xenobiotica*, 39:687-693 (2009).
Heany et al., "The influence of oxime stereochemistry in the generation of nitrones from omega-alkenyloximes by cyclization or 1,2-prototropy," *J. Chem. Soc., Perkin Trans.*, 1:341-349 (Jan. 1 , 1998).
Hitchcock et al., "Structure-brain exposure relationships," *J. Med. Chem.*, 49:7559-7583 (2006).
Hock et al., "Antibodies against β-Amyloid Slow Cognitive Decline in Alzheimer's Disease," *Neuron*, 38:547-554 (2003).
Howbert et al., "Novel agents effective against solid tumors: the diarylsulfonylureas. Synthesis, activities, and analysis of quantitative structure-activity relationships," *J. Med. Chem.*, 33:2393-2407 (1990).
Hussain et al., "Oral administration of a potent and selective non-peptidic BACE-1 inhibitor decreases beta-cleavage of amyloid precursor protein and amyloid-beta production in vivo," *J. Neurochem.*, 100:802-809 (2007).
Iserloh et al., "Discovery of an orally efficaceous 4-phenoxypyrrolidine-based BACE-1 inhibitor," *Bioorg. Med. Chem. Lett.*, 18:418-422 (2008).
Ishikawa et al., "Synthesis of A-Ring Fragments of 1α,25-Dihydroxyvitamin D3 and Taxane Diterpenoids: Effective Construction of Conjugated Formylcyclohexene Frameworks from Isoxazolines," *Tetrahedron*, 54(22):5868-5882 (1998).
Iwata et al., "Radiosynthesis of O-[$^{11}$C]methyl-L-tyrosine and O-[$^{18}$F]Fluoromethyl-L-tyrosine as potential PET tracers for imaging amino acid transport," *J Labelled Compounds & Radiopharmaceuticals*, 46(6):555-566 (2003).
Jarrett et al., "The Carboxy Terminus of the β Amyloid Protein is Critical for the Seeding of Amyloid Formation: Implications for the Pathogenesis of Alzheimer's Disease," *Biochemistry*, 32(18):4693-4697 (1993).
Ji et al., "Synthesis and Structure—Activity Relationship Studies of 3,6-Diazabicyclo[3.2.0]heptanes as Novel α4β2 Nicotinic Acetylcholine Receptor Selective Agonists," *J Med. Chem.*, 50(22):5493-5508 (2007).
Kalvass et al., "Influence of nonspecific brain and plasma binding on CNS exposure: implications for rational drug discovery," *Biopharm. Drug Dispos.*, 23:327-338 (2002).
Katagiri et al., "Synthesis of Chiral Spiro 3-Oxazolin-5-one 3-Oxides (Chiral Nitrones) via a Nitrosoketene Intermediate and Their Asymmetric 1,3-Dipolar Cycloaddition Reactions Leading to the EPC Synthesis of Modified Amino Acids," *Tetrahedron*, 53(16):5725-5746 (1997).
Kearney et al., "Solid-Phase Synthesis of 2-Aminothiazoles," *J. Org. Chem.*, 63(1):196-200 (1998).
Khimiya i Khimicheskaya Tekhologiya, 33(10):15-18 (1990).
Knauer and Kunz, "Palladium-catalysed C—C coupling reactions in the enantioselective synthesis of 2,4-disubstituted 4,5-dehydropiperidines using galactosylamine as a stereodifferentiating auxiliary," *Tetrahedron: Asymmetry*, 16(2):529-539 (2005).
Kuo et al., "A Synthesis of Estrone via Novel Intermediates, Mechanism of the Coupling Reaction of a Vinyl Carbinol with a β Diketone," *Journal of Organic Chemistry*, 33(8):3126-3132 (1968).
Kusuhara et al., "Efflux transport systems for drugs at the blood-brain barrier and blood-cerebrospinal fluid barrier (Part 1)," *Drug Discov. Today*, 6:150-156 (2001).
Kwong et al., "Copper-Catalyzed Coupling of Alkylamines and Aryl Iodides: An Efficient System Even in an Air Atmosphere," *Org. Lett.*, 4(4):581-584 (2002).
Leroux et al., "Trifluoromethoxy Substituted Anilines: Metalation as the Key Step for Structural Elaboration," *J. Org. Chem.*, 68(12):4693-4699 (2003).
Lin et al., "Role of P-glycoprotein in pharmacokinetics: clinical implications," *Clin. Pharmacokinet.*, 42:59-98 (2003).
Lin, "How significant is the role of P-glycoprotein in drug absorption and brain uptake?," *Drugs of Today*, 40:5-22 (2004).
Littke et al., "Versatile Catalysts for the Suzuki Cross-Coupling of Arylboronic Acids with Aryl and Vinyl Halides and Triflates under Mild Conditions," *J. Am. Chem. Soc.*, 122(17):4020-4028 (2000).
Liu et al., "A practical and chemoselective reduction of nitroarenes to anilines using activated iron," *Adv. Synth. Caral.*, 347:217-219 (2005).
Mahar et al., "Passive permeability and P-glycoprotein-mediated efflux differentiate central nervous system (CNS) and non-CNS marketed drugs," *J. Pharmacol. Exp. Ther.*, 303:1029-1037 (2002).
Malamas et al., "Design and synthesis of aminohydantoins as potent and selective human β-secretase (BACE1) inhibitors with enhanced brain permeability," *Bioorg. Med. Chem. Lett.*, 20:6597-6605 (2010).
Masters et al., "Amyloid plaque core protein in Alzheimer disease and Down syndrome," *Proceeding National Academy of Science USA*, 82:4245-4249 (1985).
Matassa et al., "Synthesis and in vitro LTD4 antagonist activity of bicyclic and monocyclic cyclopentylurethane and cyclopentylacetamide N-arylsulfonyl amides," *J. Med. Chem.*, 33(9):2621-2629 (1990).
Maurer, "Relationship between exposure and nonspecific binding of thirty-three central nervous system drugs in mice," *Drug Metab. Dispos.*, 33:175-181 (2005).
McCann et al., "Detection of carcinogens as mutagens in the Salmonella/microsome test: assay of 300 chemicals," *Proc. Natl. Acad. Sci. USA.*, 72:5135-5139 (1975).
McCann et al., "Detection of carcinogens as mutagens in the Salmonella/microsome test: assay of 300 chemicals: discussion," *Proc. Natl. Acad. Sci. USA*, 73:950-954 (1976).
Meredith et al., "P-Glycoprotein Efflux and Other Factors Limit Brain Amyloid β Reduction by β-Site Amyloid Precursor Protein-Cleaving Enzyme 1 Inhibitors in Mice," *J. Pharmacol. Exp. Ther*, 326(2):502-513 (2008).
Nahm et al., N-Methoxy-N-Methylamides as Effective Acylating Agents, *Tetrahedron Lett.*, 22(39):3815-3818 (1981).
Nerdinger et al., "Combined Directed ortho Metalation/Suzuki—Miyaura Cross-Coupling Strategies. Regiospecific Synthesis of Chlorodihydroxybiphenyls and Polychlorinated Biphenyls," *J. Org. Chem.*, 72(16):5960-5967 (2007).
Nussbaumer et al., "Highly selective TFAA-cleavage of tertiary 2,4-dimethoxybenzylamines and its use in the synthesis of secondary amines," *Tetrahedron*, 47(26):4591-4602 (1991).
Prakash et al., "Perfluoroalkylation with Organosilicon Reagents," *Chem. Rev.*, 97:757-786 (1997).
Quach and Batey, "Ligand- and Base-Free Copper(II)-Catalyzed C—N Bond Formation: Cross-Coupling Reactions of Organoboron Compounds with Aliphatic Amines and Anilines," *Org. Lett.*, 5(23):4397-4400 (2003).
Rao et al., "Improved Synthesis of Mirtazapine," *Org. Prep. Proced. Int.*, 39(4):399-402 (2007).
Rolandsgard et al., "Stereoselective preparation of spirane bridged, sandwiched bisarenes," *Tetrahedron*, 61(16):4128-4140 (2005).
Romero et al., "Discovery, synthesis, and bioactivity of bis(heteroaryl)piperazines. 1. A novel class of non-nucleoside HIV-1 reverse transcriptase inhibitors," *J. Med. Chem.*, 37(7):998-1014 (1994).

(56) References Cited

OTHER PUBLICATIONS

Rosowsky et al., "Synthesis and biological activity of the 2-desamino and 2-desamino-2-methyl analogues of aminopterin and methotrexate," *J. Med. Chem.*, 34(1):227-234 (1991).

Sankaranarayanan et al., "First demonstration of cerebrospinal fluid and plasma A beta lowering with oral administration of a beta-site amyloid precursor protein-cleaving enzyme 1 inhibitor in nonhuman primates," *J. Pharmacol. Exp. Ther.*, 328:131-140 (2009).

Sankaranarayanan et al., "In Vivo β-Secretase 1 Inhibition Leads to Brain Aβ Lowering and Increased α-Secretase Processing of Amyloid Precursor Protein without Effect on Neuregulin-1," *J. Pharmacol. Exp. Ther*, 324(3):957-969 (2008).

Sapountzis et al., "Synthesis of Functionalized Nitroarylmagnesium Halides via an Iodine—Magnesium Exchange," *J. Org. Chem.*, 70(7):2445-2454 (2005).

Scheuner et al., "Secreted amyloid β-protein similar to that in the senile plaques of Alzheimer's disease is increased in vivo by the presenilin 1 and 2 and APP mutations linked to familial Alzheimer's disease," *Nature Medicine*, 2(8):864-870 (1996).

Schinkel, "P-Glycoprotein, a gatekeeper in the blood-brain barrier," *Adv. Drug Deliv. Rev.*, 36:179-194 (1999).

Schwizer et al., "Antagonists of the myelin-associated glycoprotein: A new class of tetrasaccharide mimics," *Bioorg. Med. Chem.*, 14:4944-4957 (2006).

Selles and Mueller, "Expedient Synthesis of Highly Substituted Fused Heterocoumarins," *Org. Lett.*, 6(2):277-279 (2004).

Shao et al., "4-(2-Pyridyl)piperazine-1-benzimidazoles as potent TRPV1 antagonists," *Bioorg. Med. Chem. Lett.*, 15(3):719-723 (2005).

Shing et al., "Intramolecular nitrile oxide-alkene cycloaddition of sugar derivatives with unmasked hydroxyl group(s)," *Org. Lett.*, 9(5):753-756 (2007).

Summerfield et al., "Central nervous system drug disposition: the relationship between in situ brain permeability and brain free fraction," *J. Pharmacol. Exp. Ther.*, 322:205-213 (2007).

Tamayo et al., Design and synthesis of potent pyridazine inhibitors of p38 MAP kinase, *Bioorg. Med. Chem. Lett.*, 15(9):2409-2413 (2005).

Tao et al., "Copper-catalyzed synthesis of aryl azides and 1-aryl-1,2,3-triazoles from boronic acids," *Tetrahedron Lett.*, 48:3525-3529 (2007).

Trainor, "The importance of plasma protein binding in drug discovery," *Expert Opin. Drug Discov.*, 2:51-64 (2007).

Tzschucke et al., "Arenes to Anilines and Aryl Ethers by Sequential Iridium-Catalyzed Borylation and Copper-Catalyzed Coupling," *Org. Lett.*, 9(5):761-764 (2007).

Tzvetkov et al., Synthesis and photoinitiated radical cyclization of allyl- and propynyloxymethyl substituted cyclopentanones to tetrahydrocyclopenta[c]furanols, *Tetrahedron Lett.*, 46(45):7751-7755 (2005).

Ueno, "Molecular anatomy of the brain endothelial barrier: an overview of the distributional features," *Curr. Med. Chem.*, 14:1199-1206 (2007).

Uno et al., "Reaction of 2-Isoxazolines with Organolithiums in the Presence of Boron Trifluoride," *Bull. Chem. Soc. Jpn.*, 66:2730-2737 (1993).

Vedejs et al., "Enantiocontrolled Synthesis of (1S,2S)-6-Desmethyl-(methylaziridino)mitosene," *J. Am. Chem. Soc.*, 122(22):5401-5402 (2000).

Vedejs et al., "Synthetic Enantiopure Aziridinomitosenes: Preparation, Reactivity, and DNA Alkylation Studies," *J. Am. Chem. Soc.*, 125(51):15796-15806 (2003).

Watanabe et al., "A convenient method for the synthesis of $\Delta$1,6-bicyclo[4.n.0]alken-2-ones," *Tetrahedron Lett.*, 40(46):8133-8136 (1999).

Whisler et al., "Synthetic applications of lithiated N-Boc allylic amines as asymmetric homoenolate equivalents," *J. Org. Chem.*, 68:1207-1215 (2003).

International Search Report and Written Opinion in International Application No. PCT/EP2010/060587, mailed Sep. 27, 2010, 8 pages.

FUSED AMINODIHYDRO-OXAZINE DERIVATIVES

FIELD OF THE INVENTION

The present invention relates to a fused aminodihydro-oxazine derivative and pharmaceutical use thereof. More particularly, the present invention relates to a fused aminodihydro-oxazine derivative which has an amyloid-β (hereinafter referred to as Aβ) protein production inhibitory effect or a beta-site amyloid-β precursor protein cleavage enzyme 1 (hereinafter referred to as BACE1 or beta-secretase) inhibitory effect and is effective for treating a neurodegenerative disease caused by Aβ protein, in particular, Alzheimer-type dementia, Down's syndrome or the like, and to a pharmaceutical composition comprising the fused aminodihydro-oxaazine derivative as an active ingredient.

DESCRIPTION OF RELATED ART

Alzheimer's disease is a disease characterized by degeneration and loss of neurons as well as formation of senile plaques and neurofibrillary degeneration. Currently, Alzheimer's disease is treated only with symptomatic treatment using a symptom improving agent typified by an acetylcholinesterase inhibitor, and a fundamental remedy to inhibit progression of the disease has not yet been developed. It is necessary to develop a method for controlling the cause of the onset of pathology in order to create a fundamental remedy for Alzheimer's disease.

It is assumed that Aβ-proteins as metabolites of amyloid precursor proteins (hereinafter referred to as APP) are highly involved in degeneration and loss of neurons and onset of symptoms of dementia. Aβ-proteins have, as main components, Aβ40 consisting of 40 amino acids and Aβ42 with two amino acids added at the C-terminal. The Aβ40 and Aβ42 are known to have high aggregability and to be main components of senile plaques. Further, it is known that the Aβ40 and Aβ42 are increased by mutation in APP and presenilin genes which is observed in familial Alzheimer's disease. Accordingly, a compound that reduces production of Aβ40 and Aβ42 is expected to be a progression inhibitor or prophylactic agent for Alzheimer's disease.

Aβ is produced by the cleavage APP by beta-secretase (BACE1) and subsequently by gamma-secretase. For this reason, attempts have been made to create gamma-secretase and beta-secretase inhibitors in order to inhibit Aβ production. Already known beta-secretase inhibitors are reported in Patent Documents 1 and 2 shown below and the like. In particular, International Patent application nos. WO2007/049532 and WO2008/133273 (both Shionogi & Co., Ltd) describe aminodihydro-thiazine derivatives having BACE1 inhibitory activity.

BRIEF SUMMARY OF THE INVENTION

An object of the present invention is to provide a fused aminodihydro-oxazine compound which has an Aβ production inhibitory effect or a BACE1 inhibitory effect and is useful as a prophylactic or therapeutic agent for a neurodegenerative disease caused by Aβ and typified by Alzheimer-type dementia, and pharmaceutical use thereof.

The present invention relates to:
[1] A compound represented by the formula (I):

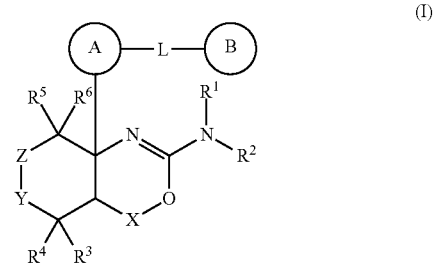

or a pharmaceutically acceptable salt thereof or a solvate thereof, wherein

Ring A is a $C_{6-14}$ aryl group which optionally has 1 to 3 substituents selected from Substituent Group α, a 5- to 6-membered heteroaryl group which optionally has 1 to 3 substituents selected from Substituent Group α or a 9- to 10-membered benzo-fused heterocyclic group which optionally has 1 to 3 substituents selected from Substituent Group α;

L is a single bond, an oxygen atom, a formula —NR$^e$CO— (wherein R$^e$ is a hydrogen atom or a $C_{1-6}$ alkyl group which optionally has 1 to 3 substituents selected from Substituent Group α), a formula —NR$^e$SO$_2$— (wherein R$^e$ is a hydrogen atom or a $C_{1-6}$ alkyl group which optionally has 1 to 3 substituents selected from Substituent Group α), a formula —NR$^e$— (wherein R$^e$ is a hydrogen atom or a $C_{1-6}$ alkyl group which optionally has 1 to 3 substituents selected from Substituent Group α), a $C_{1-6}$ alkylene group which optionally has 1 to 3 substituents selected from Substituent Group α, a $C_{2-6}$ alkenylene group which optionally has 1 to 3 substituents selected from Substituent Group α or a $C_{2-6}$ alkynylene group which optionally has 1 to 3 substituents selected from Substituent Group α;

Ring B is a $C_{3-8}$ cycloalkyl group which optionally has 1 to 3 substituents selected from Substituent Group α, a $C_{6-14}$ aryl group which optionally has 1 to 3 substituents selected from Substituent Group α or a 5- to 10-membered heterocyclic group which optionally has 1 to 3 substituents selected from Substituent Group α;

X is a single bond or a $C_{1-3}$ alkylene group which optionally has 1 to 3 substituents selected from Substituent Group α;

Y is a single bond, —NR$^Y$— (wherein R$^Y$ is a hydrogen atom, a $C_{1-6}$ alkyl group which optionally has 1 to 3 substituents selected from Substituent Group α, a $C_{1-6}$ alkylcarbonyl group which optionally has 1 to 3 substituents selected from Substituent Group α, a $C_{6-14}$ arylcarbonyl group which optionally has 1 to 3 substituents selected from Substituent Group α, a $C_{1-6}$ alkylsulfonyl group which optionally has 1 to 3 substituents selected from Substituent Group α, a $C_{6-14}$ arylsulfonyl group which optionally has 1 to 3 substituents selected from Substituent Group α, a $C_{6-14}$ aryl group which optionally has 1 to 3 substituents selected from Substituent Group α or a 5- to 10-membered heterocyclic group which optionally has 1 to 3 substituents selected from Substituent Group α), an oxygen atom, a sulfur atom, a sulfoxide or a sulfone;

Z is a single bond, a $C_{1-3}$ alkylene group which optionally has 1 to 3 substituents selected from Substituent Group α or a $C_{2-3}$ alkenylene group which may have 1 to 3 substituents selected from Substituent Group α;

$R^1$ and $R^2$ are each independently a hydrogen atom, a $C_{1-6}$ alkyl group which optionally has 1 to 3 substituents selected from Substituent Group α, a C$_{1-6}$ alkylcarbonyl group which optionally has 1 to 3 substituents selected from Substituent Group α, a C$_{6-14}$ arylcarbonyl group which optionally has 1 to 3 substituents selected from Substituent Group α, a C$_{1-6}$ alkylsulfonyl group which optionally has 1 to 3 substituents selected from Substituent Group α, a C$_{6-14}$ arylsulfonyl group which optionally has 1 to 3 substituents selected from Substituent Group α, a 3- to 10-membered carbocyclic group which optionally has 1 to 3 substituents selected from Substituent Group α or a 5- to 10-membered heterocyclic group which optionally has 1 to 3 substituents selected from Substituent Group α; and R$^3$, R$^4$, R$^5$ and R$^6$ are independently a hydrogen atom, a halogen atom, a hydroxy group, a C$_{1-6}$ alkyl group which optionally has 1 to 3 substituents selected from Substituent Group α, a C$_{1-6}$ alkoxy group which optionally has 1 to 3 substituents selected from Substituent Group α, a 3- to 10-membered carbocyclic group which optionally has 1 to 3 substituents selected from Substituent Group α or a 5- to 10-membered heterocyclic group which optionally has 1 to 3 substituents selected from Substituent Group α; or R$^4$ and R$^6$ together form a ring represented by the formula (II):

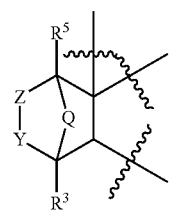

(II)

wherein Y, Z, R$^5$ and R$^3$ are the same as defined above and Q is an oxygen atom, a methylene group or an ethylene group;

[Substituent Group α: a hydrogen atom, a halogen atom, a hydroxy group, a nitro group, a C$_{1-6}$ alkylthio group, a C$_{6-14}$ aryl group, aryloxycarbonyl group, a C$_{6-14}$, a C$_{6-14}$ arylcarbonyl group, a cyano group, a C$_{3-8}$ cycloalkoxy group, a C$_{3-8}$ cycloalkyl group, a C$_{3-8}$ cycloalkylthio group, a sulfonylamino group (wherein the sulfonylamino group is optionally substituted with a C$_{1-6}$ alkyl group), a C$_{2-6}$ alkenyl group which optionally has 1 to 3 substituents selected from Substituent Group β, a C$_{2-6}$ alkynyl group which optionally has 1 to 3 substituents selected from Substituent Group β, a carbamoyl group which is optionally substituted with one or two C$_{1-6}$ alkyl groups, a C$_{1-6}$ alkoxy group which optionally has 1 to 3 substituents selected from Substituent Group β, a C$_{1-6}$ alkyl group which optionally has 1 to 3 substituents selected from Substituent Group β and a 5- to 10-membered heterocyclic group which optionally has 1 to 3 substituents selected from Substituent Group β;

Substituent Group β: a halogen atom, a cyano group, a hydroxy group, a C$_{1-6}$ alkoxy group, a C$_{1-6}$ alkyl group, a C$_{3-8}$ cycloalkyl group and an oxo group];

[2] The compound or pharmaceutically acceptable salt thereof or solvate thereof according to [1] above, wherein X is a methylene which optionally has 1 to 2 substituents selected from Substituent Group α;

[3] The compound or pharmaceutically acceptable salt thereof or solvate thereof according to [1] or [2] above, wherein Y is an oxygen atom;

[4] The compound or pharmaceutically acceptable salt thereof or solvate thereof according to any one of [1] to [3] above, wherein Z is a single bond;

[5] The compound or pharmaceutically acceptable salt thereof or solvate thereof according to any one of [1] to [4] above, wherein L is a single bond, a formula —NR$^e$CO— (wherein R$^e$ is a hydrogen atom or a C$_{1-6}$ alkyl group which optionally has 1 to 3 substituents selected from Substituent Group α) or a formula —NR$^e$SO$_2$— (wherein R$^e$ is a hydrogen atom or a C$_{1-6}$ alkyl group which optionally has 1 to 3 substituents selected from Substituent Group α);

[6] The compound or pharmaceutically acceptable salt thereof or solvate thereof according to [5] above, wherein L is a formula —NR$^e$CO— (wherein R$^e$ is a hydrogen atom or a C$_{1-6}$ alkyl group which optionally has 1 to 3 substituents selected from Substituent Group α);

[7] The compound or pharmaceutically acceptable salt thereof or solvate thereof according to any one of [1] to [6] above, wherein Ring A is a C$_{6-14}$ aryl group which optionally has 1 to 3 substituents selected from Substituent Group α;

[8] The compound or pharmaceutically acceptable salt thereof or solvate thereof according to any one of [1] to [6] above, wherein Ring B is a 5 to 10-membered heterocyclic group which optionally has 1 to 3 substituents selected from Substituent Group α;

[9] The compound or pharmaceutically acceptable salt thereof or solvate thereof according to any one of [1] to [8] above, wherein the compound is selected from:

N-(3-((4a,5,7a)-2-amino-5-(fluoromethyl)-4a,5,7,7a-tetrahydro-4H-furo[3,4-d][1,3]oxazin-7a-yl)-4-fluorophenyl)-5-(difluoromethyl)pyrazine-2-carboxamide:

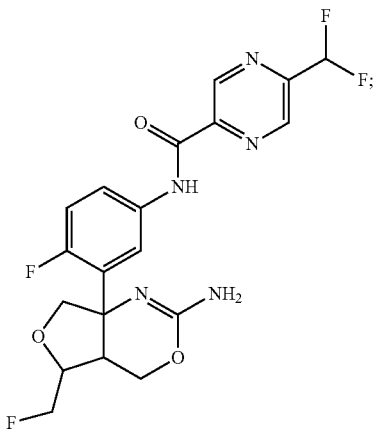

N-(3-(2-amino-5-(fluoromethyl)-4a,5,7,7a-tetrahydro-4H-furo[3,4-d][1,3]oxazin-7a-yl)-4-fluorophenyl)-5-methoxypyrazine-2-carboxamide:

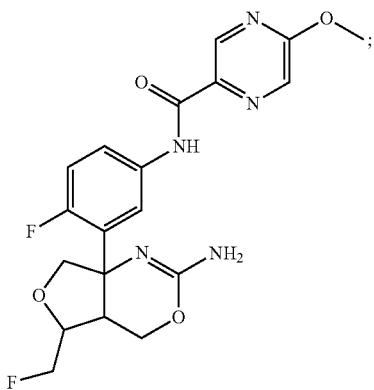 [SMILES: COc1cnc(C(=O)Nc2ccc(F)c(C34COC(CF)C3COC(N)=N4)c2)cn1]

N-(3-(2-amino-5-(fluoromethyl)-4a,5,7,7a-tetrahydro-4H-furo[3,4-d][1,3]oxazin-7a-yl)-4-fluorophenyl)-5-(difluoromethoxy)pyrazine-2-carboxamide:

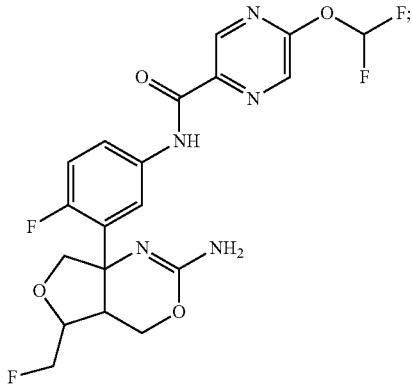

N-(3-(2-amino-5-(fluoromethyl)-4a,5,7,7a-tetrahydro-4H-furo[3,4-d][1,3]oxazin-7a-yl)-4-fluorophenyl)-5-(fluoromethoxy)pyrazine-2-carboxamide:

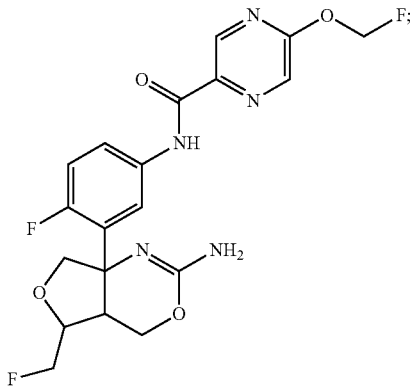 [SMILES: NC1=NC2(c3cc(NC(=O)c4cnc(OCF)cn4)ccc3F)COC(CF)C2CO1]

N-(3-(2-amino-5-(fluoromethyl)-4a,5,7,7a-tetrahydro-4H-furo[3,4-d][1,3]oxazin-7a-yl)-4-fluorophenyl)-5-ethoxypyrazine-2-carboxamide:

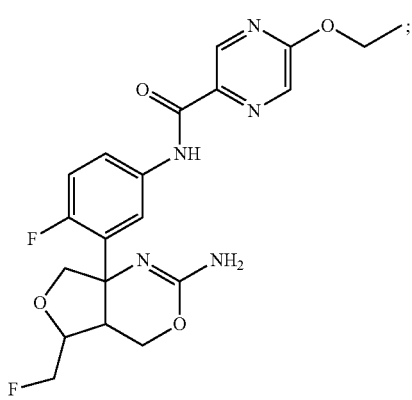 [SMILES: CCOc1cnc(C(=O)Nc2ccc(F)c(C34COC(CF)C3COC(N)=N4)c2)cn1]

N-(3-(2-amino-5-(fluoromethyl)-4a,5,7,7a-tetrahydro-4H-furo[3,4-d][1,3]oxazin-7a-yl)-4-fluorophenyl)-5-fluoropicolinamide:

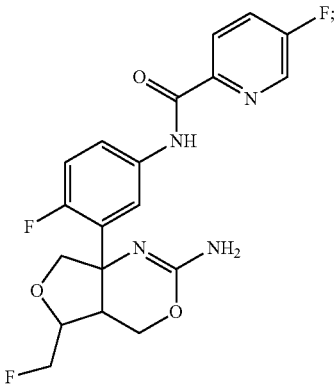

N-(3-(2-amino-5-(fluoromethyl)-4a,5,7,7a-tetrahydro-4H-furo[3,4-d][1,3]oxazin-7a-yl)-4-fluorophenyl)-5-cyanopicolinamide:

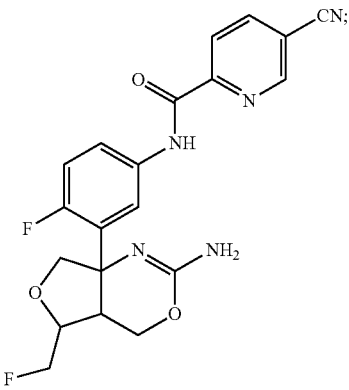 [SMILES: N#Cc1ccc(C(=O)Nc2ccc(F)c(C34COC(CF)C3COC(N)=N4)c2)nc1]

N-(3-(2-amino-5-(fluoromethyl)-4a,5,7,7a-tetrahydro-4H-furo[3,4-d][1,3]oxazin-7a-yl)-4-fluorophenyl)-5-chloropicolinamide:

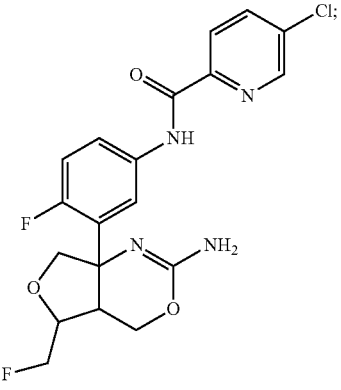 [SMILES: NC1=NC2(c3cc(NC(=O)c4ccc(Cl)cn4)ccc3F)COC(CF)C2CO1]

7

N-(3-(2-amino-5-(fluoromethyl)-4a,5,7,7a-tetrahydro-4H-furo[3,4-d][1,3]oxazin-7a-yl)-4-fluorophenyl)-5-(trifluoromethyl)picolinamide:

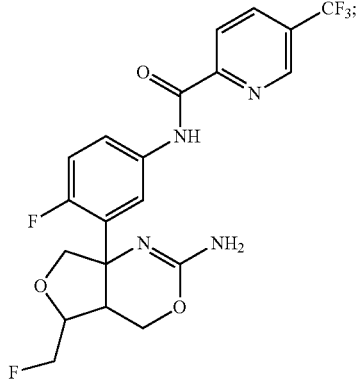 [SMILES: NC1=NC2(c3cc(NC(=O)c4ccc(C(F)(F)F)cn4)ccc3F)COC(CF)C2CO1]

N-(3-(2-amino-5-(fluoromethyl)-4a,5,7,7a-tetrahydro-4H-furo[3,4-d][1,3]oxazin-7a-yl)-4-fluorophenyl)-5-(difluoromethyl)picolinamide:

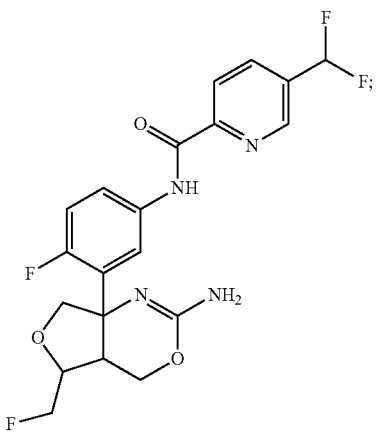 [SMILES: NC1=NC2(c3cc(NC(=O)c4ccc(C(F)F)cn4)ccc3F)COC(CF)C2CO1]

N-(3-(2-amino-5-(fluoromethyl)-4a,5,7,7a-tetrahydro-4H-furo[3,4-d][1,3]oxazin-7a-yl)-4-fluorophenyl)-5-(fluoromethyl)picolinamide:

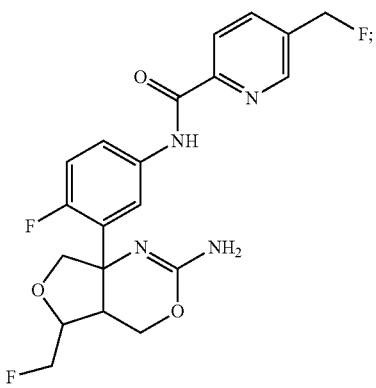 [SMILES: NC1=NC2(c3cc(NC(=O)c4ccc(CF)cn4)ccc3F)COC(CF)C2CO1]

8

N-(3-(2-amino-5-(fluoromethyl)-4a,5,7,7a-tetrahydro-4H-furo[3,4-d][1,3]oxazin-7a-yl)-4-fluorophenyl)-5-methoxypicolinamide:

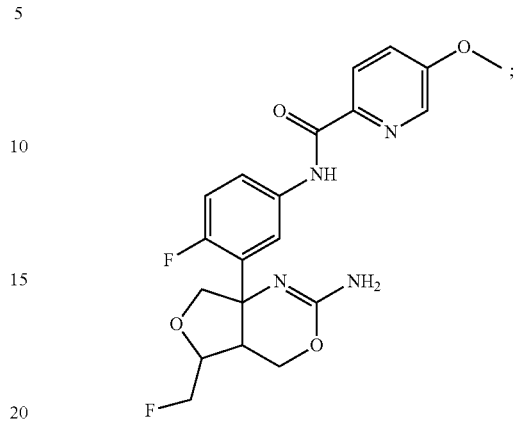

N-(3-(2-amino-5-(fluoromethyl)-4a,5,7,7a-tetrahydro-4H-furo[3,4-d][1,3]oxazin-7a-yl)-4-fluorophenyl)-5-(difluoromethoxy)picolinamide:

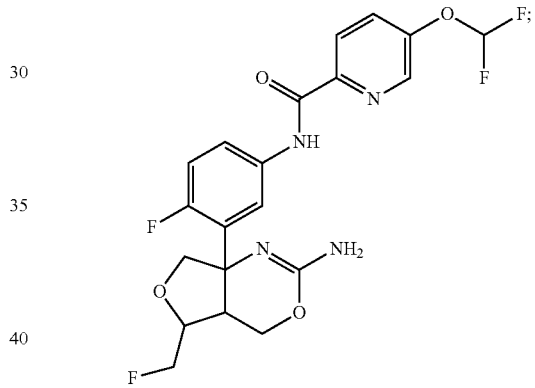

N-(3-((4aR,5S,7aS)-2-amino-5-(trifluoromethyl)-4a,5,7,7a-tetrahydro-4H-furo[3,4-d][1,3]oxazin-7a-yl)-4-fluorophenyl)-5-cyanopicolinamide:

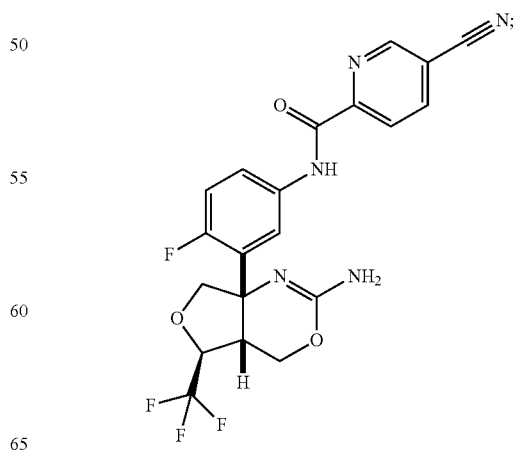

N-(3-((4aR,5S,7aS)-2-amino-5-(trifluoromethyl)-4a,5,7,7a-tetrahydro-4H-furo[3,4-d][1,3]oxazin-7a-yl)-4-fluorophenyl)-5-(difluoromethyl)pyrazine-2-carboxamide:

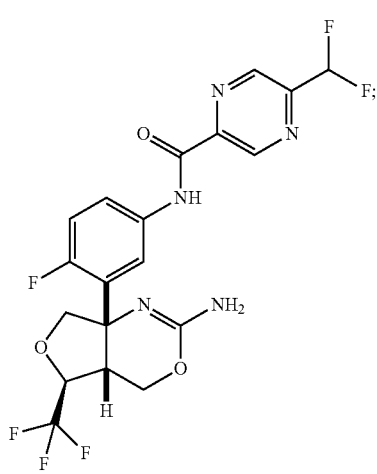

N-(3-((4aR,5S,7aS)-2-amino-5-(trifluoromethyl)-4a,5,7,7a-tetrahydro-4H-furo[3,4-d][1,3]oxazin-7a-yl)-4-fluorophenyl)-5-methoxypyrazine-2-carboxamide:

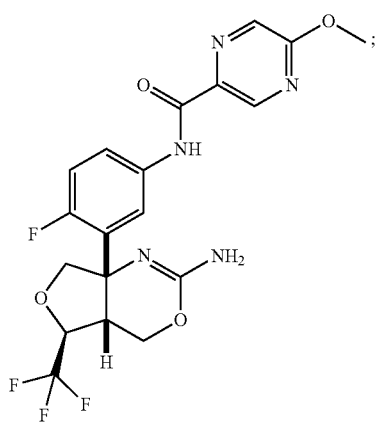

N-(3-((4aR,5S,7aS)-2-amino-5-(trifluoromethyl)-4a,5,7,7a-tetrahydro-4H-furo[3,4-d][1,3]oxazin-7a-yl)-4-fluorophenyl)-5-methylpyrazine-2-carboxamide:

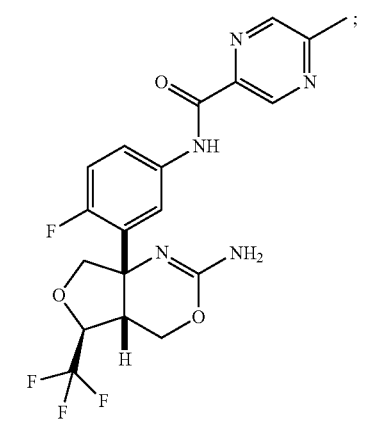

N-(3-((4aR,5S,7aS)-2-amino-5-(trifluoromethyl)-4a,5,7,7a-tetrahydro-4H-furo[3,4-d][1,3]oxazin-7a-yl)-4-fluorophenyl)-5-(trifluoromethyl)picolinamide:

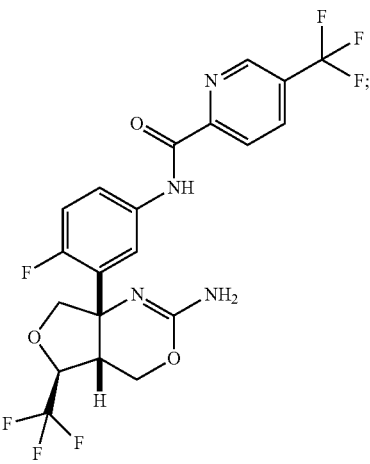

N-(3-((4aR,5S,7aS)-2-amino-5-(trifluoromethyl)-4a,5,7,7a-tetrahydro-4H-furo[3,4-d][1,3]oxazin-7a-yl)-4-fluorophenyl)-5-(fluoromethyl)pyrazine-2-carboxamide:

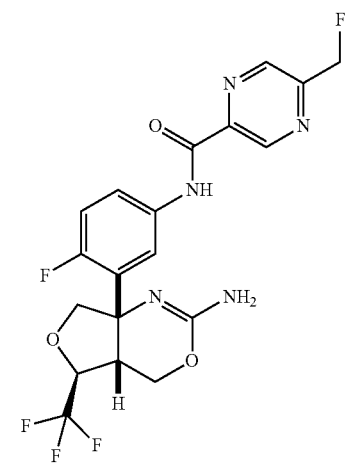

N-(3-((4aR,5S,7aS)-2-amino-5-(trifluoromethyl)-4a,5,7,7a-tetrahydro-4H-furo[3,4-d][1,3]oxazin-7a-yl)-4-fluorophenyl)-5-methylpicolinamide:

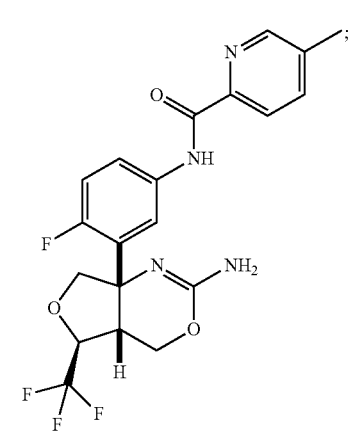

N-(3-((4aR,5S,7aS)-2-amino-5-(trifluoromethyl)-4a,5,7,7a-tetrahydro-4H-furo[3,4-d][1,3]oxazin-7a-yl)-4-fluorophenyl)-5-ethylpicolinamide:

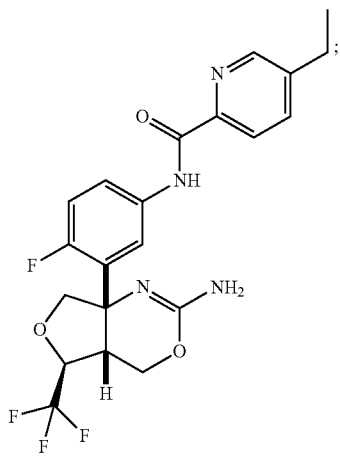

N-(3-((4aR,5S,7aS)-2-amino-5-(trifluoromethyl)-4a,5,7,7a-tetrahydro-4H-furo[3,4-d][1,3]oxazin-7a-yl)-4-fluorophenyl)-5-ethoxypyrazine-2-carboxamide:

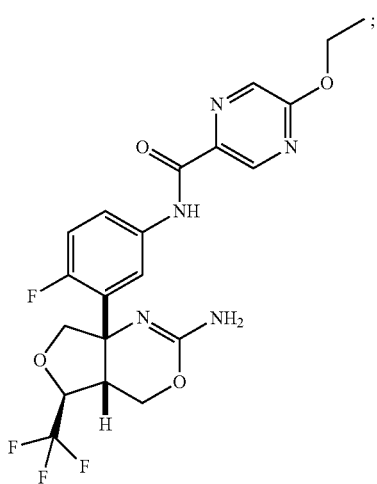

N-(3-((4aR,5S,7aS)-2-amino-5-(trifluoromethyl)-4a,5,7,7a-tetrahydro-4H-furo[3,4-d][1,3]oxazin-7a-yl)-4-fluorophenyl)-5-(1,1-difluoromethyl)pyrazine-2-carboxamide:

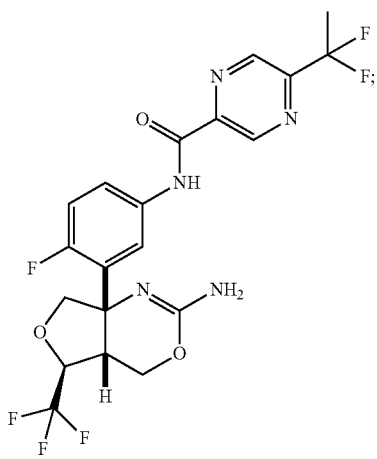

and
5-Difluoromethyl-pyrazine-2-carboxylic acid [3-((1S,4aS,5R,7aS)-2-amino-5-methyl-4-trifluoromethyl-4a,5-dihydro-4H-furo[3,4-d][1,3]oxazin-7a-yl)-4-fluoro-phenyl]-amide:

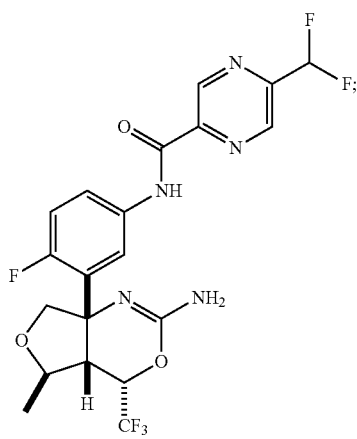 [SMILES: C[C@H]1OC[C@]2(c3cc(NC(=O)c4cnc(C(F)F)cn4)ccc3F)N=C(N)O[C@H](C(F)(F)F)[C@H]12]

[10] The compound or pharmaceutically acceptable salt thereof or solvate thereof according to any one of [1] to [9] above, wherein the compound has the following stereochemistry:

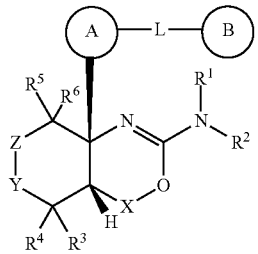

[11] A pharmaceutical composition comprising the compound or pharmaceutically acceptable salt thereof or solvate thereof according to any one of [1] to [10] above as an active ingredient;

[12] The compound or pharmaceutically acceptable salt thereof or solvate thereof according to any one of [1] to [10] above or the pharmaceutical composition according to [11] above for inhibiting production of amyloid-13 protein;

[13] The compound or pharmaceutically acceptable salt thereof or solvate thereof according to any one of [1] to [10] above or the pharmaceutical composition according to [11] above for inhibiting beta-site amyloid-13 precursor protein cleaving enzyme 1 (BACE1);

[14] The compound or pharmaceutically acceptable salt thereof or solvate thereof according to any one of [1] to [10] above or the pharmaceutical composition according to any one of [11] to [13] above for treating a neurodegenerative disease;

[15] The compound or pharmaceutically acceptable salt thereof or solvate thereof or the pharmaceutical composition according to [14] above, wherein the neurodegenerative disease is Alzheimer-type dementia or Down's syndrome;

[16] A method of inhibiting production of amyloid-13 protein and/or of treating or preventing a neurodegenerative disease, such as Alzheimer-type dementia and Down's syndrome, the method involving administering to a human subject suffering from the condition a therapeutically or prophylactically effective amount of a compound or pharmaceutically acceptable salt thereof according to any one of [1] to [10] above or the pharmaceutical composition according to [11] above; and

[17] Use of a compound or a pharmaceutically acceptable salt thereof according to any one of [1] to [10] above, for the manufacture of a medicament for the treatment or prevention of a neurodegenerative disease.

DETAILED DESCRIPTION OF THE INVENTION

Meanings of symbols, terms and the like used in the present specification will be explained and the present invention will be described in detail below.

In the present specification, a structural formula of a compound may represent a certain isomer for convenience. However, the present invention includes all isomers and isomer mixtures such as geometric isomers which can be generated from the structure of a compound, optical isomers based on asymmetric carbon, stereoisomers and tautomers. The present invention is not limited to the description of a chemical formula for convenience and may include any one of the isomers or mixtures thereof. Accordingly, the compound of the present invention may have an asymmetric carbon atom in the molecule and exist as an optically active compound or racemate, and the present invention includes each of the optically active compound and the racemate without limitations. Although crystal polymorphs of the compound may be present, the compound is similarly not limited thereto and may be present as a single crystal form or a mixture of single crystal forms. The compound may be an anhydride or a hydrate. Any of these forms is included in the claims of the present specification.

The present invention also includes isotopically-labelled compounds, which are identical to the compounds of formula (I), except that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine, iodine, and chlorine, such as $^2$H, $^3$H, $^{11}$C, $^{14}$C, $^{18}$F, $^{35}$S, $^{123}$I and $^{125}$I.

Compounds of the present invention and pharmaceutically acceptable derivatives (e.g. salts) of said compounds that contain the aforementioned isotopes and/or other isotopes of other atoms are within the scope of the present invention. Isotopically-labelled compounds of the present invention, for example those into which radioactive isotopes such as $^3$H and/or $^{14}$C are incorporated, are useful in drug and/or substrate tissue distribution assays. $^3$H and $^{14}$C are considered useful due to their ease of preparation and detectability. $^{11}$C and $^{18}$F isotopes are considered useful in PET (positron emission tomography), and $^{125}$I isotopes are considered useful in SPECT (single photon emission computerized tomography), all useful in brain imaging. Substitution with heavier isotopes such as $^2$H can afford certain therapeutic advantages resulting from greater metabolic stability, for example increased in vivo half-life or reduced dosage requirements and, hence, are considered useful in some circumstances. Isotopically labelled compounds of formula (I) of this invention can generally be prepared by carrying out the procedures disclosed in the Schemes and/or in the Examples below, by substituting a readily available isotopically labelled reagent for a non-isotopically labelled reagent.

The "halogen atom" herein refers to fluorine, chlorine, bromine, iodine or the like and is preferably fluorine or chlorine.

The "$C_{1-6}$ alkyl group" refers to an alkyl group having 1 to 6 carbon atoms. Preferable examples of the group include linear or branched alkyl groups such as methyl, ethyl, n-propyl, isopropyl, n-butyl, isobutyl, t-butyl, n-pentyl, isopentyl, neopentyl, n-hexyl, 1-methylpropyl, 1,2-dimethylpropyl, 1-ethylpropyl, 1-methyl-2-ethylpropyl, 1-ethyl-2-methylpropyl, 1,1,2-trimethylpropyl, 1-methylbutyl, 2-methylbutyl, 1,1-dimethylbutyl, 2,2-dimethylbutyl, 2-ethylbutyl, 1,3-dimethylbutyl, 2-methylpentyl and 3-methylpentyl. The group is more preferably methyl, ethyl or n-propyl.

The "$C_{2-6}$ alkenyl group" refers to an alkenyl group having 2 to 6 carbon atoms. Preferable examples of the group include linear or branched alkenyl groups such as vinyl, allyl, 1-propenyl, isopropenyl, 1-buten-1-yl, 1-buten-2-yl, 1-buten-3-yl, 2-buten-1-yl and 2-buten-2-yl.

The "$C_{2-6}$ alkynyl group" refers to an alkynyl group having 2 to 6 carbon atoms. Preferable examples of the group include linear or branched alkynyl groups such as ethynyl, 1-propynyl, 2-propynyl, butynyl, pentynyl and hexynyl.

The "$C_{1-6}$ alkoxy group" refers to an alkyl group having 1 to 6 carbon atoms in which one methylene group is replaced by an oxygen atom. Examples of the group include methoxy, ethoxy, n-propoxy, isopropoxy, n-butoxy, isobutoxy, sec-butoxy, t-butoxy, n-pentoxy, isopentoxy, sec-pentoxy, t-pentoxy, n-hexyloxy, isohexyloxy, 1,2-dimethylpropoxy, 2-ethylpropoxy, 1-methyl-2-ethylpropoxy, 1-ethyl-2-methylpropoxy, 1,1,2-trimethylpropoxy, 1,1-dimethylbutoxy, 2,2-dimethylbutoxy, 2-ethylbutoxy, 1,3-dimethylbutoxy, 2-methylpentoxy, 3-methylpentoxy and hexyloxy.

The "$C_{1-6}$ alkylthio group" refers to an alkyl group having 1 to 6 carbon atoms in which one methylene group is replaced by a sulfur atom. Examples of the group include methylthio, ethylthio, n-propylthio, isopropylthio, n-butylthio, isobutylthio, t-butylthio, n-pentylthio, isopentylthio, neopentylthio, n-hexylthio and 1-methylpropylthio.

The "$C_{1-6}$ alkylsulfonyl group" refers to an alkyl group having 1 to 6 carbon atoms in which one methylene group is replaced by a sulfonyl group. Examples of the group include methylsulfonyl, ethylsulfonyl, n-propylsulfonyl, isopropylsulfonyl, n-butylsulfonyl, isobutylsulfonyl, t-butylsulfonyl, n-pentylsulfonyl, isopentylsulfonyl, neopentylsulfonyl, n-hexylsulfonyl and 1-methylpropylsulfonyl.

The "$C_{1-6}$ alkylcarbonyl group" refers to an alkyl group having 1 to 6 carbon atoms in which one methylene group is replaced by a carbonyl group. Preferable examples of the group include acetyl, propionyl and butyryl.

The "$C_{6-14}$ aryl group" refers to an aromatic hydrocarbon ring group having 6 to 14 carbon atoms. Examples of the group include phenyl, naphthyl and anthryl. Phenyl is particularly preferred.

The "$C_{7-12}$ aralkyl group" refers to a group having 7 to 12 carbon atoms in which an aromatic hydrocarbon ring such as a phenyl group or a naphthyl group is substituted with a $C_{1-6}$ alkyl group. Examples of the group include benzyl, phenethyl, phenylpropyl and naphthylmethyl. Benzyl is particularly preferred.

The "$C_{6-14}$ aryloxycarbonyl group" refers to a group in which oxycarbonyl is bonded to an aromatic hydrocarbon ring group having 6 to 14 carbon atoms.

Preferable examples of the group include phenyloxycarbonyl, naphthyloxycarbonyl and anthryloxycarbonyl. Phenyloxycarbonyl is preferred.

The "$C_{6-14}$ arylcarbonyl group" refers to a group in which a carbonyl group is bonded to an aromatic hydrocarbon ring group having 6 to 14 carbon atoms. Preferable examples of the group include benzoyl and naphthoyl. Benzoyl is more preferred.

The "$C_{6-14}$ arylsulfonyl group" refers to a group in which a sulfonyl group is bonded to an aromatic hydrocarbon ring group having 6 to 14 carbon atoms. Preferable examples of the group include benzenesulfonyl and naphthylsulfonyl. Benzenesulfonyl is more preferred.

The "$C_{3-8}$ cycloalkyl group" refers to a cyclic alkyl group having 3 to 8 carbon atoms. Preferable examples of the group include cyclopropyl, cyclobutyl, cyclopentyl, cyclohexyl, cycloheptyl and cyclooctyl.

The "$C_{3-8}$ cycloalkoxy group" refers to a cyclic alkyl group having 3 to 8 carbon atoms in which one hydrogen atom is replaced by an oxygen atom. Examples of the group include cyclopropoxy, cyclobutoxy, cyclopentoxy, a cyclohexyloxy, cycloheptyloxy and cyclooctyloxy.

The "$C_{3-8}$ cycloalkylthio group" refers to a cyclic alkyl group having 3 to 8 carbon atoms in which one hydrogen atom is replaced by a sulfur atom. Examples of the group include cyclopropylthio, cyclobutylthio, cyclopentylthio, cyclohexylthio, cycloheptylthio and cyclooctylthio.

The "5- to 10-membered heterocyclic group" refers to a heteroatom-containing cyclic group having 5 to 10 members in total. Preferable examples of the group include piperidinyl, pyrrolidinyl, azepinyl, azocanyl, piperazinyl, 1,4-diazepanyl, morpholinyl, thiomorpholinyl, pyrrolyl, imidazolyl, pyrazolyl, pyridinyl, pyridazinyl, pyrimidinyl, pyrazinyl, triazolyl, triazinyl, tetrazolyl, isoxazolyl, oxazolyl, oxadiazolyl, isothiazolyl, thiazolyl, thiadiazolyl, furyl, thienyl, quinolinyl, isoquinolinyl, benzofuryl, benzopyranyl, benzimidazolyl, benzotriazolyl, benzisothiazolyl, indolinyl, isoindolinyl, chromanyl, isochromanyl, 1,3-dioxaindanyl and 1,4-dioxatetralinyl.

The "5- to 6-membered heteroaryl group" refers to the "5- to 10-membered heterocyclic group" which is a heteroatom-containing aromatic cyclic group having 5 to 6 members in total. Examples of the group include pyrrolyl, imidazolyl, pyrazolyl, pyridinyl, pyridazinyl, pyrimidinyl, pyrazinyl, triazolyl, triazinyl, tetrazolyl, isoxazolyl, oxazolyl, oxadiazolyl, isothiazolyl, thiazolyl, thiadiazolyl, furyl and thienyl.

The "9- to 10-membered benzo-fused heterocyclic group" refers to the "5- to 10-membered heterocyclic group" which is a heteroatom-containing cyclic group having 9 to 10 members in total fused with a benzene ring. Preferable examples of the group include indolinyl, isoindolinyl, chromanyl, isochromanyl, 1,3-dioxaindanyl and 1,4-dioxatetralinyl.

The "3- to 10-membered carbocyclic group" refers to a carbocyclic group having 3 to 10 members in total. Preferable examples of the group include cyclopropyl, cyclobutyl, cyclopentyl, cyclohexyl, cycloheptyl, cyclooctyl, spiro[3.4]octanyl, decanyl, indanyl, 1-acenaphthenyl, cyclopentacyclooctenyl, benzocyclooctenyl, indenyl, tetrahydronaphthyl, 6,7,8,9-tetrahydro-5H-benzocycloheptenyl and 1,4-dihydronaphthalenyl.

The "$C_{1-6}$ alkylene group" refers to a divalent group derived by excluding any one hydrogen atom from the "$C_{1-6}$ alkyl group" as defined above. Examples of the group include methylene, 1,2-ethylene, 1,1-ethylene, 1,3-propylene, tetramethylene, pentamethylene and hexamethylene.

The "$C_{2-6}$ alkenylene group" refers to a divalent group derived by excluding any one hydrogen atom from the "$C_{2-6}$ alkenyl group" as defined above. Examples of the group include 1,2-vinylene (ethenylene), propenylene, butenylene, pentenylene and hexenylene.

The "$C_{2-6}$ alkynylene group" refers to a divalent group derived by excluding any one hydrogen atom from the "$C_{2-6}$ alkynyl group" as defined above. Examples of the group include ethynylene, propynylene, butynylene, pentynylene and hexynylene.

Examples of the "$C_{1-3}$ alkylene group" include methylene, ethylene and propylene.

Examples of the "$C_{2-3}$ alkenylene group" include 1,2-vinylene (ethenylene) and propenylene.

Examples of the "$C_{2-3}$ alkynylene group" include ethynylene and propynylene.

Examples of the sulfonylamino group which may be substituted with a $C_{1-6}$ alkyl group in the "sulfonylamino group (wherein the sulfonylamino group may be substituted with a $C_{1-6}$ alkyl group)" include methylsulfonylmethylamino, ethylsulfonylmethylamino and ethylsulfonylethylamino.

"Substituent Group α" refers to a hydrogen atom, a halogen atom, a hydroxy group, a nitro group, a $C_{1-6}$ alkylthio group, a $C_{6-14}$ aryl group, aryloxycarbonyl, a $C_{6-14}$ group, a $C_{6-14}$ arylcarbonyl group, a cyano group, a $C_{3-8}$ cycloalkoxy group, a $C_{3-8}$ cycloalkyl group, a $C_{3-8}$ cycloalkylthio group, a sulfonylamino group (wherein the sulfonylamino group may be substituted with a $C_{1-6}$ alkyl group), a $C_{2-6}$ alkenyl group which may have 1 to 3 substituents selected from Substituent Group β, a $C_{2-6}$ alkynyl group which may have 1 to 3 substituents selected from Substituent Group β, a carbamoyl group which may be substituted with one or two $C_{1-6}$ alkyl groups, a $C_{1-6}$ alkoxy group which may have 1 to 3 substituents selected from Substituent Group β, a $C_{1-6}$ alkyl group which may have 1 to 3 substituents selected from Substituent Group 13 and a 5- to 10-membered heterocyclic group which may have 1 to 3 substituents selected from Substituent Group β.

"Substituent Group β" refers to a halogen atom, a cyano group, a hydroxy group, a $C_{1-6}$ alkoxy group, a $C_{1-6}$ alkyl group, a $C_{3-8}$ cycloalkyl group and an oxo group.

The fused aminodihydro-oxazine derivative of the formula (I) according to the present invention may be a pharmaceutically acceptable salt. Pharmaceutically acceptable salts include those described by Berge, Bighley and Monkhouse, J. Pharm. Sci., 1977, 766, 1-19. Specific examples of the pharmaceutically acceptable salt include inorganic acid salts (such as sulfates, nitrates, perchlorates, phosphates, carbonates, bicarbonates, hydrofluorides, hydrochlorides, hydrobromides and hydroiodides), organic carboxylates (such as acetates, oxalates, maleates, tartrates, fumarates and citrates), organic sulfonates (such as methanesulfonates, trifluoromethanesulfonates, ethanesulfonates, benzenesulfonates, toluenesulfonates and camphorsulfonates), amino acid salts (such as aspartates and glutamates), quaternary amine salts, alkali metal salts (such as sodium salts and potassium salts) and alkali earth metal salts (such as magnesium salts and calcium salts).

The fused aminodihydro-oxazine derivative of the formula (I) or pharmaceutically acceptable salt according to the present invention may be a solvate thereof. Examples of the solvate include a hydrate.

The compound (I) is not limited to a specific isomer and includes all possible isomers (such as a keto-enol isomer, an imine-enamine isomer, a diastereoisomer, an optical isomer and a rotamer) and racemates. For example, the compound (I) wherein $R^1$ is hydrogen includes the following tautomers:

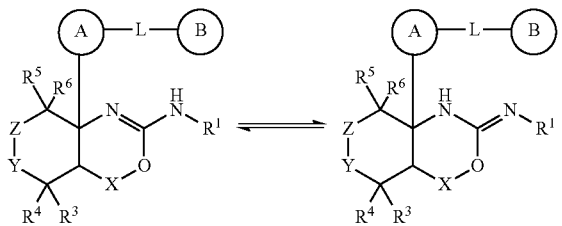

The fused aminodihydro-oxazine derivative of the formula (I) according to the present invention is preferably a compound of the formula (I), wherein X is a $C_{1-3}$ alkylene group which optionally has 1 to 3 substituents selected from Substituent Group α. More preferably, X is a methylene which optionally has 1 to 2 substituents selected from Substituent Group α. Most preferably, X is a methylene group.

The fused aminodihydro-oxazine derivative of the formula (I) according to the present invention is preferably a compound of the formula (I), wherein Y is —$NR^Y$— (wherein $R^Y$ is a hydrogen atom, a $C_{1-6}$ alkyl group which optionally has 1 to 3 substituents selected from Substituent Group α, a $C_{1-6}$ alkylcarbonyl group which optionally has 1 to 3 substituents selected from Substituent Group α, a $C_{6-14}$ arylcarbonyl group which optionally has 1 to 3 substituents selected from Substituent Group α, a $C_{1-6}$ alkylsulfonyl group which optionally has 1 to 3 substituents selected from Substituent Group α, a $C_{6-14}$ arylsulfonyl group which optionally has 1 to 3 substituents selected from Substituent Group α, a $C_{6-14}$ aryl group which optionally has 1 to 3 substituents selected from Substituent Group α or a 5- to 10-membered heterocyclic group which optionally has 1 to 3 substituents selected from Substituent Group α), an oxygen atom or a sulfur atom. More preferably, Y is an oxygen atom or a sulfur atom. Most preferably, Y is an oxygen atom.

The fused aminodihydro-oxazine derivative of the formula (I) according to the present invention is preferably a compound of the formula (I), wherein Z is a single bond.

The fused aminodihydro-oxazine derivative of the formula (I) according to the present invention is preferably a compound of the formula (I), wherein L is a single bond, a formula —$NR^eCO$— (wherein $R^e$ is a hydrogen atom or a $C_{1-6}$ alkyl group which optionally has 1 to 3 substituents selected from Substituent Group α) or a formula —$NR^eSO_2$— (wherein $R^e$ is a hydrogen atom or a $C_{1-6}$ alkyl group which optionally has 1 to 3 substituents selected from Substituent Group α); or wherein L is a single bond, an oxygen atom, a $C_{1-6}$ alkylene group which optionally has 1 to 3 substituents selected from Substituent Group α, a $C_{2-6}$ alkenylene group which optionally has 1 to 3 substituents selected from Substituent Group α or a $C_{2-6}$ alkynylene group which optionally has 1 to 3 substituents selected from Substituent Group α. More preferably, L is a formula —$NR^eCO$— (wherein $R^e$ is a hydrogen atom or a $C_{1-6}$ alkyl group which optionally has 1 to 3 substituents selected from Substituent Group α). Most preferably, L is NH—CO—. Especially, L is NH—CO where the nitrogen atom is attached to Ring A and the carbon atom is attached to Ring B.

The fused aminodihydro-oxazine derivative of the formula (I) according to the present invention is preferably a compound of the formula (I), wherein Ring A is a $C_{6-14}$ aryl group which optionally has 1 to 3 substituents selected from Substituent Group α. More preferably, Ring A is a $C_{6-10}$ aryl group which optionally has 1 to 2 substituents selected from Substituent Group α. Most preferably, Ring A is a phenyl group which optionally has 1 or 2 substituents selected from a halogen atom, a hydroxy group, a nitro group or a cyano group. Especially, Ring A is a phenyl group which is optionally substituted by a halogen atom. More especially, Ring A is a phenyl group which is optionally substituted by fluorine or chlorine. Most especially, Ring A is a phenyl group substituted by fluorine.

The fused aminodihydro-oxazine derivative of the formula (I) according to the present invention is preferably a compound of the formula (I), wherein Ring B is a 5 to 10-membered heterocyclic group which optionally has 1 to 3 substituents selected from Substituent Group α. More preferably, Ring B is a 5 to 8-membered heterocyclic group which optionally has 1 to 2 substituents selected from Substituent Group α. Most preferably, Ring B is a 5- or 6-membered heterocyclic group which optionally has 1 or 2 substituents selected from a halogen atom, a hydroxy atom, a nitro group, $C_{1-6}$ alkylthio group, a cyano group, a $C_{3-8}$ cycloalkoxy group, a $C_{3-8}$ cycloalkyl group, a $C_{3-8}$ cycloalkylthio group, a sulfonylamino group (wherein the sulfonylamino group is optionally substituted with a $C_{1-6}$ alkyl group), a $C_{2-6}$ alkenyl group which optionally has 1 to 3 substituents selected from Substituent Group β, a $C_{2-6}$ alkynyl group which optionally has 1 to 3 substituents selected from Substituent Group β, a $C_{1-6}$ alkoxy group which optionally has 1 to 3 substituents selected from Substituent Group β and a $C_{1-6}$ alkyl group which optionally has 1 to 3 substituents selected from Substituent Group β. Especially, Ring B is a 6-membered heterocyclic group which is optionally substituted by a halogen atom, a cyano group, a $C_{1-6}$ alkyl group which optionally has 1 to 3 substituents selected from Substituent Group β or a $C_{1-6}$ alkoxy group which optionally has 1 to 3 substituents selected from Substituent Group β. More especially, Ring B is pyridine or pyrazine, optionally substituted by a $C_{1-6}$ alkyl group which optionally has 1 to 3 substituents selected from a halogen atom, a cyano group, a hydroxy group and a $C_{1-6}$ alkoxy group. Most especially, Ring B is pyrazine optionally substituted by a $C_{1-3}$ alkyl group which optionally has 1 to 2 halogen atom substituents. Particularly, Ring B is pyrazine optionally substituted by a methyl group which optionally has 1 or 2 fluorine or chlorine atom substituents. More particularly, Ring B is pyrazine substituted by a difluoromethyl group. Examples of suitable substituted Ring B groups are 5-fluoropyridin-2-yl, 5-cyanopyridin-2-yl, 5-chloropyridin-2-yl, 5-trifluoromethylpyridin-2-yl, 5-difluoromethylpyridin-2-yl, 5-fluoromethylpyridin-2-yl, 5-methoxypyridin-2-yl, 5-difluoromethoxypyridin-2-yl, 5-methoxypyrazin-2-yl, 5-difluoromethylpyrazin-2-yl, 5-difluoromethoxypyrazin-2-yl, 5-fluoromethoxypyrazin-2-yl and 5-ethoxypyrazin-2-yl. Further examples of suitable substituted Ring B groups are 5-methylpyrazine-2-yl, 5-fluoromethylpyrazine-2-yl, 5-methylpyridin-2-yl, 5-ethylpyridin-2-yl and 5-(1,1-difluoroethyl)pyrazin-2-yl.

The fused aminodihydro-oxazine derivative of the formula (I) according to the present invention is preferably a compound of the formula (I), wherein $R^1$ and $R^2$ are each independently a hydrogen atom or a $C_{1-6}$ alkyl group which optionally has 1 to 3 substituents selected from Substituent Group α. More preferably, $R^1$ and $R^2$ are each independently a hydrogen atom or a $C_{1-3}$ alkyl group which optionally has 1 to 2 substituents selected from a halogen atom, a hydroxyl group, a nitro group and a cyano group. Most preferably, $R^1$ and $R^2$ are each independently a hydrogen atom or a $C_{1-2}$ alkyl group which optionally has 1 or 2 substituents selected from fluorine, chlorine, bromine, a hydroxyl group, a nitro group and a cyano group. Especially, $R^1$ and $R^2$ are both hydrogen.

The fused aminodihydro-oxazine derivative of the formula (I) according to the present invention is preferably a compound of the formula (I), wherein $R^3$ and $R^4$ are each independently a hydrogen atom, a halogen atom, a hydroxy group, a $C_{1-6}$ alkyl group which optionally has 1 to 3 substituents selected from Substituent Group α or a $C_{1-6}$ alkoxy group which optionally has 1 to 3 substituents selected from Substituent Group α. More preferably, $R^3$ and $R^4$ are independently a hydrogen atom or a $C_{1-6}$ alkyl group which optionally has 1 to 3 substituents selected from Substituent Group α. Most preferably, $R^3$ and $R^4$ are independently a hydrogen atom or a $C_{1-3}$ alkyl group which optionally has 1 to 3 substituents selected from a halogen atom, a hydroxy atom, a nitro group and a cyano group. Especially, $R^3$ and $R^4$ are independently a hydrogen atom or a $C_{1-2}$ alkyl group which is optionally substituted by a halogen atom, a hydroxy atom, a methoxy group, a nitro group or a cyano group. More especially, $R^3$ and $R^4$ are independently a hydrogen atom or a methyl group which is optionally substituted by a halogen atom. Most especially, especially, $R^3$ and $R^4$ are independently a hydrogen atom or a methyl group optionally substituted by a fluorine atom. Particularly, $R^3$ and $R^4$ are independently a hydrogen atom or a monofluoromethyl group. Particularly, $R^3$ is monofluoromethyl and $R^4$ is hydrogen. Examples of suitable $R^3$ groups are a hydrogen atom, a methyl group, a monofluoromethyl group, a difluoromethyl group, a trifluoromethyl group and a methoxymethyl group.

The fused aminodihydro-oxazine derivative of the formula (I) according to the present invention is preferably a compound of the formula (I), wherein $R^5$ and $R^6$ are each independently a hydrogen atom, a halogen atom, a hydroxy group, a $C_{1-6}$ alkyl group which optionally has 1 to 3 substituents selected from Substituent Group α or a $C_{1-6}$ alkoxy group which optionally has 1 to 3 substituents selected from Substituent Group α. More preferably, $R^5$ and $R^6$ are independently a hydrogen atom or a $C_{1-6}$ alkyl group which optionally has 1 to 3 substituents selected from Substituent Group α. Most preferably, $R^5$ and $R^6$ are independently a hydrogen atom or a $C_{1-3}$ alkyl group which optionally has 1 to 2 substituents selected from a halogen atom, a hydroxy atom, a nitro group and a cyano group. Especially, $R^5$ and $R^6$ are independently a hydrogen atom or a $C_{1-2}$ alkyl group which is optionally substituted by a halogen atom, a hydroxy atom, a nitro group or a cyano group. More especially, $R^5$ and $R^6$ are independently a hydrogen atom or a methyl group which is optionally substituted by a halogen atom. Most especially, especially, $R^5$ and $R^6$ are independently a hydrogen atom or a methyl group especially, $R^5$ and $R^6$ are independently a hydrogen atom or a methyl group. Particularly, $R^5$ and $R^6$ are both hydrogen.

One favoured group of compounds of the present invention is the compound of formula (Ii) and pharmaceutically acceptable salts thereof:

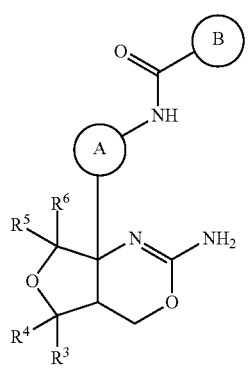

(Ii)

wherein Ring A, Ring B, $R^3$, $R^4$, $R^5$ and $R^6$ are as hereinbefore defined.

Preferred compounds of the present invention are:

N-(3-((4a,5,7a)-2-amino-5-(fluoromethyl)-4a,5,7,7a-tetrahydro-4H-furo[3,4-d][1,3]oxazin-7a-yl)-4-fluorophenyl)-5-(difluoromethyl)pyrazine-2-carboxamide:

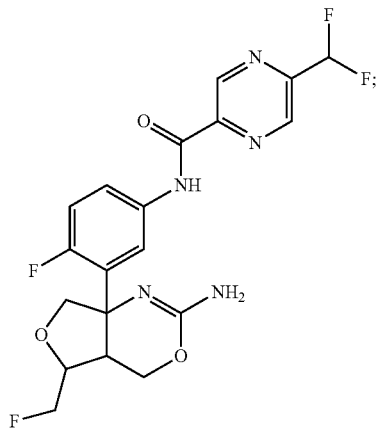 [SMILES: NC1=NC2(c3cc(NC(=O)c4cnc(C(F)F)cn4)ccc3F)COC(CF)C2CO1]

N-(3-(2-amino-5-(fluoromethyl)-4a,5,7,7a-tetrahydro-4H-furo[3,4-d][1,3]oxazin-7a-yl)-4-fluorophenyl)-5-methoxypyrazine-2-carboxamide:

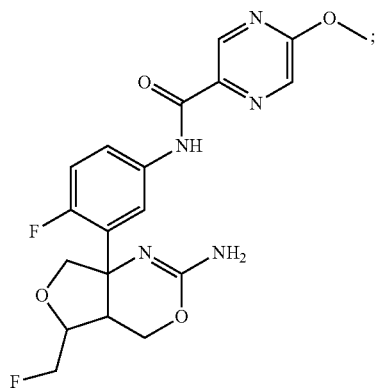 [SMILES: COc1cnc(C(=O)Nc2ccc(F)c(C34COC(CF)C3COC(N)=N4)c2)cn1]

N-(3-(2-amino-5-(fluoromethyl)-4a,5,7,7a-tetrahydro-4H-furo[3,4-d][1,3]oxazin-7a-yl)-4-fluorophenyl)-5-(difluoromethoxylpyrazine-2-carboxamide:

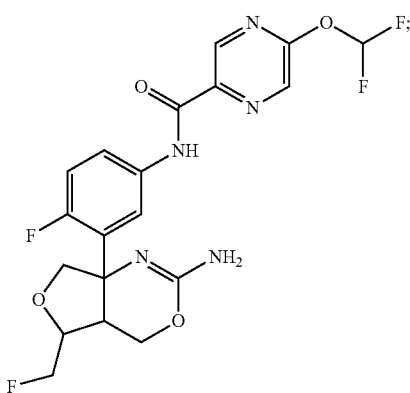

21

N-(3-(2-amino-5-(fluoromethyl)-4a,5,7,7a-tetrahydro-4H-furo[3,4-d][1,3]oxazin-7a-yl)-4-fluorophenyl)-5-(fluoromethoxy)pyrazine-2-carboxamide:

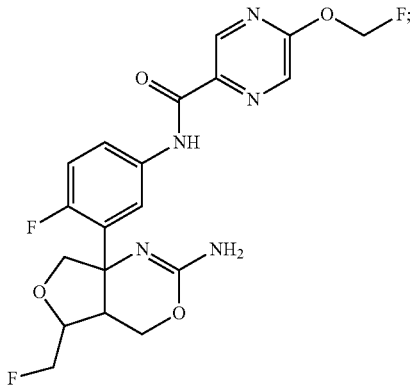

N-(3-(2-amino-5-(fluoromethyl)-4a,5,7,7a-tetrahydro-4H-furo[3,4-d][1,3]oxazin-7a-yl)-4-fluorophenyl)-5-ethoxypyrazine-2-carboxamide:

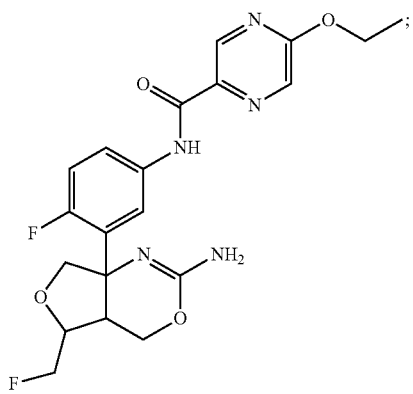

N-(3-(2-amino-5-(fluoromethyl)-4a,5,7,7a-tetrahydro-4H-furo[3,4-d][1,3]oxazin-7a-yl)-4-fluorophenyl)-5-fluoropicolinamide:

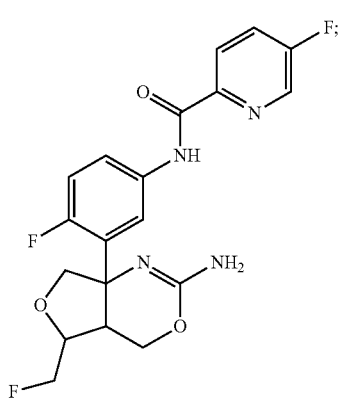 [SMILES: NC1=NC2(c3cc(NC(=O)c4ccc(F)cn4)ccc3F)COC(CF)C2CO1]

22

N-(3-(2-amino-5-(fluoromethyl)-4a,5,7,7a-tetrahydro-4H-furo[3,4-d][1,3]oxazin-7a-yl)-4-fluorophenyl)-5-cyanopicolinamide:

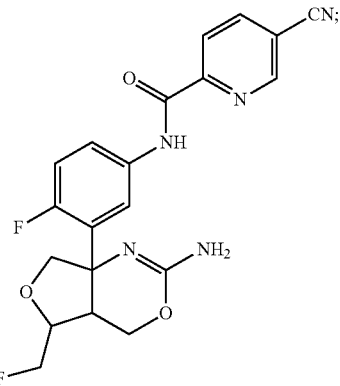

N-(3-(2-amino-5-(fluoromethyl)-4a,5,7,7a-tetrahydro-4H-furo[3,4-d][1,3]oxazin-7a-yl)-4-fluorophenyl)-5-chloropicolinamide:

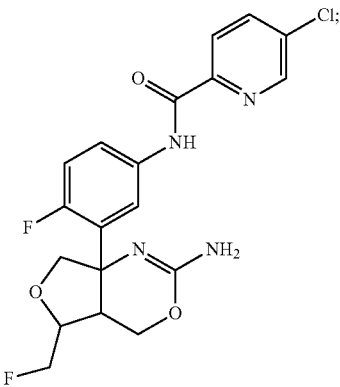 [SMILES: NC1=NC2(c3cc(NC(=O)c4ccc(Cl)cn4)ccc3F)COC(CF)C2CO1]

N-(3-(2-amino-5-(fluoromethyl)-4a,5,7,7a-tetrahydro-4H-furo[3,4-d][1,3]oxazin-7a-yl)-4-fluorophenyl)-5-(trifluoromethyl)picolinamide:

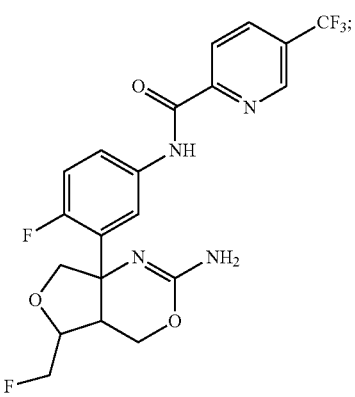 [SMILES: NC1=NC2(c3cc(NC(=O)c4ccc(C(F)(F)F)cn4)ccc3F)COC(CF)C2CO1]

N-(3-(2-amino-5-(fluoromethyl)-4a,5,7,7a-tetrahydro-4H-furo[3,4-d][1,3]oxazin-7a-yl)-4-fluorophenyl)-5-(difluoromethyl)picolinamide:

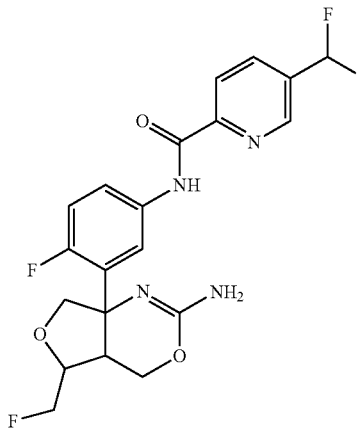

N-(3-(2-amino-5-(fluoromethyl)-4a,5,7,7a-tetrahydro-4H-furo[3,4-d][1,3]oxazin-7a-yl)-4-fluorophenyl)-5-(fluoromethyl)picolinamide:

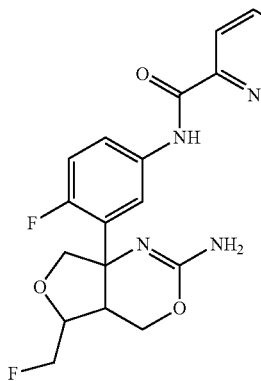

N-(3-(2-amino-5-(fluoromethyl)-4a,5,7,7a-tetrahydro-4H-furo[3,4-d][1,3]oxazin-7a-yl)-4-fluorophenyl)-5-methoxypicolinamide:

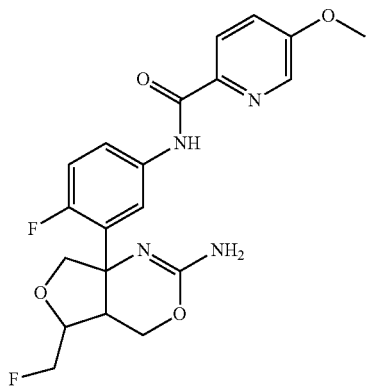

and
N-(3-(2-amino-5-(fluoromethyl)-4a,5,7,7a-tetrahydro-4H-furo[3,4-d][1,3]oxazin-7a-yl)-4-fluorophenyl)-5-(difluoromethoxy)picolinamide:

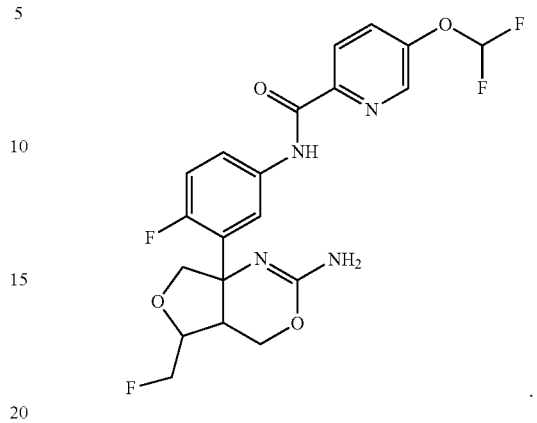

Further preferred compounds of the present invention are:
N-(3-((4aR,5S,7aS)-2-amino-5-(trifluoromethyl)-4a,5,7,7a-tetrahydro-4H-furo[3,4-d][1,3]oxazin-7a-yl)-4-fluorophenyl)-5-cyanopicolinamide:

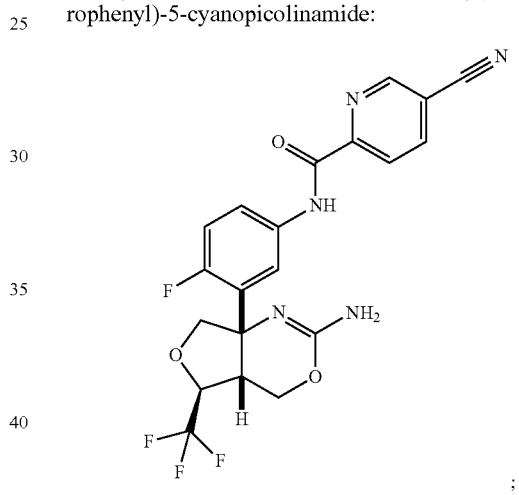

N-(3-((4aR,5S,7aS)-2-amino-5-(trifluoromethyl)-4a,5,7,7a-tetrahydro-4H-furo[3,4-d][1,3]oxazin-7a-yl)-4-fluorophenyl)-5-(difluoromethyl)pyrazine-2-carboxamide:

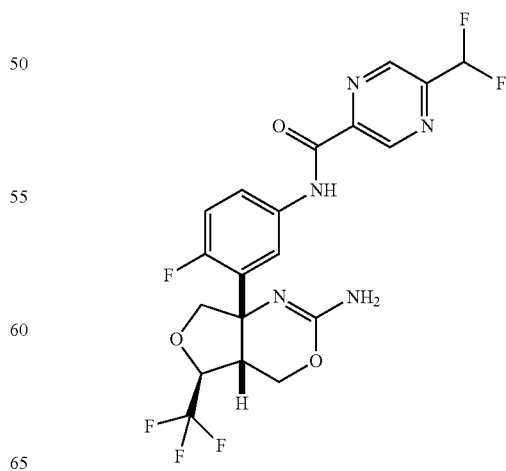

N-(3-((4aR,5S,7aS)-2-amino-5-(trifluoromethyl)-4a,5,7,7a-tetrahydro-4H-furo[3,4-d][1,3]oxazin-7a-yl)-4-fluorophenyl)-5-methoxypyrazine-2-carboxamide:

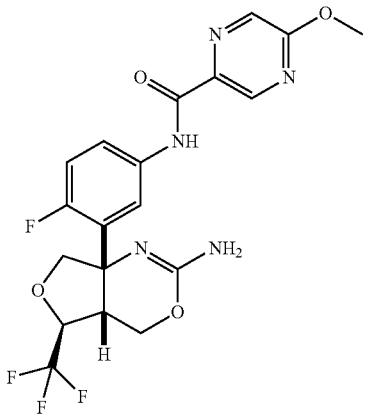

N-(3-((4aR,5S,7aS)-2-amino-5-(trifluoromethyl)-4a,5,7,7a-tetrahydro-4H-furo[3,4-d][1,3]oxazin-7a-yl)-4-fluorophenyl)-5-methylpyrazine-2-carboxamide:

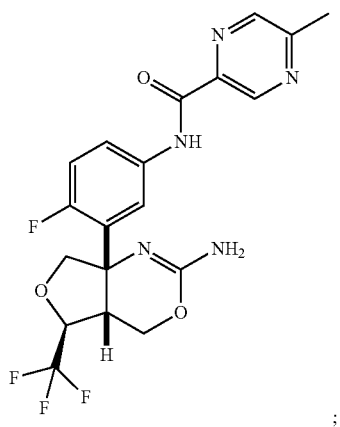 [SMILES: Cc1ccc(C(=O)Nc2ccc(F)c([C@]34CO[C@H](C(F)(F)F)[C@H]3COC(N)=N4)c2)nc1]

N-(3-((4aR,5S,7aS)-2-amino-5-(trifluoromethyl)-4a,5,7,7a-tetrahydro-4H-furo[3,4-d][1,3]oxazin-7a-yl)-4-fluorophenyl)-5-(trifluoromethyl)picolinamide:

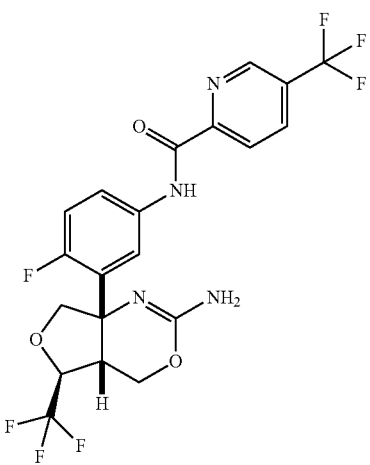

N-(3-((4aR,5S,7aS)-2-amino-5-(trifluoromethyl)-4a,5,7,7a-tetrahydro-4H-furo[3,4-d][1,3]oxazin-7a-yl)-4-fluorophenyl)-5-(fluoromethyl)pyrazine-2-carboxamide:

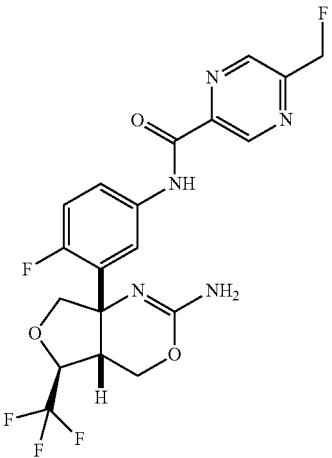

N-(3-((4aR,5S,7aS)-2-amino-5-(trifluoromethyl)-4a,5,7,7a-tetrahydro-4H-furo[3,4-d][1,3]oxazin-7a-yl)-4-fluorophenyl)-5-methylpicolinamide:

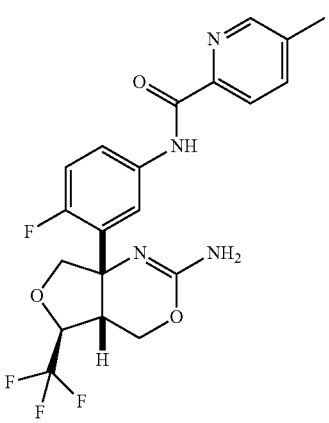

N-(3-((4aR,5S,7aS)-2-amino-5-(trifluoromethyl)-4a,5,7,7a-tetrahydro-4H-furo[3,4-d][1,3]oxazin-7a-yl)-4-fluorophenyl)-5-ethylpicolinamide:

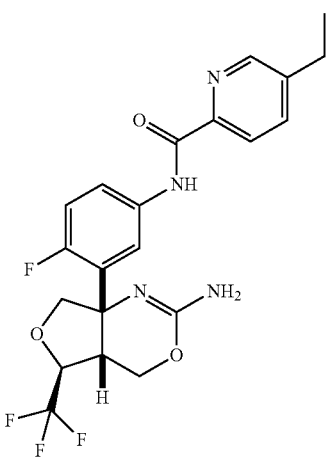

N-(3-((4aR,5S,7aS)-2-amino-5-(trifluoromethyl)-4a,5,7,7a-tetrahydro-4H-furo[3,4-d][1,3]oxazin-7a-yl)-4-fluorophenyl)-5-ethoxypyrazine-2-carboxamide:

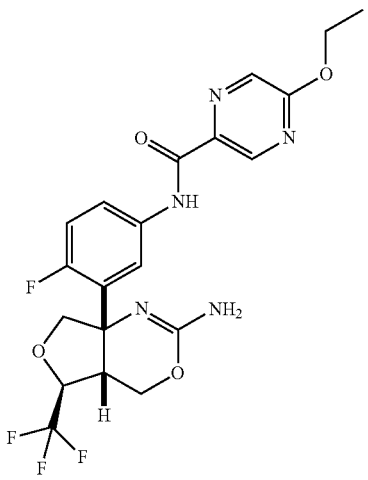

;

N-(3-((4aR,5S,7aS)-2-amino-5-(trifluoromethyl)-4a,5,7,7a-tetrahydro-4H-furo[3,4-d][1,3]oxazin-7a-yl)-4-fluorophenyl)-5-(1,1-difluoroethyl)pyrazine-2-carboxamide:

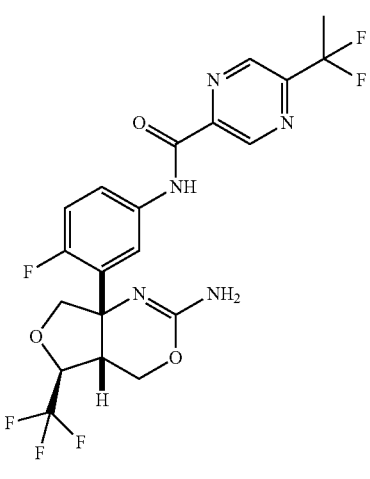

;

and
5-Difluoromethyl-pyrazine-2-carboxylic acid [3-((1S,4aS,5R,7aS)-2-amino-5-methyl-4-trifluoromethyl-4a,5-dihydro-4H-furo[3,4-d][1,3]oxazin-7a-yl)-4-fluoro-phenyl]-amide:

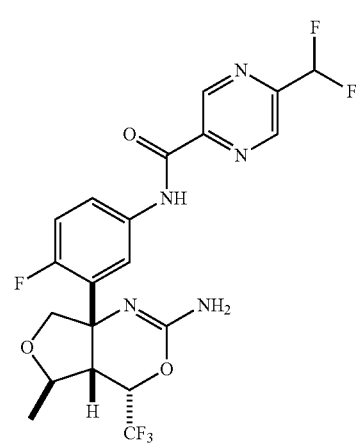

;

A preferred enantiomer of the compound of formula (I) is:

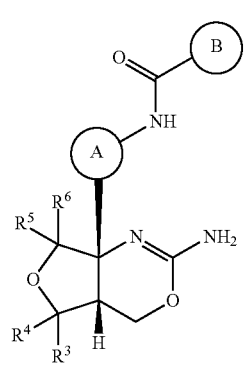

(Ii)

Next, methods for preparing the compound of the formula (I) [hereinafter referred to as compound (I); a compound represented by another formula is similarly described] or pharmaceutically acceptable salt thereof according to the present invention will be described.

The compound represented by the formula (I):

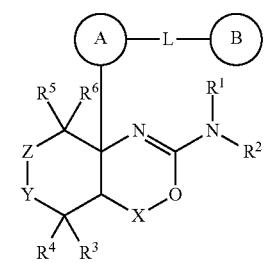

(I)

(wherein Ring A, Ring B, $R^1$, $R^2$, $R^3$, $R^4$, $R^5$, $R^6$, L, X, Y and Z are as defined above) or the intermediate thereof are synthesized by, for example, General Preparation Methods 1 to 15 as described below.

The "leaving group" in the raw material compound used in preparation of the compound (I) according to the present invention may be any leaving group used for nucleophilic substitution reaction. Preferable examples of the leaving group include a halogen atom, a $C_{1-6}$ alkylsulfonyloxy group which may be substituted with the above Substituent Group α and an arylsulfonyloxy group which may be substituted with the above Substituent Group α. Specific examples of the leaving group include a chlorine atom, a bromine atom, an iodine atom, a methanesulfonyloxy group, a trifluoromethanesulfonyloxy group and a p-toluenesulfonyloxy group.

1. General Preparation Method 1:

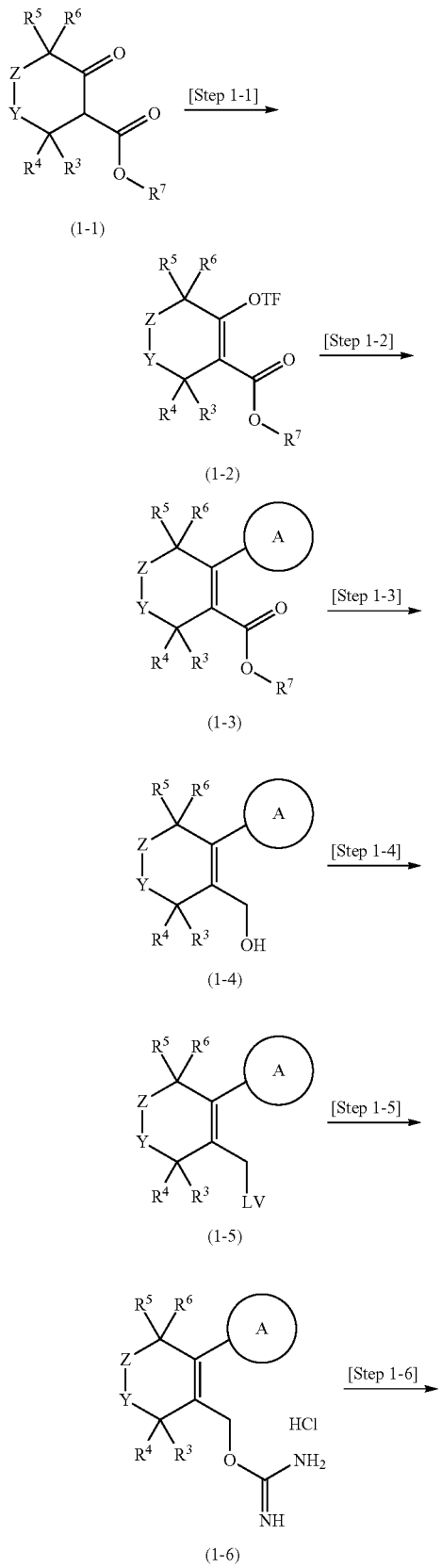

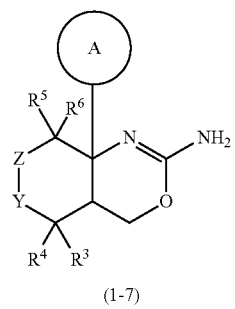

In the formula, $R^7$ represents a $C_{1-6}$ alkyl group such as a methyl group or an ethyl group, a $C_{7-12}$ aralkyl group such as a benzyl group, or the like, LV is a leaving group and represents a halogen atom (such as a chlorine atom, a bromine atom or an iodine atom), for example, or a sulfonyloxy group such as a methanesulfonyloxy group, a p-toluenesulfonyloxy group or a trifluoromethanesulfonyloxy group (represented by TfO in the formula), for example, and Ring A, $R^3$, $R^4$, $R^5$, $R^6$, Y and Z are as defined above.

General Preparation Method 1 is a method for preparing a compound (1-7) which is a synthetic intermediate of the compound (1) according to the present invention from a compound (1-1) as a raw material through multiple steps of Step 1-1 to Step 1-6.

The compound (1-1) can be a commercially available product used as is, can also be prepared from a commercially available product by a method known to a person skilled in the art, and can further be prepared by a method described in Preparation Examples among Examples.

Step 1-1:

This step is a step of obtaining a compound (1-2) by trifluoromethanesulfonylation of the compound (1-1).

The reaction in this step can be performed under the same conditions as those usually used in trifluoromethanesulfonylation reaction of a carbonyl compound (such as the conditions described in J. Org. Chem., 57, 6972-6975 (1992), Tetrahedron Letters., 40, 8133-8136 (1999) and Tetrahedron., 61, 4128-4140 (2005)).

Specifically, the compound (1-2) can be obtained by causing a base to act on the compound (1-1), and then reacting the compound with N-phenyltrifluoromethanesulfonimide or trifluoromethanesulfonic anhydride, for example. This reaction can be performed by causing one or more equivalents of a base to act on the compound (1-1) in an organic solvent such as ether, tetrahydrofuran, 1,4-dioxane, 1,2-dimethoxyethane, dichloromethane, 1,2-dichloroethane, benzene or toluene, for example. Examples of the base used include sodium hydride, LDA (lithium diisopropylamide), lithium bis(trimethylsilyl) amide, diisopropylethylamine, pyridine and 2,6-lutidine. The reaction time is not particularly limited and is usually 5 minutes to 24 hours, and preferably 5 minutes to 12 hours. The reaction temperature is usually –100° C. to room temperature, and more preferably –78° C. to room temperature.

Step 1-2:

This step is a step of obtaining a compound (1-3) by coupling reaction of the compound (1-2) using a transition metal.

This reaction can be performed under the conditions usually used in coupling reaction using a transition metal (such as Suzuki-Miyaura reaction or Stille reaction).

Examples of the reaction using an organoboron reagent as an organometallic compound include reactions in documents such as Tetrahedron: Asymmetry 16 (2005) 2, 528-539 and Org. Lett. 6 (2004) 2, 277-279. Examples of the reaction using an organotin reagent include reaction in a document such as Tetrahedron 61 (2005) 16, 4128-4140. Examples of the reaction using an organozinc reagent as an organometallic compound include reaction in a document such as Tetrahedron 61 (2005) 16, 4128-4140. The organometallic catalyst used in this reaction is not particularly limited. Preferable examples of the organometallic catalyst include tetrakis(triphenylphosphine)palladium (0), dichlorobis(triphenylphosphine)palladium (II), [1,1'-bis(diphenylphosphino)ferrocene]palladium (II) dichloride, bis(tert-butylphosphine) palladium (0), palladium (II) acetate and [1,3-bis(diphenylphosphino)propane]nickel (II). The amount of the organometallic catalyst used is about 0.001 to 0.1 equivalent with respect to the raw material. The organometallic compound is not particularly limited. Preferable examples of the organometallic compound include organotin reagents such as aryltri-n-butyltin, and organoboron reagents such as arylboronic acid. The amount of the organometallic compound used is one to five equivalents with respect to the raw material. The solvent used in this reaction is not particularly limited insofar as it does not inhibit the reaction. Preferable examples of the solvent include benzene, toluene, xylene, N,N-dimethylformamide, 1-methyl-2-pyrrolidone, tetrahydrofuran, 1,4-dioxane, acetonitrile and propionitrile. The reaction temperature is not particularly limited and is usually ice-cold temperature to solvent reflux temperature, and preferably room temperature to solvent reflux temperature, for example. The reaction time is not particularly limited and is usually 0.5 to 48 hours, and preferably 0.5 to 24 hours.

A more preferable result such as an improved yield may be achieved by carrying out this reaction in the presence of a base. Such a base is not particularly limited. Preferable examples of the base include bases such as sodium carbonate, potassium carbonate, cesium carbonate, potassium phosphate and solutions thereof, and triethylamine.

Step 1-3:

This step is a step of obtaining an alcohol compound (1-4) by subjecting the ester compound (1-3) to reduction reaction. The alcohol compound (1-4) can be obtained from the ester compound (1-3) by a method known to a person skilled in the art.

Examples of the reducing agent used in the reaction include lithium aluminum hydride, lithium borohydride and diisobutylaluminum hydride. The reaction temperature is not particularly limited and is usually −78° C. to solvent reflux temperature, and preferably −78° C. to room temperature. The solvent used in the reaction is not particularly limited insofar as it does not inhibit the reaction and allows the starting material to be dissolved therein to a certain extent. Preferable examples of the solvent include tetrahydrofuran, diethyl ether, toluene and dichloromethane.

Step 1-4:

This step is a step of obtaining a compound (1-5) by converting the hydroxyl group of the compound (1-4) to a leaving group.

Examples of the leaving group include halogen atoms (such as a chlorine atom, a bromine atom and an iodine atom) and sulfonyloxy groups such as a methanesulfonyloxy group, a p-toluenesulfonyloxy group and a trifluoromethanesulfonyloxy group.

The reaction can be performed under the same conditions as those usually used in reaction of converting a hydroxyl group to such a leaving group. When the leaving group is a halogen atom, for example, the compound (1-5) can be prepared by reacting the compound (1-4) with thionyl chloride, thionyl bromide, phosphorus tribromide or tetrahalogenomethane-triphenylphosphine, for example. The solvent used in the reaction is not particularly limited insofar as it does not inhibit the reaction and allows the starting material to be dissolved therein to a certain extent. Preferable examples of the solvent include benzene, toluene, xylene, dichloromethane and chloroform. The reaction temperature is usually −78° C. to solvent reflux temperature, and preferably ice-cold temperature to solvent reflux temperature. The reaction time is not particularly limited and is usually 5 minutes to 48 hours, and preferably 5 minutes to 12 hours.

When the leaving group is a sulfonyloxy group, the compound (1-5) can be prepared by reacting the compound (1-4) with methanesulfonyl chloride, p-toluenesulfonyl chloride or trifluoromethanesulfonic anhydride, for example.

The solvent used in the reaction is not particularly limited insofar as it does not inhibit the reaction and allows the starting material to be dissolved therein to a certain extent. Preferable examples of the solvent include tetrahydrofuran, toluene, xylene, dichloromethane, chloroform and N,N-dimethylformamide. The reaction temperature is usually −78° C. to solvent reflux temperature, and preferably −78° C. to room temperature. A favorable result such as an improved yield may be achieved by addition of a base. The base used is not particularly limited insofar as it does not inhibit the reaction. Preferable examples of the base include sodium carbonate, potassium carbonate, triethylamine, pyridine and diisopropylethylamine.

Step 1-5:

This step is a step of obtaining a compound (1-6) from the compound (1-5). The carbamimidate compound (1-6) can be obtained from the compound (1-5) by a method known to a person skilled in the art.

Specifically, the compound (1-6) can be obtained by reacting the compound (1-5) with urea in a solvent, for example. This reaction can be performed by causing one or more equivalents of urea to act on the compound (1-5) in an organic solvent such as ethanol, 1-propanol, 2-propanol, 1-butanol, tetrahydrofuran, 1,4-dioxane or N,N-dimethylformamide, for example. The reaction time is not particularly limited and is usually 5 minutes to 24 hours, and preferably 5 minutes to 12 hours. The reaction temperature is usually 0° C. to 150° C., and more preferably room temperature to 100° C.

Step 1-6:

This step is a method of obtaining the compound (1-7) by cyclizing the compound (1-6) with an acid.

This reaction is not particularly limited insofar as it does not inhibit the reaction and allows the starting material to be dissolved therein to a certain extent. For example, the reaction can be performed by causing one equivalent to a large excess of an appropriate acid to act on the compound (1-6) in the presence or absence of a solvent such as benzene, toluene or dichloromethane. Further, an acid may also be used as a solvent. Examples of the acid used include sulfuric acid, trifluoroacetic acid, methanesulfonic acid, trifluoromethanesulfonic acid and mixtures thereof. The reaction time is not particularly limited and is usually 1 to 72 hours, and preferably 1 to 48 hours. The reaction temperature is usually ice-cold temperature to solvent reflux temperature.

The amino group in the compound (1-7) can be converted to corresponding —NR$^1$R$^2$ in the formula (I), in which R$^1$ and R$^2$ are substituted, by further reacting the compound (1-7) with a corresponding halide compound or the like such as a C$_{1-6}$ alkyl halide, a C$_{1-6}$ alkylcarbonyl halide, a C$_{6-14}$ arylcarbonyl halide, a C$_{1-6}$ alkylsulfonyl halide, a C$_{6-14}$ arylsulfonyl halide, a 3- to 10-membered carbocyclic halide or a 5- to 10-membered heterocyclic halide.

2. General Preparation Method 2:

Method 2A:

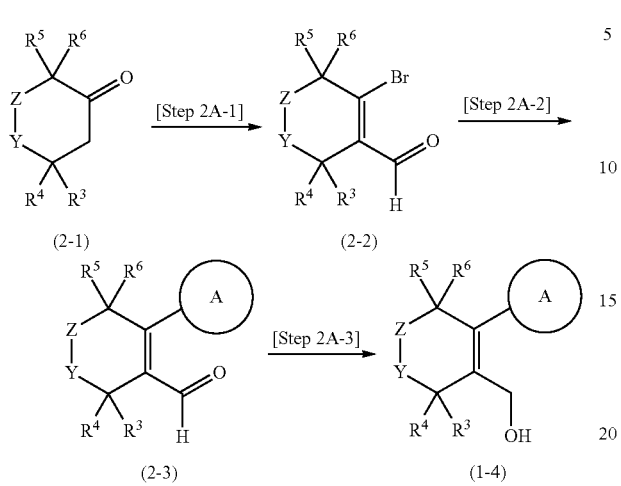

(2-1) → (2-2) → (2-3) → (1-4)

Method 2B:

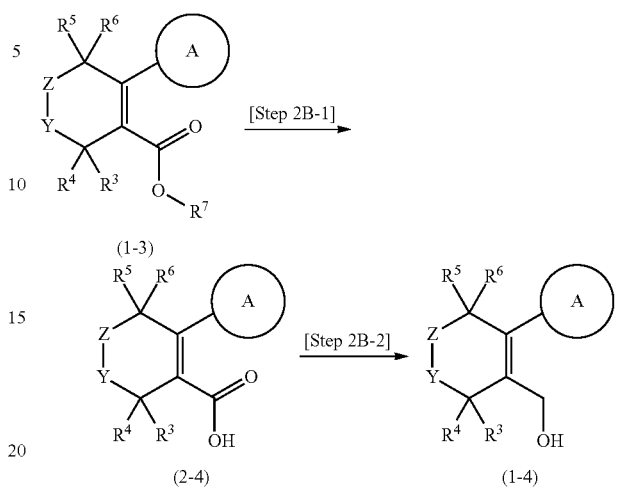

(1-3) → (2-4) → (1-4)

In the formula, Ring A, $R^3$, $R^4$, $R^5$, $R^6$, Y and Z are as defined above.

General Preparation Method 2 consists of the above Method 2A and the later-described Method 2B. Method 2A is a method for preparing a compound of the general formula (I-4) which is a synthetic intermediate of the compound (1) according to the present invention from a compound (2-1) as a raw material through multiple steps of Step 2A-1 to Step 2A-3.

The compound (2-1) can be a commercially available product used as is, can also be prepared from a commercially available product by a method known to a person skilled in the art, and can further be prepared by a method described in Preparation Examples among Examples.

Step 2A-1:

This step is a step of obtaining a compound (2-2) from the compound (2-1). This reaction can be performed under the same conditions as those usually used in reaction of synthesizing a compound (2-2) from a carbonyl compound (such as the conditions described in J. Org. Chem., 47, 3597-3607 (1982)).

Step 2A-2:

This step is a step of synthesizing a compound (2-3) from the compound (2-2) as a raw material using a method described in the above preparation method (Step 1-2).

Step 2A-3:

This step is a step of obtaining the alcohol compound (1-4) by subjecting the aldehyde compound (2-3) to reduction reaction.

The alcohol compound (1-4) can be obtained from the aldehyde compound (2-3) by a method known to a person skilled in the art. Examples of the reducing agent used in the reaction include sodium borohydride, sodium cyanoborohydride and sodium triacetoxyborohydride. The reaction temperature is not particularly limited and is usually −78° C. to solvent reflux temperature, and preferably −20° C. to room temperature. The solvent used in the reaction is not particularly limited insofar as it does not inhibit the reaction and allows the starting material to be dissolved therein to a certain extent. Preferable examples of the solvent include methanol, ethanol, tetrahydrofuran, ether, toluene and dichloromethane.

Method 2B:

In the formula, Ring A, $R^3$, $R^4$, $R^5$, $R^6$, $R^7$, Y and Z are as defined above.

As shown in the above method 2B, the compound (1-4) can also be prepared by converting a compound (1-3) to a compound (2-4) and subjecting the compound to reduction reaction.

The compound (1-3) can be prepared from a commercially available product by General Preparation Method 1, and can also be prepared by a method described in Preparation Examples among Examples.

Step 2B-1:

This step is a step of obtaining the compound (2-4) by alkaline hydrolysis of the compound (1-3).

The reaction can be performed under the same reaction conditions as those described in J. Med. Chem., 33 (9), 2621-2629 (1990), for example.

Specifically, the compound (2-4) can be obtained by adding a base such as sodium hydroxide to a solution of the compound (1-3), stirring the mixture for several hours to one day, and then treating the solution with an acid such as a citric acid solution, for example.

The solvent used in the reaction is not particularly limited insofar as it does not inhibit the reaction and allows the starting material to be dissolved therein to a certain extent. Examples of the solvent include methanol, ethanol, 2-propanol, tetrahydrofuran and 1,4-dioxane. The base used is not particularly limited and is preferably sodium hydroxide, potassium hydroxide or lithium hydroxide, for example. The amount of the base used is one equivalent to a large excess, and preferably 1 to 20 equivalents with respect to the compound (1-3). The reaction time is not particularly limited and is usually 1 to 24 hours, and preferably 1 to 6 hours. The reaction temperature is not particularly limited and is usually room temperature to solvent reflux temperature.

Step 2B-2:

This step is a step of obtaining the compound (1-4) by subjecting the compound (2-4) to reduction reaction.

The compound (1-4) can be obtained by converting the compound (2-4) to a mixed acid anhydride and then reacting the mixed acid anhydride with sodium borohydride. The mixed acid anhydride can be synthesized by a method known to a person skilled in the art. The synthesis is performed by reacting the compound (2-4) with a chloroformate such as ethyl chloroformate in the presence of a base such as triethylamine, for example. One to two equivalents of the chloroformate and the base are used with respect to the compound (2-4). The reaction temperature is −30° C. to room temperature, and preferably −20° C. to room temperature.

The step of reacting the mixed acid anhydride with a reducing agent such as sodium borohydride is performed by reaction in a solvent such as tetrahydrofuran or 1,2-dimethoxyethane or in a mixed solution of the solvent and water, for example. One equivalent to a large excess of the reducing agent such as sodium borohydride is used with respect to the mixed acid anhydride.

The reaction time is not particularly limited and is usually 0.5 to 48 hours, and preferably 0.5 to 24 hours. The reaction temperature is not particularly limited and is usually −78° C. to solvent reflux temperature, and preferably −20° C. to room temperature. The solvent used in the reaction is not particularly limited insofar as it does not inhibit the reaction and allows the starting material to be dissolved therein to a certain extent. Preferable examples of the solvent include tetrahydrofuran and ether.

3. General Preparation Method 3:

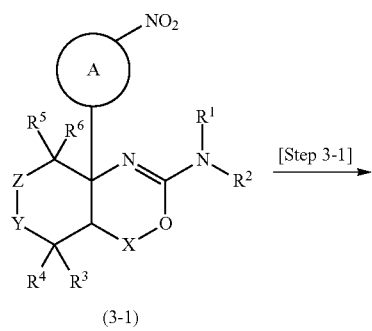

(3-1)

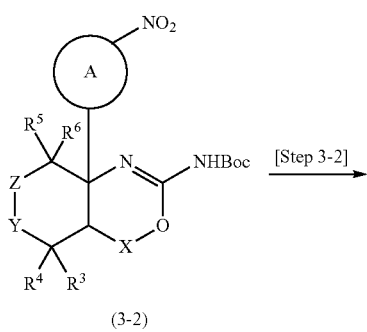

(3-2)

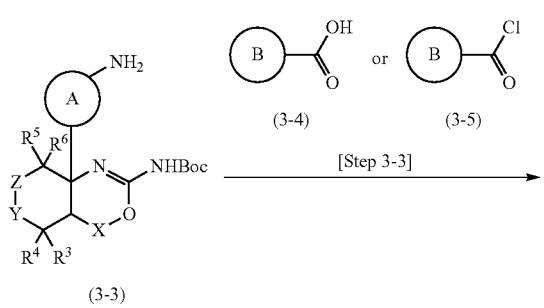

(3-3)

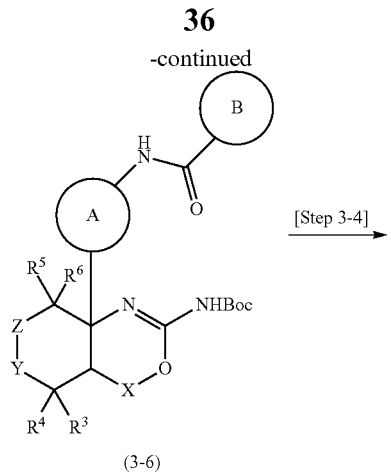

(3-6)

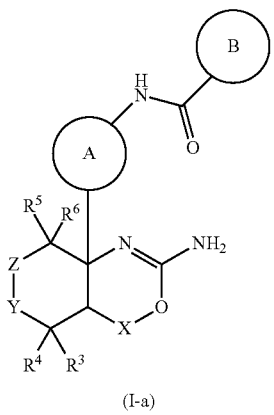

(I-a)

In the formula, Ring A, $R^1$, $R^2$, $R^3$, $R^4$, $R^5$, $R^6$, X, Y, Z and Ring B are as defined above.

General Preparation Method 3 is a method for preparing the compound of the general formula (I) according to the present invention, wherein L is —NHCO— and $R^1$ and $R^2$ are hydrogen atoms, from a compound (3-1) as a raw material through multiple steps of Step 3-1 to Step 3-4.

The compound (3-1) can be prepared from a commercially available product by the above General Preparation Method 1 or a combination of three preparation methods, General Preparation Method 1, General Preparation Method 2 and General Preparation Method 4, and can also be prepared by a method described in Preparation Examples among Examples. Compounds (3-4) and (3-5) each can be a commercially available product used as is, can also be prepared from a commercially available product by a method known to a person skilled in the art, and can further be prepared by a method described in Preparation Examples among Examples.

Step 3-1:

This step is a step of obtaining a compound (3-2) by t-butoxycarbonylation of the amino group of the compound (3-1) when $R^1$ and $R^2$ are both hydrogen.

The reaction can be performed under the same conditions as those generally used in t-butoxycarbonylation of an amino compound such as the conditions described in a document such as T. W. Green and P. G. M. Wuts, "Protective Groups in Organic Chemistry, Second Edition", John Wiley & Sons (1991), P. 327-330. The compound (3-2) can be obtained by reacting the compound (3-1) with di-tert-butyl dicarbonate using triethylamine as a base in a solvent such as tetrahydrofuran, for example.

Step 3-2:

This step is a step of obtaining a compound (3-3) from the compound (3-2).

The compound (3-3) is synthesized by reducing the nitro compound (3-2) by a synthesis method known to a person skilled in the art. Examples of the method include reduction by catalytic hydrogenation using a noble metal catalyst such as Raney nickel, palladium, ruthenium, rhodium or platinum. In this case, reduction reaction with iron under neutral conditions using ammonium chloride is preferable, for example.

Step 3-3:

This step is a step of obtaining a compound (3-6) by condensing the compound (3-3) with the compound (3-4) using a condensing agent. Alternatively, this step is a step of obtaining a compound (3-6) by condensing the compound (3-3) with the compound (3-5) by acylation reaction.

The condensation reaction of the compound (3-3) with the compound (3-4) using a condensing agent can be performed under the same conditions as those usually used and described in the following documents. Examples of the known method include those in Rosowsky, A.; Forsch, R. A.; Moran, R. G.; Freisheim, J. H.; J. Med. Chem., 34 (1), 227-234 (1991), Brzostwska, M.; Brossi, A.; Flippen-Anderson, J. L.; Heterocycles, 32 (10), 1968-1972 (1991), and Romero, D. L.; Morge, R. A.; Biles, C.; Berrios-Pena, N.; May, P. D.; Palmer, J. R.; Johnson, P. D.; Smith, H. W.; Busso, M.; Tan, C.-K.; Voorman, R. L.; Reusser, F.; Althaus, I. W.; Downey, K. M.; So, A. G.; Resnick, L.; Tarpley, W. G., Aristoff, P. A.; J. Med. Chem., 37 (7), 998-1014 (1994).

The compound (3-3) may be a free form or a salt.

The solvent in this reaction is not particularly limited insofar as it does not inhibit the reaction. Examples of the solvent include tetrahydrofuran, 1,4-dioxane, ethyl acetate, methyl acetate, dichloromethane, chloroform, N,N-dimethylformamide, toluene and xylene. Examples of the condensing agent include CDI (N,N'-carbonyldiimidazole), Bop (1H-1,2,3-benzotriazol-1-yloxy(tri(dimethylamino))phosphonium hexafluorophosphate), WSC (1-ethyl-3-(3-dimethylaminopropyl)carbodiimide hydrochloride), DCC(N,N-dicyclohexylcarbodiimide), diethylphosphoryl cyanide, PyBOP (benzotriazol-1-yloxytris(pyrrolidino)phosphonium hexafluorophosphate) and EDC.HCl (1-ethyl-3-(3-dimethylaminopropyl)carbodiimide hydrochloride). One equivalent to a large excess of the compound (3-4) is used with respect to the compound (3-3). One equivalent to a large excess of an organic base such as triethylamine may be added where necessary.

The reaction time is not particularly limited and is usually 0.5 to 48 hours, and preferably 0.5 to 24 hours. The reaction temperature varies according to the raw material used, the solvent and the like and is not particularly limited. Ice-cold temperature to solvent reflux temperature is preferable.

The compound of the formula (I) according to the present invention, wherein at least one of $R^1$ and $R^2$ is a $C_{1-6}$ alkyl group which optionally has 1 to 3 substituents selected from Substituent Group α, a $C_{1-6}$ alkylcarbonyl group which optionally has 1 to 3 substituents selected from Substituent Group α, a $C_{6-14}$ arylcarbonyl group which optionally has 1 to 3 substituents selected from Substituent Group α, a $C_{1-6}$ alkylsulfonyl group which optionally has 1 to 3 substituents selected from Substituent Group α, a $C_{6-14}$ arylsulfonyl group which optionally has 1 to 3 substituents selected from Substituent Group α, a 3- to 10-membered carbocyclic group which optionally has 1 to 3 substituents selected from Substituent Group α or a 5- to 10-membered heterocyclic group which optionally has 1 to 3 substituents selected from Substituent Group α, can be obtained by further reacting the compound (I-a) obtained in General Preparation Method 3 with a corresponding halide compound such as a $C_{1-6}$ alkyl halide.

Alternatively, —NHCO— of L in the compound (I-a) of the present invention can be converted to —NR$^e$CO— (wherein R$^e$ is a $C_{1-6}$ alkyl group which optionally has 1 to 3 substituents selected from Substituent Group α) by further reacting the compound (I-a) obtained in General Preparation Method 3 with a corresponding halide compound such as a $C_{1-6}$ alkyl halide.

The compound of the formula (I) according to the present invention, wherein L is —NR$^e$SO$_2$—, can be obtained using a corresponding sulfonyl halide compound in place of the compound (3-4) or (3-5) used in General Preparation Method 3.

In General Preparation Method 3, the compound (3-6) can also be prepared from the compound (3-3) and the compound (3-4) by a method described in the following alternative method (1) or (2).

Alternative Method (1):

The compound (3-6) can be obtained by converting the compound (3-4) to a mixed acid anhydride and then reacting the mixed acid anhydride with the compound (3-3). The mixed acid anhydride can be synthesized by a means known to a person skilled in the art. The synthesis is performed by reacting the compound (3-4) with a chloroformate such as ethyl chloroformate in the presence of a base such as triethylamine, for example. One to two equivalents of the chloroformate and the base are used with respect to the compound (3-4). The reaction temperature is −30° C. to room temperature, and preferably −20° C. to room temperature.

The step of condensing the mixed acid anhydride with the compound (3-3) is performed by reacting the mixed acid anhydride with the compound (3-3) in a solvent such as dichloromethane, tetrahydrofuran or N,N-dimethylformamide, for example. One equivalent to a large excess of the compound (3-3) is used with respect to the mixed acid anhydride.

The reaction time is not particularly limited and is usually 0.5 to 48 hours, and preferably 0.5 to 12 hours. The reaction temperature is −20° C. to 50° C., and preferably −20° C. to room temperature.

Alternative Method (2):

The compound (3-6) can be obtained by converting the compound (3-4) to an active ester and then reacting the active ester with the compound (3-3). The step of obtaining the active ester is performed by reacting the compound (3-4) with an active ester synthesis reagent in a solvent such as 1,4-dioxane, tetrahydrofuran or N,N-dimethylformamide in the presence of a condensing agent such as DCC, for example. Examples of the active ester synthesis reagent include N-hydroxysuccinimide. One to 1.5 equivalents of the active ester synthesis reagent and the condensing agent are used with respect to the compound (3-4). The reaction time is not particularly limited and is usually 0.5 to 48 hours, and preferably 0.5 to 24 hours.

The reaction temperature is −20° C. to 50° C., and preferably −20° C. to room temperature.

The step of condensing the active ester with the compound (3-3) is performed by reacting the active ester with the compound (3-3) in a solvent such as dichloromethane, tetrahydrofuran or N,N-dimethylformamide, for example. One equivalent to a large excess of the compound (3-3) is used with respect to the active ester. The reaction time is not particularly limited and is usually 0.5 to 48 hours, and preferably 0.5 to 24 hours. The reaction temperature is −20° C. to 50° C., and preferably −20° C. to room temperature.

In this acylation reaction, the compound (3-6) can be obtained from the compounds (3-3) and (3-5) by a method known to a person skilled in the art.

Examples of the base used in the reaction include triethylamine, pyridine, potassium carbonate and diisopropylethylamine. The reaction temperature is not particularly limited and is usually −78° C. to solvent reflux temperature, and preferably −20° C. to room temperature. The solvent used in the reaction is not particularly limited insofar as it does not inhibit the reaction and allows the starting material to be dissolved therein to a certain extent. Preferable examples of the solvent include tetrahydrofuran, ether, toluene and dichloromethane.

Step 3-4:

This step is a step of obtaining the compound (I-a) by deprotection reaction of the t-butoxycarbonyl group of the compound (3-6).

The reaction can be performed under the same conditions as those generally used in deprotection reaction of a t-butoxycarbonyl group such as the conditions described in a document such as T. W. Green and P. G. M. Wuts, "Protective Groups in Organic Chemistry, Second Edition", John Wiley & Sons (1991), P. 327-330. The compound (I-a) can be obtained by reacting trifluoroacetic acid with the compound (3-6) in a solvent such as dichloromethane, for example.

4. General Preparation Method 4:

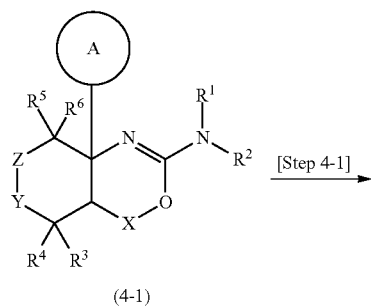

(4-1)

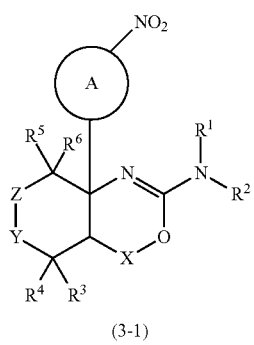

(3-1)

In the formula, Ring A, $R^1$, $R^2$, $R^3$, $R^4$, $R^5$, $R^6$, X, Y and Z are as defined above.

General Preparation Method 4 is a method for preparing a compound of the general formula (3-1) which is a synthetic intermediate of the compound according to the present invention and is used in General Preparation Method 3 from a compound (4-1) as a raw material through Step 4-1.

The compound (4-1) can be prepared from a commercially available product by General Preparation Method 1, General Preparation Method 5 or a combination of General Preparation Method 1 and General Preparation Method 2, and can also be prepared by a method described in Preparation Examples among Examples.

Step 4-1:

This step is a step of obtaining the compound (3-1) by nitration reaction of the compound (4-1). In this nitration reaction, the compound (3-1) can be obtained from the compound (4-1) by a method known to a person skilled in the art. Examples of the nitrating agent used in the reaction include potassium nitrate/concentrated sulfuric acid, fuming nitric acid/acetic anhydride, concentrated nitric acid/concentrated sulfuric acid, concentrated nitric acid and concentrated nitric acid/concentrated sulfuric acid in TFA. The reaction temperature is not particularly limited and is usually −20° C. to room temperature.

5. General Preparation Method 5:

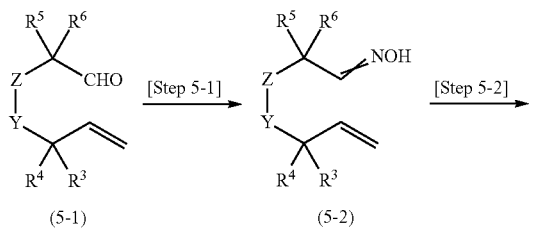

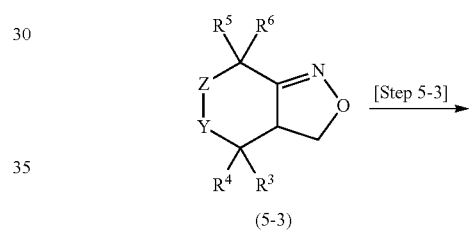

(5-3)

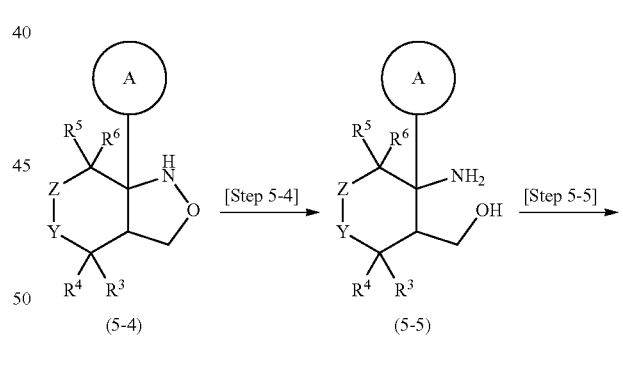

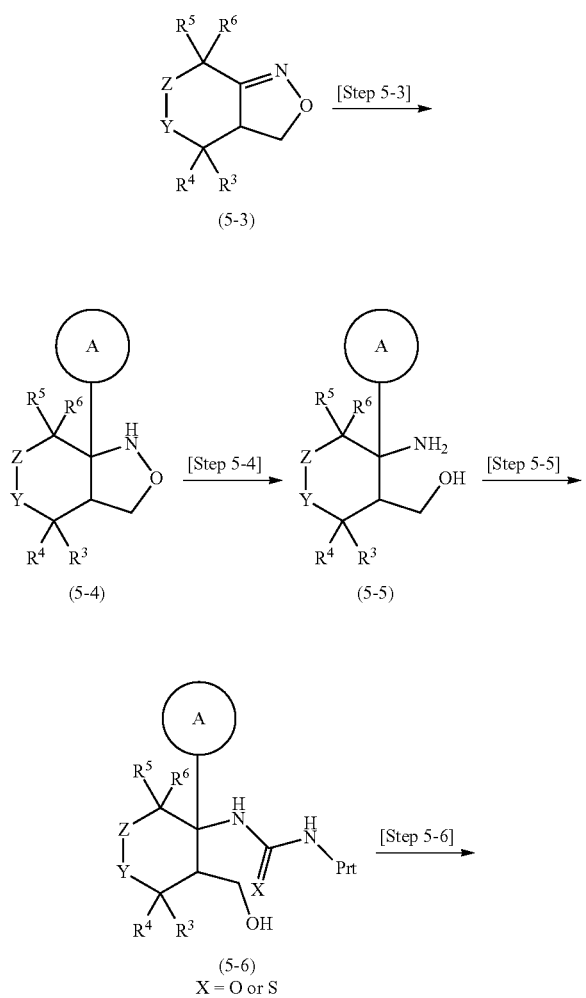

(5-6)
X = O or S

-continued

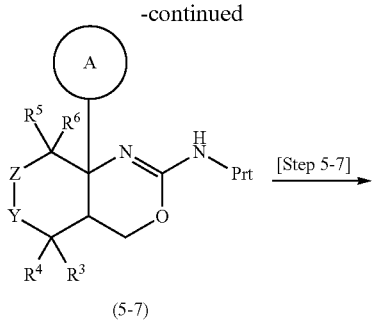

(5-7)

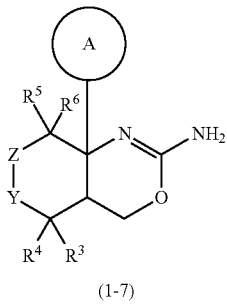

(1-7)

In the formula, Prt represents a protecting group such as a benzoyl group, an acetyl group or a 8-fluorenemethyloxycarbonyl group (Fmoc group), and Ring A, $R^3$, $R^4$, $R^5$, $R^6$, Y and Z are as defined above.

General Preparation Method 5 is a method for preparing a compound (1-7) which is a synthetic intermediate of the compound (1) according to the present invention from a compound (5-1) as a raw material through multiple steps of Step 5-1 to Step 5-7.

The compound (5-1) can be prepared from a commercially available product by the later-described General Preparation Method 6 or 7, can also be prepared from a commercially available product by a method known to a person skilled in the art, and can further be prepared by a method described in Preparation Examples among Examples.

Step 5-1:

This step is a step of obtaining a compound (5-2) by oximation of the compound (5-1).

The reaction in this step can be performed under the same conditions as those usually used in oximation reaction of a carbonyl compound such as the conditions described in Org. Lett. 9 (2007) 5, 753-756, Tetrahedron: Asymmetry 5 (1994) 6, 1018-1028 and Tetrahedron 54 (1998) 22, 5868-5882.

Specifically, the compound (5-2) can be obtained by reacting the compound (5-1) with hydroxylamine or a hydroxylamine salt (such as hydroxylamine hydrochloride or hydroxylamine sulfate) in the presence of a base or in the absence of a base, for example.

The solvent used in this reaction is not particularly limited insofar as it does not inhibit the reaction. Preferable examples of the solvent include organic solvents such as ethanol, methanol, tetrahydrofuran, 1,4-dioxane, 1,2-dimethoxyethane and dichloromethane, and mixtures of these solvents and water. Examples of the base used include sodium acetate, pyridine, sodium hydroxide, cesium hydroxide, barium hydroxide and 2,6-lutidine. The reaction time is not particularly limited and is usually 5 minutes to 24 hours, and preferably 5 minutes to 12 hours. The reaction temperature is usually −20° C. to solvent reflux temperature, and more preferably 0° C. to solvent reflux temperature.

Step 5-2:

This step is a step of obtaining a compound (5-3) by converting the compound (5-2) to a nitrile oxide derivative and performing 1,3-dipolar cycloaddition reaction with the olefin moiety in the same molecule.

The reaction in this step can be performed under the same conditions as those usually used in 1,3-dipolar cycloaddition reaction such as the conditions described in a document such as Org. Lett. 9 (2007) 5, 753-756, Tetrahedron: Asymmetry 5 (1994) 6, 1018-1028 and Tetrahedron 54 (1998) 22, 5868-5882. Examples of the reagent for converting the oxime compound to the nitrile oxide include N-chlorosuccinimide and sodium hypochlorite. The solvent used in this reaction is not particularly limited insofar as it does not inhibit the reaction. Preferable examples of the solvent include dichloromethane, chloroform, benzene, toluene, xylene, N,N-dimethylformamide, tetrahydrofuran and 1,4-dioxane. The reaction temperature is not particularly limited and is usually ice-cold temperature to solvent reflux temperature. The reaction time is not particularly limited and is usually 0.5 to 48 hours, and preferably 0.5 to 24 hours.

A more preferable result such as an improved yield may be achieved by carrying out this reaction in the presence of a base. Such a base is not particularly limited. Examples of the base include bases such as sodium carbonate, potassium carbonate, cesium carbonate, potassium phosphate and solutions thereof, and triethylamine and pyridine.

Step 5-3:

This step is a step of obtaining a compound (5-4) by addition reaction of an aryllithium reagent (including heterocyclic) or a Grignard reagent (including heterocyclic) with the compound (5-3).

The reaction in this step can be performed under the same conditions as those described in J. Am. Chem. Soc. 2005, 127, 5376-5383, Bull. Chem. Soc. Jpn., 66, 2730-2737 (1993) and SYNLETT. 2004, No. 8, pp 1408-1413, for example.

The aryllithium reagent (including heterocyclic) or the Grignard reagent (including heterocyclic) can be prepared by a method known to a person skilled in the art. Specifically, a corresponding aryl (including heterocyclic) lithium reagent or aryl (including heterocyclic) magnesium reagent can be prepared by halogen-metal exchange between an aryl halide compound and a commercially available organometallic reagent such as an alkyllithium reagent such as n-, sec- or tert-butyllithium or a Grignard reagent such as isopropylmagnesium bromide, or metallic magnesium, for example.

The solvent used in this step varies according to the starting material and the reagent used, and is not particularly limited insofar as it does not inhibit the reaction, allows the starting material to be dissolved therein to a certain extent, and is always inert during the reaction. Preferable examples of the solvent include organic solvents such as diethyl ether, tetrahydrofuran, 1,4-dioxane, 1,2-dimethoxyethane, benzene and toluene, and mixed solvents thereof. The reaction time is not particularly limited and is usually 0.1 to 48 hours, and preferably 0.1 to 12 hours. The reaction temperature varies according to the starting material, the reagent used and the like, and is preferably maintained to be low, for example, at −78° C. to minimize formation of a by-product.

Favorable results such as an improved yield and a reduced reaction time may be achieved by addition of TMEDA (tetramethylethylenediamine), HMPA (hexamethylphosphoramide) or a Lewis acid such as a boron trifluoride-diethyl ether complex ($BF_3.OEt_2$) as an additive, for example.

Step 5-4:

This step is a step of obtaining a compound (5-5) by subjecting the compound (5-4) to reductive cleavage reaction of the N—O bond.

The reductive cleavage reaction of the N—O bond can be performed under the conditions using zinc-acetic acid, a metal catalyst such as hydrogen-platinum oxide, or lithium aluminum hydride, for example.

The reaction using zinc such as zinc-acetic acid can be performed under the same conditions as those described in J. Org. Chem. 2003, 68, 1207-1215 and Org. Lett. 7 (2005) 25, 5741-5742, for example. Examples of the acid used include acetic acid, formic acid and hydrochloric acid. The solvent used in the reaction is not particularly limited insofar as it does not inhibit the reaction and allows the starting material to be dissolved therein to a certain extent. Examples of the solvent include methanol, ethanol, 1,4-dioxane, THF and water. The above acid may also be used as a solvent. The reaction temperature is usually −20° C. to solvent reflux temperature, and preferably ice-cold temperature to solvent reflux temperature. The reaction time is not particularly limited and is usually 5 minutes to 48 hours, and preferably 5 minutes to 24 hours.

The reaction using a metal catalyst such as hydrogen-platinum oxide can be performed under the same conditions as those described in Tetrahedron: Asymmetry 5 (1994) 6, 1018-1028 and Tetrahedron, Vol. 53, No. 16, pp 5752-5746, 1997, for example. The compound (5-5) can be obtained by hydrogenating the compound (5-4) using platinum oxide as a catalyst in a solvent such as methanol, for example.

The reaction using lithium aluminum hydride can be performed under the same conditions as those described in Bull. Chem. Soc. Jpn., 66, 2730-2737 (1993), for example. The compound (5-5) can be obtained by reducing the compound (5-4) using lithium aluminum hydride in a solvent such as ether, for example.

Step 5-5:

This step is a step of obtaining a compound (5-6) from the compound (5-5). The urea/thiourea derivative (5-6) can be obtained from the compound (5-5) by a method known to a person skilled in the art.

When the protecting group is a benzoyl group, the compound (5-6) can be obtained in this step by reacting the compound (5-5) with benzoyl isocyanate/isothiocyanate in a solvent such as dichloromethane or toluene. This reaction can be performed under the same conditions as those described in J. Med. Chem. 1990, 33, 2393-2407, for example. The solvent used in the reaction is not particularly limited insofar as it does not inhibit the reaction and allows the starting material to be dissolved therein to a certain extent. Examples of the solvent include dichloromethane, chloroform, toluene, methanol, ethanol, 1,4-dioxane and THF. The reaction temperature is usually −20° C. to solvent reflux temperature, and preferably ice-cold temperature to solvent reflux temperature. The reaction time is not particularly limited and is usually 5 minutes to 48 hours, and preferably 5 minutes to 24 hours.

When the protecting group is a 8-fluorenemethyloxycarbonyl group (Fmoc group), the compound (5-6) can be obtained in this step by reacting the compound (5-5) with fluorenemethyloxycarbonyl isocyanate/isothiocyanate (which can be prepared according to J. Am. Chem. Soc. 2000, 122, 5401-5402) in a solvent such as dichloromethane or toluene. This reaction can be performed under the same conditions as those described in J. Am. Chem. Soc. 2003, 125, 15796-15806. The solvent used in the reaction is not particularly limited insofar as it does not inhibit the reaction and allows the starting material to be dissolved therein to a certain extent. Examples of the solvent include dichloromethane, chloroform, toluene, methanol, ethanol, 1,4-dioxane and THF. The reaction temperature is usually −20° C. to solvent reflux temperature, and preferably ice-cold temperature to solvent reflux temperature. The reaction time is not particularly limited and is usually 5 minutes to 48 hours, and preferably 5 minutes to 24 hours.

Step 5-6:

This step is a method of obtaining a compound (5-7) by cyclizing the compound (5-6).

In this reaction, the compound (5-6) can be cyclized under various conditions to obtain the compound (5-7) by selecting a protecting group of the compound (5-6).

When the protecting group is benzoyl and X=S, for example, the compound (5-7) can be obtained in this reaction by heating the compound (5-6) in a solvent such as ethanol in the presence of a dehydrating agent such as N,N' dicyclohexylcarbodiimide, for example. The reaction time is not particularly limited and is usually 2 to 24 hours, preferably 8 to 12 hours. The reaction temperature is usually 80° C. to reflux. When the protecting group is an Fmoc group or a benzoyl group and X=O, for example, the compound (5-7) can be obtained in this reaction by heating the compound (5-6) in a solvent such as methanol in the presence of an acid such as concentrated hydrochloric acid, for example. The solvent used in the reaction is not particularly limited insofar as it does not inhibit the reaction and allows the starting material to be dissolved therein to a certain extent. Examples of the solvent include solvents such as methanol, ethanol, 1-propanol and water, mixed solvents thereof, and acids used as a solvent. The reaction can be performed by causing one equivalent to a large excess of an appropriate acid to act in the presence or absence of such a solvent. Examples of the acid used include concentrated hydrochloric acid, hydrobromic acid, sulfuric acid, trifluoroacetic acid, methanesulfonic acid, trifluoromethanesulfonic acid and mixtures thereof. The reaction time is not particularly limited and is usually 0.5 to 72 hours, and preferably 0.5 to 24 hours. The reaction temperature is usually ice-cold temperature to solvent reflux temperature.

When the protecting group is an Fmoc group or a benzoyl group, the compound (5-7) can be obtained by an alternative method of reacting the compound (5-6) with trifluoromethanesulfonic anhydride in a solvent such as dichloromethane in the presence of a base such as pyridine. The solvent used in the reaction is not particularly limited insofar as it does not inhibit the reaction and allows the starting material to be dissolved therein to a certain extent. Examples of the solvent include solvents such as dichloromethane, chloroform, 1,2-dichloroethane, THF, 1,2-dimethoxyethane and toluene, and mixed solvents thereof. The reaction can be performed using 1 to 20 equivalents of an appropriate base in such a solvent. Examples of the base used include pyridine, 2,6-lutidine, sodium carbonate, potassium carbonate and mixtures thereof. The reaction time is not particularly limited and is usually 0.5 to 24 hours, and preferably 0.5 to 12 hours. The reaction temperature is usually −78° C. to room temperature. Alternatively, when X=O, the cyclisation may be carried out using thionyl chloride in a solvent such as chloroform. It will be appreciated by those skilled in the art that when X=S, the transformation of (5-6) to (5-7) may be accomplished under a range of conditions, for example by treatment of (5-6, where X=S) with N,N'-dicyclohexylcarbodiimide in a solvent such as ethanol. These reactions can be performed under the same conditions as those described in Organic Preparations and Procedures International, 1988, 20, 73-82, for example.

When the protecting group is a benzoyl group and X=O, the compound (5-7) can be obtained by an alternative method 2 of reacting the compound (5-6) with triphenylphosphine and carbon tetrabromide (or bromine) in a solvent such as dichloromethane. The reaction conditions are the same as those of bromination of a primary alcohol which are known to a person skilled in the art.

Step 5-7:

This step is a method of obtaining the compound (1-7) by deprotecting the protecting group of the compound (5-7). The compound (1-7) can be obtained under deprotection conditions known to a person skilled in the art.

When the protecting group is an Fmoc group, for example, the compound (1-7) can be obtained under the same conditions as those generally used in deprotection of a protecting group of an amine compound (such as the conditions described in a document such as T. W. Green and P. G. M. Wuts, "Protective Groups in Organic Chemistry, Third Edition", John Wiley & Sons, p. 506-507 and J. Org. Chem. 1998, 63, 196-200). In this reaction, the compound (1-7) can be obtained by reacting the compound (5-7) with an excess of an amine such as pyrrolidine in a solvent such as acetonitrile, for example. The solvent used in the reaction is not particularly limited insofar as it does not inhibit the reaction and allows the starting material to be dissolved therein to a certain extent. Examples of the solvent include dichloromethane, THF and acetonitrile. The reaction can be performed by causing one equivalent to a large excess of an appropriate base to act in the presence of such a solvent. Examples of the base used include piperidine, morpholine, pyrrolidine, TBAF and DBU. The reaction time is not particularly limited and is usually 0.5 to 72 hours, and preferably 0.5 to 24 hours. The reaction temperature is usually ice-cold temperature to solvent reflux temperature.

Favorable results such as an improved yield and a reduced reaction time may be achieved by addition of a thiol compound such as 1-octanethiol as an additive, for example.

When the protecting group is a benzoyl group, the compound (1-7) can be obtained in this reaction by heating the compound (5-7) in a solvent such as methanol in the presence of a base such as DBU, for example. This reaction can be performed under the same conditions as those described in Synth. Commun. 32 (2), 265-272 (2002), for example. The solvent used in the reaction is not particularly limited insofar as it does not inhibit the reaction and allows the starting material to be dissolved therein to a certain extent. Examples of the solvent include solvents such as methanol, ethanol and 1-propanol. The reaction can be performed using 1 to 20 equivalents of an appropriate base in such a solvent. Examples of the base used include DBU. The reaction time is not particularly limited and is usually 0.5 to 24 hours, and preferably 0.5 to 12 hours. The reaction temperature is usually room temperature to solvent reflux temperature.

6. General Preparation Method 6:

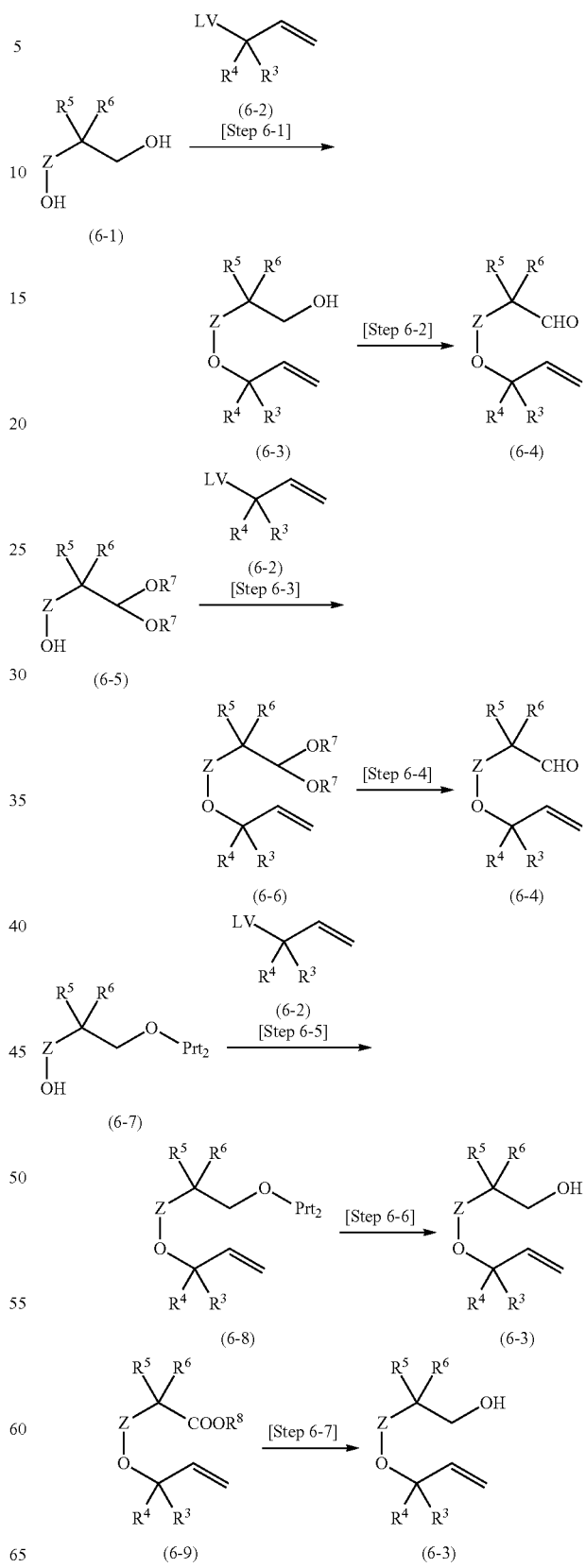

In the formula, Prt$_2$ represents a primary hydroxyl protecting group, R$^8$ represents a C$_{1-6}$ alkyl group, and Z, R$^3$, R$^4$, R$^5$, R$^6$, R$^7$ and LV are as defined above.

General Preparation Method 6 is a method for preparing a compound (6-4) which is a compound (5-1) as a starting material for General Preparation Method 5, wherein Y is an oxygen atom.

Compounds (6-1), (6-2), (6-5), (6-7) and (6-9) each can be a commercially available product used as is, can also be prepared from a commercially available product by a method known to a person skilled in the art, and can further be prepared by a method described in Preparation Examples among Examples.

Step 6-1:

This step is a step of obtaining a compound (6-3) by reaction of the compound (6-1) with the compound (6-2).

This reaction can be performed under the same conditions as those usually used in O-alkylation reaction of an alcohol compound (such as the conditions described in Tetrahedron Lett. 46 (2005) 45, 7751-7755). In this reaction, the compound (6-3) can be obtained by adding a base such as sodium hydride to a solution of the compound (6-1) in THF to prepare an alkoxide, and then reacting the alkoxide with the compound (6-2), for example. The solvent used in the reaction is not particularly limited insofar as it does not inhibit the reaction and allows the starting material to be dissolved therein to a certain extent. Examples of the solvent include solvents such as THF, DMF and dimethyl sulfoxide. The reaction can be performed by causing 1 to 3 equivalents of an appropriate base to act in the presence of such a solvent. Examples of the base used include sodium hydride, potassium hydride and t-butoxypotassium. The reaction time is not particularly limited and is usually 0.5 to 72 hours, and preferably 0.5 to 12 hours. The reaction temperature is usually −20° C. to 50° C.

A more preferable result such as an improved yield may be achieved by adding a salt such as tetrabutylammonium iodide in this reaction.

Step 6-2:

This step is a step of obtaining an aldehyde compound (6-4) by subjecting the alcohol compound (6-3) to oxidation reaction. The aldehyde compound can be obtained from the alcohol compound by a method known to a person skilled in the art.

Examples of the known oxidation method used in the reaction include Swern oxidation, Corey-Kim oxidation, Moffatt oxidation, PCC oxidation, PDC oxidation, Dess-Martin oxidation, SO$_3$-pyridine oxidation and TEMPO oxidation.

The solvent used in the reaction is not particularly limited insofar as it does not inhibit the reaction and allows the starting material to be dissolved therein to a certain extent. Examples of the solvent include dimethyl sulfoxide, tetrahydrofuran, toluene, dichloromethane and chloroform.

The reaction temperature is not particularly limited and is usually −78° C. to solvent reflux temperature, and preferably −78° C. to room temperature. The reaction time is not particularly limited and is usually 0.5 to 48 hours, and preferably 0.5 to 24 hours.

Step 6-3:

This step is a step of synthesizing a compound (6-6) from the compound (6-5) as a raw material using a method described in the above preparation method (Step 6-1).

Step 6-4:

This step is a step of obtaining the compound (6-4) by deprotecting the acetal group of the compound (6-6).

This reaction can be performed under the same conditions as those generally used in deprotection of an aldehyde group such as the conditions described in a document such as T. W. Green and P. G. M. Wuts, "Protective Groups in Organic Chemistry, Third Edition", John Wiley & Sons, P. 293-329.

Step 6-5:

This step is a step of synthesizing a compound (6-8) from the compound (6-7) as a raw material using a method described in the above preparation method (Step 6-1).

Step 6-6:

This step is a step of obtaining the compound (6-3) by deprotecting the hydroxyl protecting group of the compound (6-8). The hydroxyl protecting group used in this step is not particularly limited.

This reaction can be performed under the same conditions as those generally used in deprotection of an alcohol protecting group such as the conditions described in a document such as T. W. Green and P. G. M. Wuts, "Protective Groups in Organic Chemistry, Third Edition", John Wiley & Sons, P. 17-245.

Step 6-7:

This step is a step of synthesizing the compound (6-3) from the compound (6-9) as a raw material using a method described in the above preparation method ((Step 1-3) or (Steps 2B-1 and 2)).

7. General Preparation Method 7:

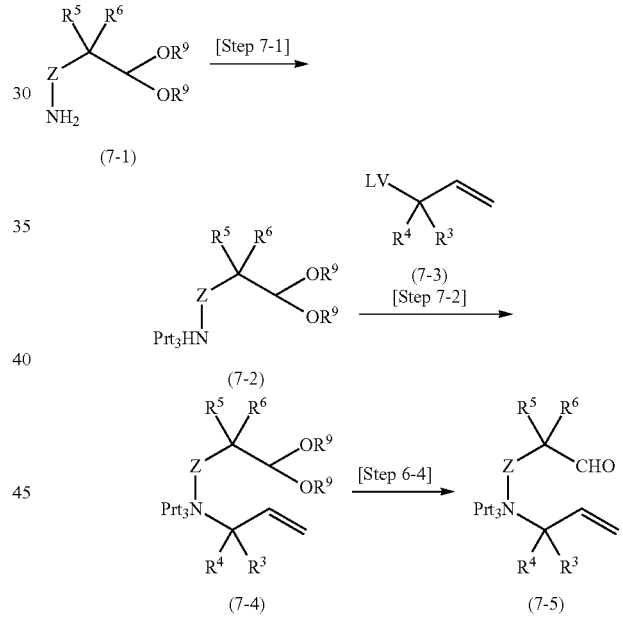

In the formula, R$^9$ represents a C$_{1-6}$ alkyl group, or two R$^9$ together may form a ring, Prt$_3$ represents a protecting group such as a 2,4-dimethoxybenzyl group, and Z, R$^3$, R$^4$, R$^5$, R$^6$, Z and LV are as defined above.

General Preparation Method 7 is a method for preparing a compound (7-5) which is a compound (5-1) as a starting material for General Preparation Method 5, wherein Y is a nitrogen atom.

Compounds (7-1) and (7-3) each can be a commercially available product used as is, can also be prepared from a commercially available product by a method known to a person skilled in the art, and can further be prepared by a method described in Preparation Examples among Examples.

Step 7-1:

This step is a step of obtaining a compound (7-2) by protecting the amino group of the compound (7-1).

49

This reaction can be performed under the same conditions as those generally used in protection of an amino group such as the conditions described in a document such as T. W. Green and P. G. M. Wuts, "Protective Groups in Organic Chemistry, Third Edition", John Wiley & Sons, P. 494-572 and J. Med. Chem. 2007, 50, 5493-5508.

Step 7-2:

This step is a step of obtaining a compound (7-4) by N-alkylation reaction of the compound (7-2) with the compound (7-3).

This reaction can be performed under the same conditions as those usually used in N-alkylation reaction of a compound (7-2) (such as the conditions described in J. Med. Chem. 2007, 50, 5493-5508). In this reaction, the compound (7-4) can be obtained by adding a base such as powdery sodium hydroxide to a solution of the compound (7-2) in toluene, and then reacting the mixture with the compound (7-3), for example. The solvent used in the reaction is not particularly limited insofar as it does not inhibit the reaction and allows the starting material to be dissolved therein to a certain extent. Examples of the solvent include solvents such as toluene, THF, DMF and dimethyl sulfoxide. The reaction can be performed by causing 1 to 5 equivalents of an appropriate base to act in the presence of such a solvent. Examples of the base used include sodium hydroxide, potassium hydroxide, sodium hydride, potassium hydride and t-butoxypotassium. The reaction time is not particularly limited and is usually 0.5 to 72 hours, and preferably 0.5 to 24 hours. The reaction temperature is usually −20° C. to 100° C.

A more preferable result such as an improved yield may be achieved by adding a salt such as tetrabutylammonium iodide in this reaction.

Step 7-3:

This step is a step of obtaining the compound (7-5) by deprotecting the acetal group of the compound (7-4).

This reaction can be performed under the same conditions as those generally used in deprotection of an aldehyde group such as the conditions described in a document such as T. W. Green and P. G. M. Wuts, "Protective Groups in Organic Chemistry, Third Edition", John Wiley & Sons, P. 293-329.

8. General Preparation Method 8:

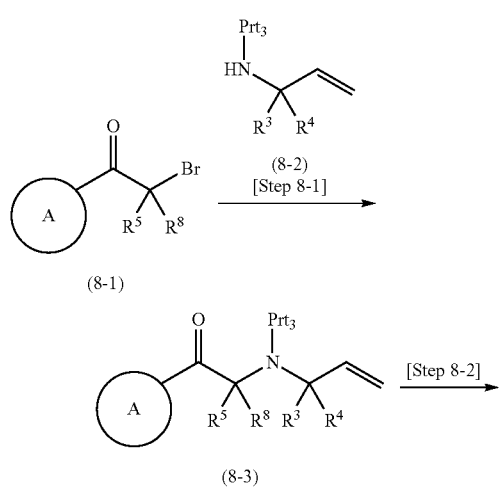

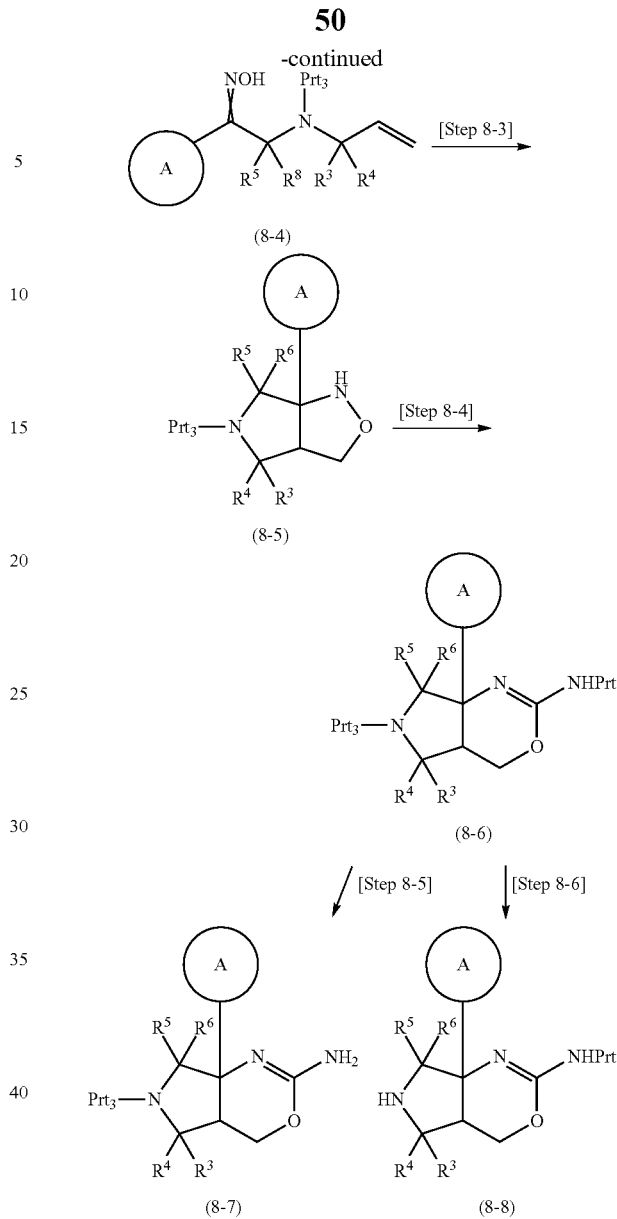

In the formula, Prt represents a protecting group such as a benzoyl group, an acetyl group or a 8-fluorenemethyloxycarbonyl group (Fmoc group), $Prt_3$ represents a protecting group such as a 2,4-dimethoxybenzyl group, and Ring A, $R^3$, $R^4$, $R^5$ and $R^6$ are as defined above.

General Preparation Method 8 is steps of the method for preparing compounds of the general formulas (8-7) and (8-8) which are synthetic intermediates of the compound (1) according to the present invention in General Preparation Method 5, wherein Y is a nitrogen atom and Z is a single bond. These compounds can be prepared from a compound (8-1) as a raw material by the steps shown above.

The compound (8-1) can be a commercially available product used as is, can also be prepared from a commercially available product by a method known to a person skilled in the art, and can further be prepared by a method described in Preparation Examples among Examples. A compound (8-2) can be prepared from a commercially available product by a method known to a person skilled in the art, and can further be prepared by a method described in Preparation Examples among Examples.

Step 8-1:

This step is a step of obtaining a compound (8-3) by reaction of the compound (8-1) with the compound (8-2). This reaction can be performed under the same conditions as those usually used in N-alkylation reaction of an amino compound (such as the conditions described in J. Med. Chem. 2002, 45, 3794-3804 and J. Med. Chem. 2000, 43, 3808-3812). In this reaction, the compound (8-3) can be obtained by reacting the compound (8-1) with the compound (8-2) in a solvent such as dichloromethane in the presence of a base such as N,N-diisopropylethylamine, for example. The solvent used in the reaction is not particularly limited insofar as it does not inhibit the reaction and allows the starting material to be dissolved therein to a certain extent. Examples of the solvent include dichloromethane, THF, acetonitrile and DMF. The reaction can be performed by causing 1 to 10 equivalents of an appropriate base to act in such a solvent. Examples of the base used include N,N-diisopropylethylamine, triethylamine, sodium carbonate and potassium carbonate. The reaction time is not particularly limited and is usually 0.5 to 72 hours, and preferably 0.5 to 12 hours. The reaction temperature is usually ice-cold temperature to 50° C.

Step 8-2:

This step is a step of obtaining a compound (8-4) by oximation of the compound (8-3).

The reaction in this step can be performed under the same conditions as those usually used in oximation reaction of a carbonyl compound such as the conditions described in J. Med. Chem. 2002, 45, 3794-3804 and J. Med. Chem. 2000, 43, 3808-3812.

Specifically, the compound (8-4) can be obtained by reacting the compound (8-3) with hydroxylamine or a hydroxylamine salt (such as hydroxylamine hydrochloride or hydroxylamine sulfate) in the presence of a base or in the absence of a base, for example. The solvent used in this reaction is not particularly limited insofar as it does not inhibit the reaction. Preferable examples of the solvent include organic solvents such as ethanol, methanol, tetrahydrofuran, 1,4-dioxane, 1,2-dimethoxyethane and dichloromethane, and mixtures of these solvents and water. Examples of the base used include sodium carbonate, potassium carbonate, sodium acetate, pyridine, sodium hydroxide, cesium hydroxide, barium hydroxide and 2,6-lutidine. The reaction time is not particularly limited and is usually 5 minutes to 24 hours, and preferably 5 minutes to 12 hours. The reaction temperature is usually 0° C. to solvent reflux temperature, and more preferably room temperature to solvent reflux temperature.

Step 8-3:

This step is a step of obtaining a compound (8-5) by subjecting the oxime compound (8-4) to 1,3-dipolar cycloaddition reaction.

The reaction in this step can be performed under the same conditions as those usually used in 1,3-dipolar cycloaddition reaction such as the conditions described in J. Org. Chem. 1993, 58, 4538-4546 and Tetrahedron Letters, Vol. 29, No. 41, pp 5312-5316.

Specifically, the compound (8-5) can be obtained by heating the compound (8-4) under reflux in a toluene solvent, for example. The solvent used in this reaction is not particularly limited insofar as it does not inhibit the reaction. Preferable examples of the solvent include organic solvents such as toluene, xylene and chlorobenzene. The reaction time is not particularly limited and is usually 5 minutes to 24 hours, and preferably 5 minutes to 12 hours. The reaction temperature is usually 0° C. to solvent reflux temperature, and more preferably room temperature to solvent reflux temperature.

Favorable results such as an improved yield and a reduced reaction time may be achieved by addition of a Lewis acid such as zinc chloride as an additive, for example.

Favorable results such as a reduced reaction time and an improved yield may be obtained by performing this reaction using a microwave reactor.

Step 8-4:

The compound (8-6) can be synthesized from the compound (8-5) using a series of methods described in the above preparation method ((Step 5-4) to (Step 5-6)).

Step 8-5:

This step is a step of synthesizing the compound (8-7) from the compound (8-6) as a raw material using a method described in the above preparation method (Step 5-7).

Step 8-6:

This step is a step of obtaining the compound (8-8) by deprotecting the amino group of the compound (8-6). The amino protecting group used in this step is not particularly limited. When $Prt_3$ is a 2,4-dimethoxybenzyl group, for example, this step can be performed under the same conditions as those generally used (such as the conditions described in a document such as Tetrahedron Vol. 47, No. 26, pp 4591-4602, 1991). When $Prt_3$ is a 2,4-dimethoxybenzyl group in this step, the solvent used in this step is not particularly limited insofar as it does not inhibit the reaction and allows the starting material to be dissolved therein to a certain extent. For example, the first-stage reaction solvent may be methylene chloride or chloroform, and the second-stage reaction solvent may be methanol. The reaction temperature in this step is usually 0° C. to room temperature. The reaction time in this step is not particularly limited and is usually 0.5 to 24 hours, and preferably 0.5 to 12 hours.

9. General Preparation Method 9:

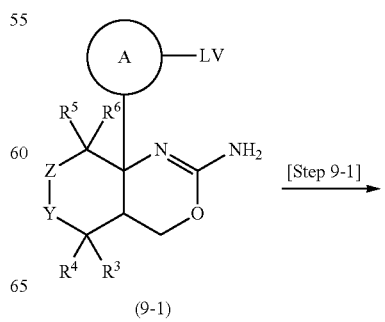

(9-1)

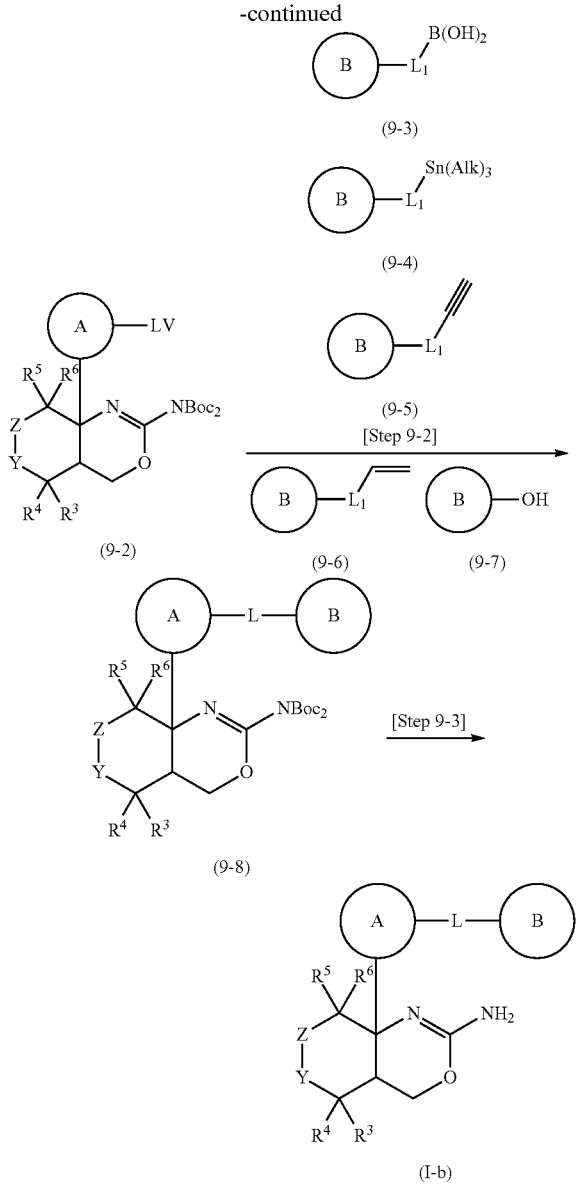

available product used as is, can also be prepared from a commercially available product by a method known to a person skilled in the art, and can further be prepared by a method described in Preparation Examples among Examples.

Step 9-1:

This step is a step of obtaining a compound (9-2) by di-t-butoxycarbonylating the compound (9-1). This reaction can be performed under the same conditions as those generally used in t-butoxycarbonylation of an amide compound such as the conditions described in T. W. Green and P. G. M. Wuts, "Protective Groups in Organic Chemistry, Third Edition", John Wiley & Sons, P. 642-643 and J. Org. Chem. 2005, 70, 2445-2454. The compound (9-2) can be obtained by reacting the compound (9-1) with di-tert-butyl dicarbonate using 4-dimethylaminopyridine as a base in a solvent such as THF, for example.

The solvent used in this reaction is not particularly limited insofar as it does not inhibit the reaction. Preferable examples of the solvent include organic solvents such as tetrahydrofuran, 1,4-dioxane, 1,2-dimethoxyethane, dichloromethane, DMF and acetonitrile, and mixed solvents thereof. Examples of the base used include triethylamine, 4-dimethylaminopyridine, DBU and mixtures thereof. A catalytic amount to an excess of, and more preferably 0.1 to 5 equivalents of the base is used with respect to the compound (9-1). Two equivalents to an excess of, and more preferably 2 to 10 equivalents of di-tert-butyl dicarbonate is used with respect to the compound (9-1). The reaction time is not particularly limited and is usually 5 minutes to 24 hours, and preferably 5 minutes to 12 hours. The reaction temperature is usually −20° C. to solvent reflux temperature, and more preferably 0° C. to solvent reflux temperature.

Step 9-2:

This step is a step of obtaining a compound (9-8) by coupling reaction of the compound (9-2) with the compound (9-3), (9-4), (9-5), (9-6) or (9-7) using a transition metal. This reaction can be performed under the conditions usually used in coupling reaction using a transition metal (such as Suzuki-Miyaura reaction, Stille reaction, Sonogashira reaction, Heck reaction or aryl ether synthesis reaction of Buckwald et al.).

Examples of the Suzuki-Miyaura reaction include reactions in documents such as J. Org. Chem. 2007, 72, 7207-7213, J. Am. Chem. Soc. 2000, 122, 4020-4028 and J. Org. Chem. 2007, 72, 5960-5967. Examples of the Stille coupling reaction include reaction in a document such as J. Am. Chem. Soc. 1990, 112, 3093-3100. Examples of the Sonogashira reaction include reactions in documents such as J. Org. Chem. 2007, 72, 8547-8550 and J. Org. Chem. 2008, 73, 234-240. Examples of the Heck reaction include reaction in a document such as J. Am. Chem. Soc. 2005, 127, 16900-16911. Examples of the aryl ether synthesis reaction of Buchwald et al. include reaction in a document such as Buchwald, S. L. et al., J Am Chem Soc (1999) 121 (18), 4369-4378. The organometallic catalyst used in this reaction is not particularly limited. Preferable examples of the organometallic catalyst include metal catalysts such as tetrakis(triphenylphosphine) palladium (0), dichlorobis(triphenylphosphine)palladium (II), [1,1′-bis(diphenylphosphino)ferrocene]palladium (II) dichloride, bis(tert-butylphosphine)palladium (0), palladium (II) acetate and [1,3-bis(diphenylphosphino)propane]nickel (II), and mixtures of these metal catalysts. The amount of the organometallic catalyst used is about 0.001 to 0.5 equivalent with respect to the raw material. The amount of the compound (9-3), (9-4), (9-5), (9-6) or (9-7) used is not particularly limited and is usually 1 to 5 equivalents with respect to the compound (9-2). The solvent used in this reaction is not particularly limited insofar as it does not inhibit the reaction.

In the formula, $L_1$ represents a single bond or a $C_{1-6}$ alkylene group in compounds (9-3) and (9-4) and represents a single bond or a $C_{1-4}$ alkylene group in compounds (9-5) and (9-6), L represents a single bond, an oxygen atom, a $C_{1-6}$ alkylene group, a $C_{2-6}$ alkenylene group or a $C_{2-6}$ alkynylene group, Alk represents a $C_{1-6}$ alkyl group, and Ring A, Ring B, $R^3$, $R^4$, $R^5$, $R^6$, Y, Z and LV are as defined above.

General Preparation Method 9 is a method for preparing the compound (I-b) of the general formula (I) according to the present invention, wherein L is a single bond, an oxygen atom, a $C_{1-6}$ alkylene group, a $C_{2-6}$ alkenylene group or a $C_{2-6}$ alkynylene group and $R^1$ and $R^2$ are hydrogen atoms, from a compound (9-1) as a raw material by the above steps.

The compound (9-1) can be prepared from a commercially available product by General Preparation Method 1, General Preparation Method 5 or a combination of General Preparation Method 1 and Method 2B of General Preparation Method 2, and can also be prepared by a method described in Preparation Examples among Examples. The compounds (9-3), (9-4), (9-5), (9-6) and (9-7) each can be a commercially Preferable examples of the solvent include benzene, toluene, xylene, N,N-dimethylformamide, 1-methyl-2-pyrrolidone, tetrahydrofuran, 1,2-dimethoxyethane, 1,4-dioxane, acetonitrile and propionitrile. The reaction temperature is not particularly limited and is usually ice-cold temperature to solvent reflux temperature, and preferably room temperature to solvent reflux temperature, for example. The reaction time is not particularly limited and is usually 0.5 to 48 hours, and preferably 0.5 to 24 hours.

A more preferable result such as an improved yield may be achieved by carrying out this reaction in the presence of a base or a salt. Such a base or salt is not particularly limited. Preferable examples of the base or salt include bases or salts such as sodium carbonate, potassium carbonate, barium hydroxide, cesium carbonate, potassium phosphate, potassium fluoride and solutions thereof, and triethylamine, N,N-diisopropylethylamine, lithium chloride and copper (I) iodide.

Step 9-3:

This step is a step of synthesizing the compound (I-b) from the compound (9-8) as a raw material using a method described in the above preparation method (Step 3-4).

The compound of the formula (I) according to the present invention, wherein at least one of $R^1$ and $R^2$ is a $C_{1-6}$ alkyl group which optionally has 1 to 3 substituents selected from Substituent Group α, a $C_{1-6}$ alkylcarbonyl group which optionally has 1 to 3 substituents selected from Substituent Group α, a $C_{6-14}$ arylcarbonyl group which optionally has 1 to 3 substituents selected from Substituent Group α, a $C_{1-6}$ alkylsulfonyl group which optionally has 1 to 3 substituents selected from Substituent Group α, a $C_{6-14}$ arylsulfonyl group which optionally has 1 to 3 substituents selected from Substituent Group α, a 3- to 10-membered carbocyclic group which optionally has 1 to 3 substituents selected from Substituent Group α or a 5- to 10-membered heterocyclic group which optionally has 1 to 3 substituents selected from Substituent Group α, can be obtained by further reacting the compound (I-b) obtained in General Preparation Method 9 with a corresponding halide compound such as a $C_{1-6}$ alkyl halide.

10. General Preparation Method 10:

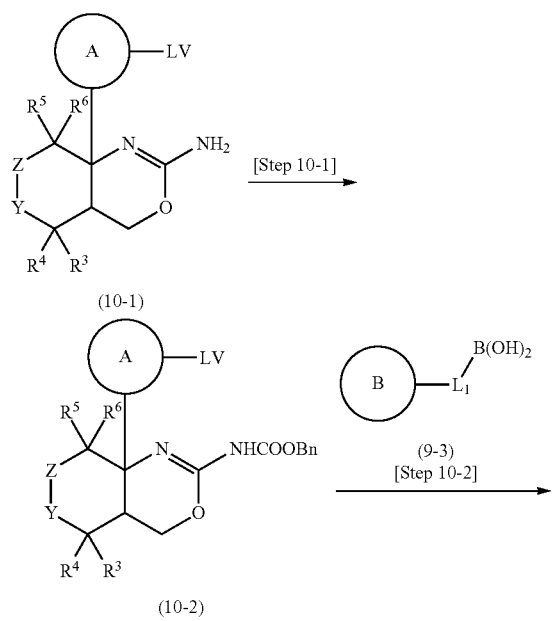

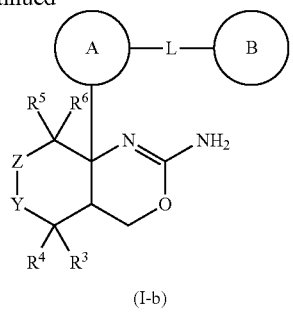

In the formula, Ring A, Ring B, $R^3$, $R^4$, $R^5$, $R^6$, Z, Y, $L_1$, L and LV are as defined above.

General Preparation Method 10 is a method for preparing the compound (I-b) of the general formula (I) according to the present invention, wherein L is a single bond and $R^1$ and $R^2$ are hydrogen atoms, from a compound (10-1).

The compound (10-1) can be prepared from a commercially available product by General Preparation Method 1, General Preparation Method 5 or a combination of General Preparation Method 1 and Method 2B of General Preparation Method 2, and can also be prepared by a method described in Preparation Examples among Examples.

Step 10-1:

This step is a step of obtaining a compound (10-2) by benzyloxycarbonylation of the compound (10-1).

The reaction can be performed under the same conditions as those generally used in benzyloxycarbonylation of an amino compound such as the conditions described in a document such as T. W. Green and P. G. M. Wuts, "Protective Groups in Organic Chemistry, Third Edition", John Wiley & Sons, P. 531-537. The compound (10-2) can be obtained by reacting the compound (10-1) with benzyl chloroformate in a mixed solvent of 1,4-dioxane and a saturated sodium bicarbonate solution, for example.

Step 10-2:

This step is a step of synthesizing the compound (I-b) from the compound (10-2) as a raw material using the same method as Suzuki-Miyaura reaction described in the above preparation method (Step 9-2).

The compound of the formula (I) according to the present invention, wherein at least one of $R^1$ and $R^2$ is a $C_{1-6}$ alkyl group which may have 1 to 3 substituents selected from Substituent Group α, a $C_{1-6}$ alkylcarbonyl group which optionally has 1 to 3 substituents selected from Substituent Group α, a $C_{6-14}$ arylcarbonyl group which optionally has 1 to 3 substituents selected from Substituent Group α, a $C_{1-6}$ alkylsulfonyl group which optionally has 1 to 3 substituents selected from Substituent Group α, a $C_{6-14}$ arylsulfonyl group which optionally has 1 to 3 substituents selected from Substituent Group α, a 3- to 10-membered carbocyclic group which optionally has 1 to 3 substituents selected from Substituent Group α or a 5- to 10-membered heterocyclic group which optionally has 1 to 3 substituents selected from Substituent Group α, can be obtained by further reacting the compound (I-b) obtained in General Preparation Method 10 with a corresponding halide compound such as a $C_{1-6}$ alkyl halide.

11. General Preparation Method 11:

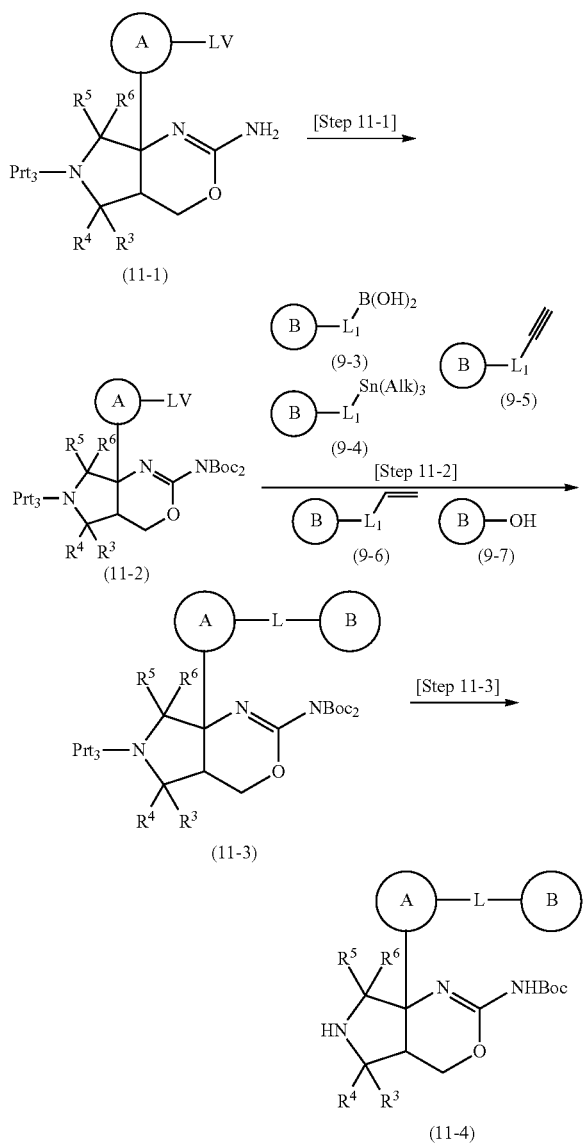

In the formula, Ring A, Ring B, $R^3$, $R^4$, $R^5$, $R^6$, $L_1$, L, LV, Alk and $Prt_3$ are as defined above.

General Preparation Method 11 shows General Preparation Method 9 in the case where Y is a nitrogen atom and Z is a single bond in the general formula. The method is a method for preparing a compound (11-4) which is a synthetic intermediate of the compound (1) according to the present invention from a compound (11-1).

The compound (11-1) can be prepared from a commercially available product by General Preparation Method 5 or General Preparation Method 8, and can also be prepared by a method described in Preparation Examples among Examples.

Step 11-1:
This step is a step of synthesizing a compound (11-2) from the compound (11-1) as a raw material using a method described in the above preparation method (Step 9-1).

Step 11-2:
This step is a step of synthesizing a compound (11-3) from the compound (11-2) as a raw material using a method described in the above preparation method (Step 9-2).

Step 11-3:
This step is a step of obtaining the compound (11-4) by deprotecting the amino group of the compound (11-3). The amino protecting group used in this step is not particularly limited. When $Prt_3$ is a 2,4-dimethoxybenzyl group, for example, this step can be performed under the same conditions as those generally used (such as the conditions described in a document such as Tetrahedron Vol. 47, No. 26, pp 4591-4602, 1991). In this step, when $Prt_3$ is a 2,4-dimethoxybenzyl group, one Boc group can be deprotected simultaneously with deprotection of the 2,4-dimethoxybenzyl group. When $Prt_3$ is a 2,4-dimethoxybenzyl group in this step, the solvent used in this step is not particularly limited insofar as it does not inhibit the reaction and allows the starting material to be dissolved therein to a certain extent. For example, the first-step reaction solvent may be methylene chloride or chloroform, and the second-step reaction solvent may be methanol. The reaction temperature in this step is usually 0° C. to room temperature. The reaction time in this step is not particularly limited and is usually 0.5 to 24 hours, and preferably 0.5 to 12 hours.

12. General Preparation Method 12:

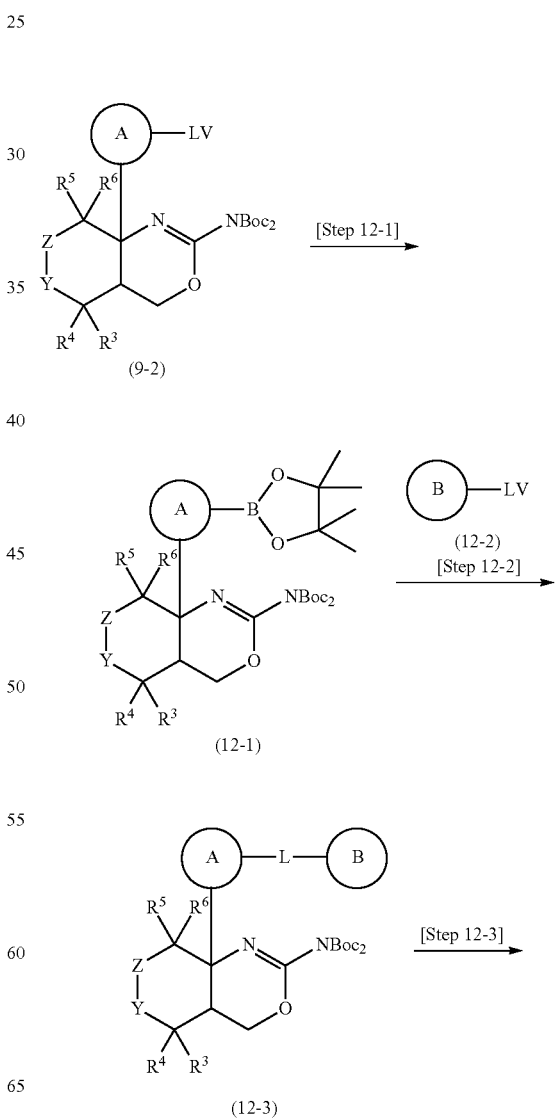

-continued

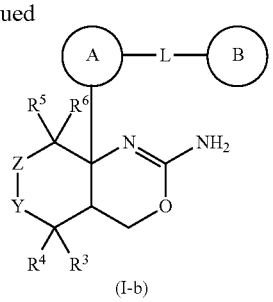

(I-b)

In the formula, Ring A, Ring B, $R^3$, $R^4$, $R^5$, $R^6$, Y, Z, L and LV are as defined above.

General Preparation Method 12 is a method for preparing the compound (I-b) of the general formula (I) according to the present invention, wherein L is a single bond and $R^1$ and $R^2$ are hydrogen atoms, from a compound (9-2).

The compound (9-2) can be prepared from a commercially available product by General Preparation Method 9, and can also be prepared by a method described in Preparation Examples among Examples. A compound (12-2) can be a commercially available product used as is, can also be prepared from a commercially available product by a method known to a person skilled in the art, and can further be prepared by a method described in Preparation Examples among Examples.

Step 12-1:

This step is a step of obtaining a compound (12-1) by coupling reaction of the compound (9-2) using a transition metal.

The reaction in this step can be performed under the same conditions as those usually used in coupling reaction using a transition metal such as the conditions described in Org. Lett. 2007, Vol. 9, No. 4, 558-562 and Bioorg. Med. Chem., 14 (2006) 4944-4957. Specifically, the compound (12-1) can be obtained by reacting the compound (9-2) with bis(pinacolato) diborane under heating conditions in a solvent such as DMF in the presence of a catalyst such as potassium acetate or [1,1'-bis(diphenylphosphino)ferrocene]palladium (II) dichloride, for example.

The organometallic catalyst used in this reaction is not particularly limited. Preferable examples of the organometallic catalyst include metal catalysts such as dichlorobis(triphenylphosphine)palladium (II), [1,1'-bis(diphenylphosphino) ferrocene]palladium (II) dichloride, bis(tert-butylphosphine) palladium (0), palladium (II) acetate and [1,3-bis (diphenylphosphino)propane]nickel (II). The amount of the organometallic catalyst used is about 0.001 to 0.5 equivalent with respect to the raw material. The solvent used in this reaction is not particularly limited insofar as it does not inhibit the reaction. Preferable examples of the solvent include benzene, toluene, xylene, N,N-dimethylformamide, 1-methyl-2-pyrrolidone, dimethyl sulfoxide, tetrahydrofuran, 1,2-dimethoxyethane, 1,4-dioxane, acetonitrile and propionitrile. The reaction temperature is not particularly limited and is usually ice-cold temperature to solvent reflux temperature, and preferably room temperature to solvent reflux temperature, for example. The reaction time is not particularly limited and is usually 0.5 to 72 hours, and preferably 0.5 to 24 hours.

A more preferable result such as an improved yield may be achieved by carrying out this reaction in the presence of a base. Such a base is not particularly limited. Preferable examples of the base include bases such as potassium acetate, sodium acetate, sodium carbonate, potassium carbonate, cesium carbonate, potassium phosphate, potassium fluoride, triethylamine and N,N-diisopropylethylamine.

Step 12-2:

This step is a step of synthesizing a compound (12-3) from the compound (12-1) as a raw material using a method described in the above preparation method (Step 9-2).

Step 12-3:

This step is a step of synthesizing the compound (I-b) from the compound (12-3) as a raw material using a method described in the above preparation method (Step 3-4).

The compound of the formula (I) according to the present invention, wherein at least one of $R^1$ and $R^2$ is a $C_{1-6}$ alkyl group which may have 1 to 3 substituents selected from Substituent Group α, a $C_{1-6}$ alkylcarbonyl group which optionally has 1 to 3 substituents selected from Substituent Group α, a $C_{6-14}$ arylcarbonyl group which optionally has 1 to 3 substituents selected from Substituent Group α, a $C_{1-6}$ alkylsulfonyl group which optionally has 1 to 3 substituents selected from Substituent Group α, a $C_{6-14}$ arylsulfonyl group which optionally has 1 to 3 substituents selected from Substituent Group α, a 3- to 10-membered carbocyclic group which optionally has 1 to 3 substituents selected from Substituent Group α or a 5- to 10-membered heterocyclic group which optionally has 1 to 3 substituents selected from Substituent Group α, can be obtained by further reacting the compound (I-b) obtained in General Preparation Method 12 with a corresponding halide compound such as a $C_{1-6}$ alkyl halide.

13. General Preparation Method 13:

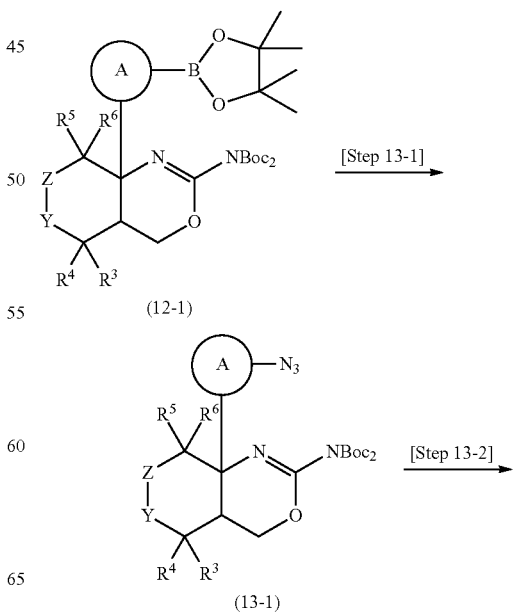

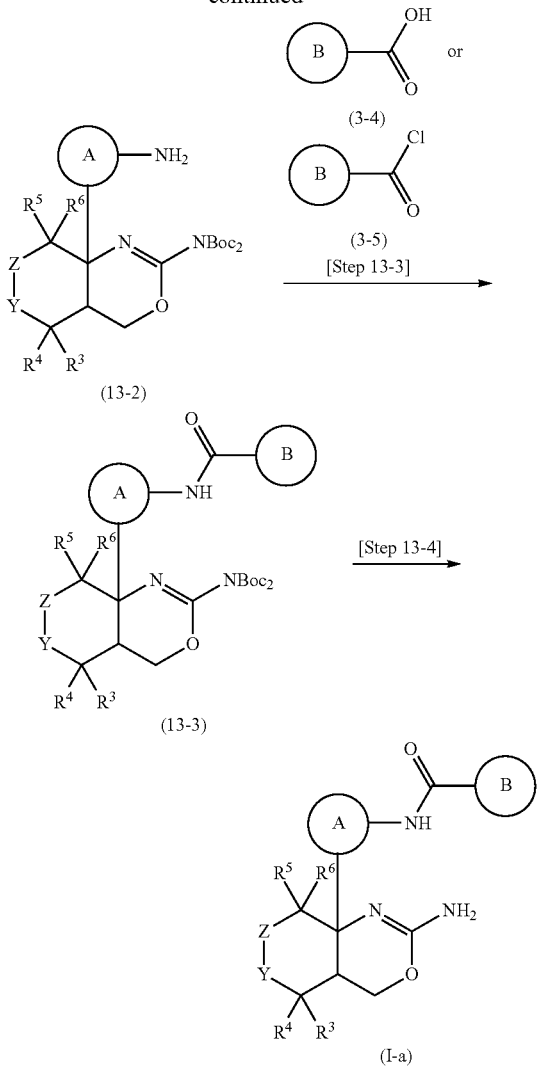

In the formula, Ring A, Ring B, $R^3$, $R^4$, $R^5$, $R^6$, Y and Z are as defined above.

General Preparation Method 13 is a method for preparing the compound (I-a) of the general formula (I) according to the present invention, wherein L is —NHCO— and $R^1$ and $R^2$ are hydrogen atoms, from a compound (12-1).

The compound (12-1) can be prepared from a commercially available product by General Preparation Method 12, and can also be prepared by a method described in Preparation Examples among Examples.

Step 13-1:

This step is a step of obtaining a compound (13-1) by reaction of the compound (12-1) with sodium azide in the presence of a copper catalyst.

The reaction in this step can be performed under the same conditions as those described in Org. Lett. 2007, Vol. 9, No. 5, 761-764 and Tetrahedron Lett. 2007, 48, 3525-3529, for example. Specifically, the compound (13-1) can be obtained by reacting the compound (12-1) with sodium azide at room temperature using a solvent such as methanol in the presence of a catalyst such as copper (II) acetate, for example.

The catalyst used in this reaction is not particularly limited. Preferable examples of the catalyst include metal catalysts such as copper (II) acetate, copper (II) sulfate, copper (I) iodide and copper (I) chloride. The amount of the catalyst used is not particularly limited and is usually about 0.1 to 0.5 equivalent with respect to the raw material. The solvent used in this reaction is not particularly limited insofar as it does not inhibit the reaction and allows the starting material to be dissolved therein to a certain extent. Preferable examples of the solvent include methanol, N,N-dimethylformamide, 1-methyl-2-pyrrolidone, tetrahydrofuran, 1,2-dimethoxyethane, 1,4-dioxane, acetonitrile, propionitrile and dichloromethane. The reaction temperature is not particularly limited and is usually ice-cold temperature to solvent reflux temperature, and preferably room temperature to solvent reflux temperature, for example. The reaction time is not particularly limited and is usually 0.5 to 100 hours, and preferably 1 to 72 hours.

A more preferable result such as an improved yield may be achieved by carrying out this reaction in an oxygen atmosphere.

Step 13-2:

This step is a step of obtaining a compound (13-2) by reduction reaction the azide of the compound (13-1). The reaction in this step can be performed under the same conditions as those described in J. Org. Chem. 2003, 68, 4693-4699, for example. Specifically, the compound (13-2) can be obtained by dissolving the compound (13-1) in a solvent such as methanol, and reacting the solution with sodium borohydride, for example.

Step 13-3:

This step is a step of synthesizing a compound (13-3) from the compound (13-2) as a raw material using a method described in the above preparation method (Step 3-3).

Step 13-4:

This step is a step of synthesizing the compound (I-a) from the compound (13-3) as a raw material using a method described in the above preparation method (Step 3-4).

The compound of the formula (I) according to the present invention, wherein at least one of $R^1$ and $R^2$ is a $C_{1-6}$ alkyl group which optionally has 1 to 3 substituents selected from Substituent Group α, a $C_{1-6}$ alkylcarbonyl group which optionally has 1 to 3 substituents selected from Substituent Group α, a $C_{6-14}$ arylcarbonyl group which optionally has 1 to 3 substituents selected from Substituent Group α, a $C_{1-6}$ alkylsulfonyl group which optionally has 1 to 3 substituents selected from Substituent Group α, a $C_{6-14}$ arylsulfonyl group which optionally has 1 to 3 substituents selected from Substituent Group α, a 3- to 10-membered carbocyclic group which optionally has 1 to 3 substituents selected from Substituent Group α or a 5- to 10-membered heterocyclic group which optionally has 1 to 3 substituents selected from Substituent Group α, can be obtained by further reacting the compound (I-a) obtained in General Preparation Method 13 with a corresponding halide compound such as a $C_{1-6}$ alkyl halide.

Alternatively, —NHCO— of L in the compound (I-a) of the present invention can be converted to —$NR^eCO$— (wherein $R^e$ is a $C_{1-6}$ alkyl group which optionally has 1 to 3 substituents selected from Substituent Group α) by further reacting the compound (I-a) obtained in General Preparation Method 13 with a corresponding halide compound such as a $C_{1-6}$ alkyl halide.

The compound of the formula (I) according to the present invention, wherein L is —$NR^eSO_2$—, can be obtained using a corresponding sulfonyl halide compound in place of the compound (3-4) or (3-5) used in General Preparation Method 13.

14. General Preparation Method 14:
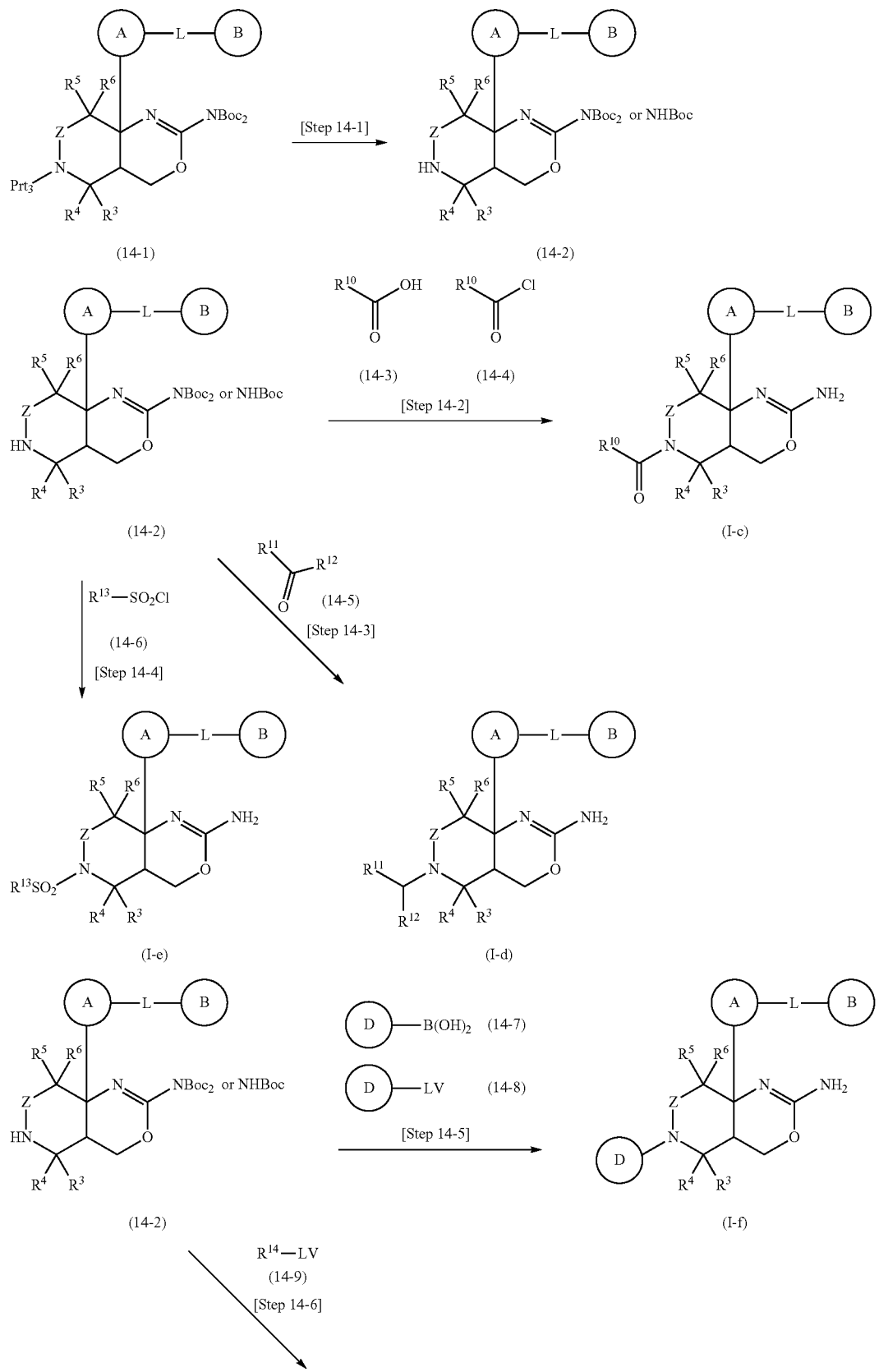

-continued

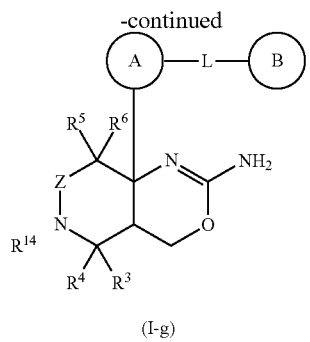

(I-g)

In the formula, Ring A, Ring B, $R^3$, $R^4$, $R^5$, $R^6$, L, Z, $Prt_3$ and LV are as defined above; Ring D represents a $C_{6-14}$ aryl group which optionally has 1 to 3 substituents selected from Substituent Group α or a 5- to 6-membered heteroaryl group which optionally has 1 to 3 substituents selected from Substituent Group α; $R^{10}$ represents a $C_{6-14}$ aryl group which optionally has 1 to 3 substituents selected from Substituent Group α, a 5- to 10-membered heterocyclic group which optionally has 1 to 3 substituents selected from Substituent Group α, a $C_{3-8}$ cycloalkyl group which optionally has 1 to 3 substituents selected from Substituent Group α, a $C_{1-6}$ alkyl group which optionally has 1 to 3 substituents selected from Substituent Group α or a 3- to 10-membered carbocyclic group which optionally has 1 to 3 substituents selected from Substituent Group α; $R^{11}$ and $R^{12}$ are each independently a hydrogen atom, a $C_{6-14}$ aryl group which optionally has 1 to 3 substituents selected from Substituent Group α, a 5- to 10-membered heterocyclic group which optionally has 1 to 3 substituents selected from Substituent Group α, a $C_{3-8}$ cycloalkyl group which optionally has 1 to 3 substituents selected from Substituent Group α, a $C_{1-6}$ alkyl group which optionally has 1 to 3 substituents selected from Substituent Group α or a 3- to 10-membered carbocyclic group which optionally has 1 to 3 substituents selected from Substituent Group α, or $R^{11}$ and $R^{12}$ together may form a ring; $R^{13}$ represents a $C_{6-14}$ aryl group which optionally has 1 to 3 substituents selected from Substituent Group α, a 5- to 10-membered heterocyclic group which optionally has 1 to 3 substituents selected from Substituent Group α, a $C_{3-8}$ cycloalkyl group which optionally has 1 to 3 substituents selected from Substituent Group α, a $C_{1-6}$ alkyl group which optionally has 1 to 3 substituents selected from Substituent Group α or a 3- to 10-membered carbocyclic group which optionally has 1 to 3 substituents selected from Substituent Group α; and $R^{14}$ represents a $C_{7-12}$ aralkyl group which optionally has 1 to 3 substituents selected from Substituent Group α.

General Preparation Method 14 is a method for preparing the compounds (I-c) to (I-g) of the general formula (I) according to the present invention, wherein Y is a nitrogen atom and $R^1$ and $R^2$ are hydrogen atoms, from a compound (14-1).

The compound (14-1) can be prepared from a commercially available product by General Preparation Method 5, General Preparation Method 8, General Preparation Method 9, General Preparation Method 10, General Preparation Method 11, General Preparation Method 12 or a combination thereof, and can also be prepared by a method described in Preparation Examples among Examples.

Compounds (14-3), (14-4), (14-5), (14-6), (14-7), (14-8) and (14-9) each can be a commercially available product used as is, can also be prepared from a commercially available product by a method known to a person skilled in the art, and can further be prepared by a method described in Preparation Examples among Examples.

Step 14-1:

This step is a step of obtaining a compound (14-2) by deprotecting the amino group of the compound (14-1).

The reaction can be performed under the same conditions as those generally used in deprotection of a protecting group of an amino compound such as the conditions described in a document such as T. W. Green and P. G. M. Wuts, "Protective Groups in Organic Chemistry, Third Edition", John Wiley & Sons, P. 494-572.

The amino protecting group used in this step is not particularly limited. When $Prt_3$ is a 2,4-dimethoxybenzyl group, for example, this step can be performed under the same conditions as those generally used (such as the conditions described in a document such as Tetrahedron Vol. 47, No. 26, pp 4591-4602, 1991). One Boc group can be deprotected simultaneously with deprotection of the 2,4-dimethoxybenzyl group. The solvent used in this step is not particularly limited insofar as it does not inhibit the reaction and allows the starting material to be dissolved therein to a certain extent. For example, the first-step reaction solvent may be methylene chloride or chloroform, and the second-step reaction solvent may be methanol. The reaction temperature in this step is usually 0° C. to room temperature. The reaction time in this step is not particularly limited and is usually 0.5 to 24 hours, and preferably 0.5 to 12 hours.

When $Prt_3$ is a benzyloxycarbonyl group, the compound (14-2) can be obtained by deprotecting the compound (14-1) by hydrogenation using palladium-carbon as a catalyst in a solvent such as an alcohol, for example.

Step 14-2:

This step is a step of synthesizing the compound (I-c) from the compound (14-2) as a raw material using a method described in the above preparation method ((Step 3-3) and (Step 3-4)).

Step 14-3:

This step is a step of synthesizing the compound (I-d) using a method described in the above preparation method (Step 3-4) after reductive amination reaction of the compound (14-2) with the compound (14-5).

The reductive amination reaction can be performed under the same conditions as those usually used in reductive amination reaction of a carbonyl compound with an amine compound. The reduction reaction in this step is not particularly limited. Examples of the reduction reaction include reductive amination reaction using a reducing agent such as borane or a boron hydride complex compound. Examples of the reductive amination reaction using a boron hydride complex compound include a method described in a document such as J.

Org. Chem. 1996, 61, 3849. Examples of the boron hydride complex compound that can be used include sodium borohydride, sodium cyanoborohydride and sodium triacetoxyborohydride.

When the boron hydride complex compound is used as a reducing agent, the solvent is not particularly limited insofar as it does not inhibit the reaction and allows the starting material to be dissolved therein to a certain extent. Specific examples of the solvent that can be used include methanol, ethanol, tetrahydrofuran, N,N-dimethylformamide, dichloromethane and 1,2-dichloroethane. A more preferable result such as an improved yield can be achieved by carrying out this reaction in the presence of an acid. Such an acid is not particularly limited. Preferable examples of the acid include mineral acids such as hydrochloric acid, organic acids such as acetic acid, and Lewis acids such as zinc chloride, a boron trifluoride-diethyl ether complex and titanium (IV) tetraisopropoxide.

Step 14-4:

This step is a step of synthesizing the compound (I-e) using a method described in the above preparation method (Step 3-4) after sulfonylation of the amino group of the compound (14-2). For the sulfonylation, reaction using a sulfonyl chloride derivative is known to a person skilled in the art.

Step 14-5:

This step is a step of synthesizing the compound (I-f) using a method described in the above preparation method (Step 3-4) after coupling reaction of the compound (14-2) with the compound (14-7) or (14-8). Reaction such as coupling using a transition metal complex or the like or nucleophilic aromatic substitution (SNAr reaction) is used in this step.

The coupling reaction in this step can be performed under the same conditions as those described in Org. Lett. 2007, Vol. 9, No. 5, 761-764 and Org. Lett. 2003, Vol. 5, No. 23, 4397-4400, for example. Specifically, the coupling reaction can be performed by reacting the compound (14-2) with the compound (14-7) at room temperature to 50° C. using a solvent such as dichloromethane in the presence of molecular sieve 4A and a catalyst such as copper (II) acetate, for example.

The catalyst used in this reaction is not particularly limited. Preferable examples of the catalyst include metal catalysts such as copper (II) acetate, copper (II) sulfate, copper (I) iodide and copper (I) chloride. The amount of the catalyst used is not particularly limited and is usually about 0.1 to 0.5 equivalent with respect to the raw material. The solvent used in this reaction is not particularly limited insofar as it does not inhibit the reaction and allows the starting material to be dissolved therein to a certain extent. Preferable examples of the solvent include N,N-dimethylformamide, 1-methyl-2-pyrrolidone, tetrahydrofuran, 1,2-dimethoxyethane, 1,4-dioxane, acetonitrile, propionitrile and dichloromethane. The reaction temperature is not particularly limited and is usually ice-cold temperature to solvent reflux temperature, and preferably room temperature to solvent reflux temperature, for example. The reaction time is not particularly limited and is usually 0.5 to 100 hours, and preferably 1 to 72 hours.

A more preferable result such as an improved yield may be achieved by carrying out this reaction in an oxygen atmosphere.

When this step is coupling using a transition metal complex or the like as a catalyst, the reaction can be performed using the compound (14-2) and the compound (14-8) which is an aryl halide derivative, a heteroaryl halide derivative, an aryloxy trifluoromethanesulfonate derivative or a heteroaryloxy trifluoromethanesulfonate derivative under the same conditions as those usually used (such as the conditions described in a document such as Org. Lett. 2002, Vol. 4, No. 4, 581). The aryl halide derivative, the heteroaryl halide derivative, the aryloxy trifluoromethanesulfonate derivative or the heteroaryloxy trifluoromethanesulfonate derivative used in this step can be a commercially available product used as is, and can also be prepared from a commercially available product by a method known to a person skilled in the art. Examples of the transition metal complex used in this step include dichlorobis(triphenylphosphine)palladium (II), tetrakis(triphenylphosphine)palladium (0), tris(dibenzylideneacetone) palladium (0) and a copper-diol ligand complex. In this reaction, a phosphorus ligand (such as preferably triphenylphosphine, tri-o-tolylphosphine, tri-tert-butylphosphine, 2,2'-bis(diphenylphosphino)-1,1'-binaphthyl or 1,1'-bis(diphenylphosphino)ferrocene) may be further added in order to obtain favorable results (such as a reduced reaction temperature, a reduced reaction time and an improved yield). When the transition metal complex used is a palladium complex, the reaction in this step is preferably performed under a nitrogen or argon atmosphere. The solvent used in this step is not particularly limited insofar as it does not inhibit the reaction and allows the starting material to be dissolved therein to a certain extent. For example, when the transition metal complex used is a palladium complex, N,N-dimethylformamide, N-methyl-2-pyrrolidone, 1,4-dioxane, toluene, xylene or the like can be used. When the transition metal complex used is a copper-diol complex, 2-propanol or the like can be used. The reaction temperature in this step is usually room temperature to solvent reflux temperature. The reaction time in this step is not particularly limited and is usually 0.5 to 72 hours, and preferably 0.5 to 24 hours.

When this step is nucleophilic aromatic substitution (SNAr reaction), the reaction can be performed using the compound (14-2) and the compound (14-8) which is an aryl halide derivative, a heteroaryl halide derivative, an aryloxy trifluoromethanesulfonate derivative or a heteroaryloxy trifluoromethanesulfonate derivative in the presence of a base under the same conditions as those usually used. The aryl halide derivative, the heteroaryl halide derivative, the aryloxy trifluoromethanesulfonate derivative or the heteroaryloxy trifluoromethanesulfonate derivative used in this step can be a commercially available product used as is, and can also be prepared from a commercially available product by a method known to a person skilled in the art. The nucleophilic aromatic substitution (SNAr reaction) used in this step can be performed under the same conditions as those generally used (such as the conditions according to methods described in documents such as Org. Prep. Proced. int. 39 (2007) 4, 399-402, Bioorg. Med. Chem. Lett. 15 (2005) 9, 2409-2413 and Bioorg. Med. Chem. Lett. 15 (2005) 3, 719-723). The solvent used in this step is not particularly limited insofar as it does not inhibit the reaction and allows the starting material to be dissolved therein to a certain extent. Examples of the solvent that can be used include N,N-dimethylformamide, N-methyl-2-pyrrolidone, dimethyl sulfoxide and acetonitrile. The base used in this step is not particularly limited. Examples of the base include potassium carbonate, sodium carbonate, sodium hydride and tetrabutylammonium fluoride. Potassium carbonate, sodium carbonate and tetrabutylammonium fluoride are preferably used. The reaction temperature in this step is usually room temperature to solvent reflux temperature. The reaction time in this step is not particularly limited and is usually 0.5 to 24 hours, and preferably 0.5 to 12 hours.

Step 14-6:

This step is a step of synthesizing the compound (I-g) from the compound (14-2) as a raw material using a method described in the above preparation method ((Step 8-1) and (Step 3-4)).

The compound of the formula (I) according to the present invention, wherein at least one of $R^1$ and $R^2$ is a $C_{1-6}$ alkyl group which optionally has 1 to 3 substituents selected from Substituent Group α, a $C_{1-6}$ alkylcarbonyl group which optionally has 1 to 3 substituents selected from Substituent Group α, a $C_{6-14}$ arylcarbonyl group which optionally has 1 to 3 substituents selected from Substituent Group α, a $C_{1-6}$ alkylsulfonyl group which optionally has 1 to 3 substituents selected from Substituent Group α, a $C_{6-14}$ arylsulfonyl group which optionally has 1 to 3 substituents selected from Substituent Group α, a 3- to 10-membered carbocyclic group which optionally has 1 to 3 substituents selected from Substituent Group α or a 5- to 10-membered heterocyclic group which optionally has 1 to 3 substituents selected from Substituent Group α, can be obtained by further reacting any of the compounds (I-c) to (I-g) obtained in General Preparation Method 14 with a corresponding halide compound such as a $C_{1-6}$ alkyl halide.

The compound of the formula (I) according to the present invention obtained in this manner can be converted to a pharmaceutically acceptable salt by a conventional method where necessary. The salt can be prepared by a method in which methods typically used in the field of organic synthetic chemistry and the like are appropriately combined. Specific examples of the method include neutralization titration of a free solution of the compound of the present invention with an acid solution. The compound of the formula (I) according to the present invention can be converted to a solvate by subjecting the compound to solvate forming reaction known per se where necessary.

The fused aminodihydro-oxazine derivative or pharmaceutically acceptable salt thereof or solvate thereof according to the present invention has an extremely excellent Aβ production inhibitory effect or BACE1 inhibitory effect and is extremely useful as a prophylactic or therapeutic agent for a neurodegenerative disease caused by Aβ and typified by Alzheimer-type dementia.

The present invention further provides a compound of formula (I) or a pharmaceutically acceptable salt thereof for use in therapy.

In another aspect, the invention provides the use of a compound of formula (I) as defined above, or a pharmaceutically acceptable salt thereof, for the manufacture of a medicament for the treatment or prevention of a neurodegenerative disease. Examples of neurodegenerative diseases include Alzheimer-type dementia and Down's syndrome.

The fused aminodihydro-oxazine derivative or pharmaceutically acceptable salt thereof or solvate thereof according to the present invention can be formulated by a conventional method. Preferable examples of the dosage form include tablets, coated tablets such as film tablets and sugar-coated tablets, fine granules, granules, powders, capsules, syrups, troches, inhalants, suppositories, injections, ointments, eye drops, nasal drops, ear drops, cataplasms and lotions.

These solid preparations such as tablets, capsules, granules and powders can contain generally 0.01 to 100 wt %, and preferably 0.1 to 100 wt % of the fused aminodihydro-oxazine derivative or pharmaceutically acceptable salt thereof or solvate thereof according to the present invention as an active ingredient.

The active ingredient is formulated by blending ingredients generally used as materials for a pharmaceutical preparation and adding an excipient, a disintegrant, a binder, a lubricant, a colorant and a corrective typically used, and adding a stabilizer, an emulsifier, an absorbefacient, a surfactant, a pH adjuster, a preservative and an antioxidant where necessary, for example, using a conventional method. Examples of such ingredients include animal and vegetable oils such as soybean oil, beef tallow and synthetic glyceride; hydrocarbons such as liquid paraffin, squalane and solid paraffin; ester oils such as octyldodecyl myristate and isopropyl myristate; higher alcohols such as cetostearyl alcohol and behenyl alcohol; a silicone resin; silicone oil; surfactants such as polyoxyethylene fatty acid ester, sorbitan fatty acid ester, glycerol fatty acid ester, polyoxyethylene sorbitan fatty acid ester, polyoxyethylene hydrogenated castor oil and a polyoxyethylene-polyoxypropylene block copolymer; water-soluble polymers such as hydroxyethylcellulose, polyacrylic acid, a carboxyvinyl polymer, polyethylene glycol, polyvinylpyrrolidone and methylcellulose; lower alcohols such as ethanol and isopropanol; polyhydric alcohols such as glycerol, propylene glycol, dipropylene glycol and sorbitol; sugars such as glucose and sucrose; inorganic powders such as silicic anhydride, magnesium aluminum silicate and aluminum silicate; and purified water. Examples of the excipient used include lactose, corn starch, saccharose, glucose, mannitol, sorbitol, crystalline cellulose and silicon dioxide. Examples of the binder used include polyvinyl alcohol, polyvinyl ether, methylcellulose, ethylcellulose, gum arabic, tragacanth, gelatin, shellac, hydroxypropylmethylcellulose, hydroxypropylcellulose, polyvinylpyrrolidone, a polypropylene glycol-polyoxyethylene block copolymer and meglumine. Examples of the disintegrant used include starch, agar, gelatin powder, crystalline cellulose, calcium carbonate, sodium bicarbonate, calcium citrate, dextrin, pectin and carboxymethylcellulose calcium. Examples of the lubricant used include magnesium stearate, talc, polyethylene glycol, silica and hydrogenated vegetable oil. Examples of the colorant used include those permitted to be added to pharmaceuticals. Examples of the corrective used include cocoa powder, menthol, empasm, mentha oil, borneol and cinnamon powder. Obviously, the ingredients are not limited to the above additive ingredients.

For example, an oral preparation is prepared by adding the fused aminodihydro-oxazine derivative or pharmaceutically acceptable salt thereof or solvate thereof according to the present invention as an active ingredient, an excipient and, where necessary, a binder, a disintegrant, a lubricant, a colorant, a corrective and the like, and then forming the mixture into powder, fine granules, granules, tablets, coated tablets, capsules or the like by a conventional method. Obviously, tablets or granules may be appropriately coated, for example, sugar coated, where necessary.

For example, a syrup or an injection preparation is prepared by adding a pH adjuster, a solubilizer, an isotonizing agent and the like, and a solubilizing agent, a stabilizer and the like where necessary by a conventional method. The injection may be a previously prepared solution, or may be powder itself or powder containing a suitable additive, which is dissolved before use. The injection can contain usually 0.01 to 100 wt %, and preferably 0.1 to 100 wt % of the active ingredient. Further, a liquid preparation for oral administration such as a suspension or a syrup can contain usually 0.01 to 100 wt %, and preferably 0.1 to 100 wt % of the active ingredient.

For example, an external preparation can be prepared by any conventional method without specific limitations. As a base material, any of various materials usually used for a pharmaceutical, a quasi drug, a cosmetic or the like can be used. Examples of the base material include materials such as animal and vegetable oils, mineral oils, ester oils, waxes, higher alcohols, fatty acids, silicone oils, surfactants, phospholipids, alcohols, polyhydric alcohols, water-soluble polymers, clay minerals and purified water. A pH adjuster, an antioxidant, a chelator, a preservative and fungicide, a colorant, a flavor or the like can be added where necessary. Further, ingredients such as an ingredient having a differentiation inducing effect, a blood flow enhancer, a bactericide, an antiphlogistic, a cell activator, vitamin, amino acid, a humectant and a keratolytic agent can be blended where necessary.

The dose of the fused aminodihydro-oxazine derivative or pharmaceutically acceptable salt thereof or solvate thereof according to the present invention varies according to the degree of symptoms, age, sex, body weight, mode of administration, type of salt and specific type of disease, for example. Typically, the active ingredient is orally administered to an adult at about 30 μg to 10 g, preferably 100 μg to 5 g, and more preferably 100 μg to 1 g per day, or is administered to an adult by injection at about 30 μg to 1 g, preferably 100 μg to 500 mg, and more preferably 100 μg to 300 mg per day, in one or several doses, respectively.

Compounds of the formula (I) may be used in combination with other therapeutic agents, for example medicaments claimed to be useful as either disease modifying or symptomatic treatments of Alzheimer's disease. Suitable examples of such other therapeutic agents maybe symptomatic agents, for examples those known to modify cholinergic transmission such as M1 and M3 muscarinic receptor agonists or allosteric modulators, M2 muscarinic antagonists, acetylcholinesterase inhibitors (such as tetrahydroaminoacridine, donepezil hydrochloride and rivastigmine), nicotinic receptor agonists or allosteric modulators (such as α7 agonists or allosteric modulators or α4β2 agonists or allosteric modulators), PPAR agonists (such as PPARγ agonists), 5-HT$_4$ receptor agonists or partial agonists, histamine H3 antagonists, 5-HT$_6$ receptor antagonists or 5HT1A receptor ligands and NMDA receptor antagonists or modulators, or disease modifying agents such as β-secretase inhibitors.

Thus, in a further aspect, the present invention provides a combination comprising a compound of formula (I) or a pharmaceutically acceptable salt thereof together with a further therapeutic agent or agents.

The combinations referred to above may conveniently be presented for use in the form of a pharmaceutical formulation and thus pharmaceutical formulations comprising a combination as defined above together with a pharmaceutically acceptable carrier or excipient comprise a further aspect of the invention. The individual components of such combinations may be administered either sequentially or simultaneously in separate or combined pharmaceutical formulations.

When a compound of formula (I) or a pharmaceutically acceptable salt thereof is used in combination with a second therapeutic agent active, the dose of each compound may differ from that when the compound is used alone. Appropriate doses will be readily appreciated by those skilled in the art.

Thus, an additional aspect of the invention provides a method of preparation of a pharmaceutical composition, involving admixing at least one compound of formula (I) as defined above, or a pharmaceutically acceptable salt thereof, with one or more pharmaceutically acceptable adjuvants, diluents or carriers and/or with one or more other therapeutically or prophylactically active agents.

In a further aspect, the invention provides a method of inhibiting production of amyloid-β protein and/or of treating or preventing a neurodegenerative disease, such as Alzheimer-type dementia and Down's syndrome, the method involving administering to a human subject suffering from the condition a therapeutically or prophylactically effective amount of the pharmaceutical composition described above or of a compound of formula (I) as defined above, or a pharmaceutically acceptable salt thereof. "Effective amount" means an amount sufficient to cause a benefit to the subject or at least to cause a change in the subject's condition.

The present invention will be described more specifically below with reference to Examples, Preparation Examples and Test Example. However, the present invention is not limited thereto. The abbreviations used in Examples are conventional abbreviations known to a person skilled in the art. Some abbreviations are shown below.

LCMS, LC/MS & LC-MS (liquid chromatography/mass spectrometry); MS (mass spectrometry); MDAP (mass directed auto purification); NMR (nuclear magnetic resonance); s, d, t, dd, m, br (singlet, doublet, triplet, doublet of doublets, multiplet, broad); Ph, Me, Et, Pr, Bu, Bn (phenyl, methyl, ethyl, propyl, butyl, benzyl); THF (tetrahydrofuran); DCM (dichloromethane); DMF (N,N-dimethylformamide); h, hr, hrs (hours); EDC & EDAC (N-3-(dimethylaminopropyl)-N' ethylcarbodiimide hydrochloride); DMAP (4-N,N-dimethylaminopyridine); DMSO (dimethylsulfoxide); UV (ultraviolet); RT & rt (room temperature); Rt (retention time); min & mins (minutes); EtOAc (ethyl acetate); Et$_2$O (diethyl ether); MeCN (acetonitrile); EtOH (ethanol); MeOH (methanol); PhCH$_3$ & PhMe (toluene); tlc (thin layer chromatography); TFA (trifluoroactic acid); NaOH (sodium hydroxide); HCl (hydrochloric acid); NMP (N-methylpyrrolidinone or 1-methyl-2-pyrrolidinone); HPLC (high performance liquid chromatography); TBAF (tetrabutylammonium fluoride); BuLi (n-butyl lithium); PyBOP: benzotriazol-1-yloxytris (pyrrolidino)phosphonium hexafluorophosphate; Pd$_2$DBA$_3$: tris(dibenzylideneacetone)dipalladium; Pd(t-Bu$_3$P)$_2$: bis(tri-t-butylphosphine)palladium; TFA: trifluoroacetic acid; pTLC: preparative thin-layer chromatography.

$^1$H NMR spectra were recorded on a Bruker AM series spectrometer operating at a (reported) frequency of 400 MHz. Chemical shifts in proton nuclear magnetic resonance spectra are recorded in δ units (ppm) relative to tetramethylsilane and coupling constants (J) are recorded in Hertz (Hz). Patterns are designated as s: singlet, d: doublet, t; triplet, br; broad.

The "room temperature" in the following Examples and Preparation Examples typically refers to about 10° C. to about 35° C. "%" indicates wt % unless otherwise specified.

Analysis
Waters HPLC-MS Analytical
Waters Method A: Short__5__95:
LCMS (Acquity HPLC C18, 2.1×50 mm, 1.7 um, 0.6 mL per min, 40° C., gradient 5-95% MeCN in water (0.1% formic acid) over 1.50 min—held for 0.50 min).
Waters Method B: Short__20__95:
LCMS (Acquity HPLC C18, 2.1×50 mm, 1.7 um, 0.6 mL per min, 40° C., gradient 20-95% MeCN in water (0.1% formic acid) over 1.50 min—held for 0.50 min).
Waters Method C: HPLC Long__5__95:
LCMS (Acquity HPLC C18, 2.1×50 mm, 1.7 um, 0.6 mL per min, 40° C., gradient 5-95% MeCN in water (0.1% formic acid) over 3.00 min—held for 1.00 min
Waters Method D: HPLC Long__20__95:
LCMS (Acquity HPLC C18, 2.1×50 mm, 1.7 um, 0.6 mL per min, 40° C., gradient 20-95% MeCN in water (0.1% formic acid) over 3.00 min—held for 1.00 min).
Agilent LCMS Analytical
Agilent Method A: FAST ANALYTICAL:
LCMS (Agilent ZORBAX Eclipse XDB-C18, 4.6×150 mm, 5.0 um, 1.5 mL per min, gradient 5-95% MeCN in water (0.1% formic acid) over 5.00 min—held for 3.00 min).
Agilent Method B: TLC Run No. 2:
LCMS (Agilent ZORBAX Eclipse XDB-C18, 4.6×150 mm, 5.0 um, 1.5 mL per min, gradient 0-100% MeCN in water (0.1% formic acid) over 2.00 min—held for 2.00 min).

Purification (Preparatory HPLC)
Gilson Large Scale Reverse Phase Preparatory HPLC MANUAL2.GCT Method:
reverse phase HPLC (Phenomenex Luna C18, 250×50 mm, 10 um, 80 mL per min, gradient 20% to 95% (over 25 min) then 95% (10 min) MeCN in H₂O [0.1% acetic acid]).
Agilent Large Scale Reverse Phase Preparatory HPLC PREP4.M Method:
reverse phase HPLC (Phenomenex Luna C18, 250×50 mm, 10 um, 80 mL per min, gradient 35% to 100% (over 20 min) then 100% (5 min) MeCN in H₂O [0.1% acetic acid]).
Waters Reverse Phase Preparatory HPLC
i) Buffered:
reverse phase HPLC (XBridge Prep C18, 19×150 mm, 5 um, 20 mL per min, gradient xx % to xx % (over 12 min) then 95% (3 min) MeCN in water [0.1% formic acid]).
ii) Non-Buffered:
reverse phase HPLC (ACE 5 AQ, 21.2×150 mm, 5 um, 20 mL per min, gradient xx % to xx % (over 12 min) then 95% (3 min) MeCN in water).
[No Preparation Examples 1 to 12]

Preparation Example 13

Synthesis of 5-cyanopyridine-2-carboxylic acid

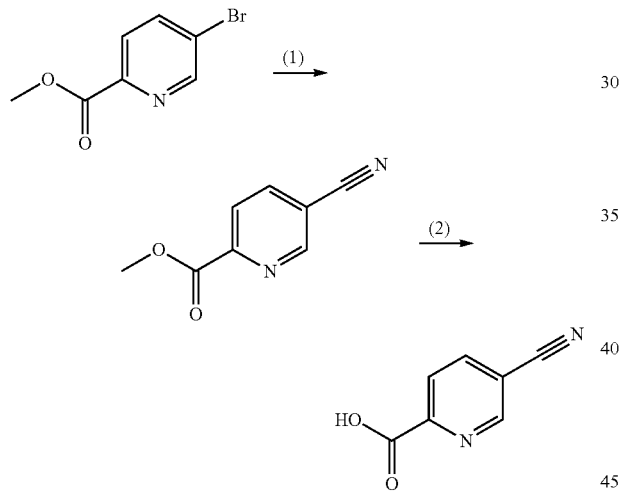

Synthesis of methyl 5-cyanopyridine-2-carboxylate

A mixture of methyl 5-bromopyridine-2-carboxylate (2.8 g) and copper cyanide (3.6 g) in NMP (30 mL) was heated with stirring at 170° C. for 1.5 h. Water was added to the reaction solution at RT, and the insoluble matter was removed by filtration. The filtrate was extracted with EtOAc. The extract was washed with a saturated NaCl solution and then dried over anhydrous MgSO₄. The drying agent was removed by filtration and the filtrate was concentrated under reduced pressure. The resulting crude product was purified by silica gel column chromatography (EtOAc-heptane system) to obtain the title compound (920 mg). ¹H-NMR (400 MHz, CDCl₃) δ (ppm): 4.06 (s, 3H), 8.16 (dd, J=2.0, 8.0 Hz, 1H), 8.27 (d, J=8.0 Hz, 1H), 9.01 (d, J=2.0 Hz, 1H).

Synthesis of 5-cyanopyridine-2-carboxylic acid

A solution of the compound of Preparation Example 13-(1) (920 mg) and a 5 N NaOH solution (2.26 mL) in ethanol (30 mL) was stirred at RT for 10 min. 5 N hydrochloric acid (5.2 mL) was added to the reaction solution at RT, followed by extraction with EtOAc. The extract was dried over anhydrous MgSO₄. The drying agent was removed by filtration and the filtrate was concentrated under reduced pressure to obtain the title compound (800 mg). ¹H-NMR (400 MHz, DMSOd₆) δ (ppm): 8.18 (d, J=8.0 Hz, 1H), 8.51 (dd, J=2.0, 8.0 Hz, 1H), 9.12-9.18 (m, 1H).

Preparation Example 14

Synthesis of 5-difluoromethoxypyrazine-2-carboxylic acid

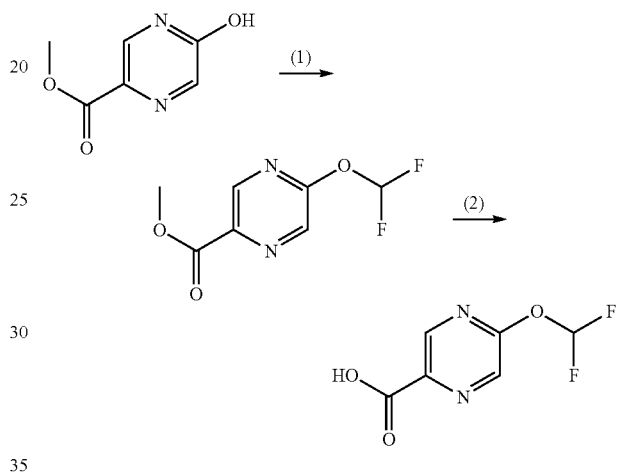

(1) Synthesis of methyl 5-difluoromethoxypyrazine-2-carbonxylate

Potassium carbonate (8.82 g) and sodium chlorodifluoroacetate (6.53 g) were added to a solution of a compound (CAS 13924-95-3) (3.3 g) in DMF (42.8 mL). The reaction solution was stirred at 100° C. for 30 min, and then saturated aqueous NH₄Cl was added, followed by extraction with EtOAc. The organic layer was washed with a saturated NaHCO₃ solution and a saturated NaCl solution and then dried over MgSO₄. The drying agent was removed by filtration and then the solvent was evaporated under reduced pressure. The residue was purified by silica gel column chromatography to obtain the title compound (928 mg). ¹H-NMR (400 MHz, CDCl₃) δ (ppm): 4.04 (s, 3H), 7.49 (t, J=71.2 Hz, 1H), 8.47 (d, J=0.8 Hz, 1H), 8.92 (d, J=0.8 Hz, 1H).

(2) Synthesis of 5-difluoromethoxypyrazine-2-carboxylic acid

Water (1.54 mL) and a 5 N NaOH solution (492 mL) were added to a solution of the compound obtained in Preparation Example 14-(1) (250 mg) in THF (4.60 mL). The reaction solution was stirred at RT for 5 min and then a 2 N hydrochloric acid solution was added, followed by extraction with EtOAc. The organic layers were washed with a saturated NaCl solution and then dried over MgSO₄. The drying agent was removed by filtration and then the solvent was concentrated under reduced pressure to obtain the title compound (200 mg). $^1$H-NMR (400 MHz, CDCl$_3$) δ (ppm): 7.51 (t, J=71.2 Hz, 1H), 8.39 (d, J=1.2 Hz, 1H), 9.04 (d, J=1.2 Hz, 1H).

Preparation Example 15

Synthesis of 5-fluoromethoxypyrazine-2-carboxylic acid

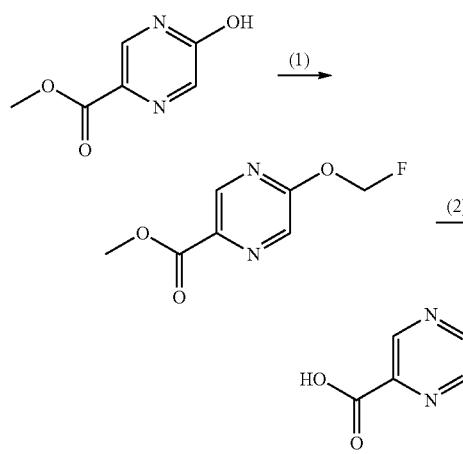

(1) Synthesis of methyl 5-fluoromethoxypyrazine-2-carboxylate

Fluoromethyl toluene-4-sulfonate (Journal of Labelled Compounds & Radiopharmaceuticals, 46 (6), 555-566; 2003) (344 mg) and cesium carbonate (824 mg) were added to a solution of methyl 5-hydroxypyrazine-2-carboxylate (130 mg) in DMF (2.0 mL). The reaction solution was stirred at 70° C. for 5 h and 30 min and then cooled to RT. Water was added to the reaction solution, followed by extraction with EtOAc. The organic layer was concentrated under reduced pressure. The residue was purified by NH-silica gel column chromatography to obtain the title compound (18.0 mg). $^1$H-NMR (400 MHz, CDCl$_3$) δ (ppm): 4.03 (s, 3H), 6.14 (d, J=51.2 Hz, 2H), 8.42 (d, J=1.2 Hz, 1H), 8.94 (d, J=1.2 Hz, 1H).

(2) Synthesis of 5-fluoromethoxypyrazine-2-carboxylic acid

Potassium trimethylsilanolate (18.6 mg) was added to a solution of methyl 5-fluoromethoxypyrazine-2-carboxylate obtained in Preparation Example 15-(1) (18.0 mg) in THF (1.0 mL). The reaction solution was stirred at RT for 1 h. Water and EtOAc were added to the reaction solution, and the aqueous layer was separated. The aqueous layer was made acidic with 1 M hydrochloric acid, followed by extraction with EtOAc. The organic layer was dried over anhydrous MgSO$_4$. The drying agent was removed by filtration and the filtrate was concentrated under reduced pressure to obtain a crude product of the title compound (10.2 mg). The compound was used for the next reaction without further purification. $^1$H-NMR (400 MHz, CDCl$_3$) δ (ppm): 6.16 (d, J=50.8 Hz, 2H), 8.34 (d, J=1.4 Hz, 1H), 9.05 (d, J=1.4 Hz, 1H).

Preparation Example 16

Synthesis of 5-fluoromethoxypyridine-2-carboxylic acid

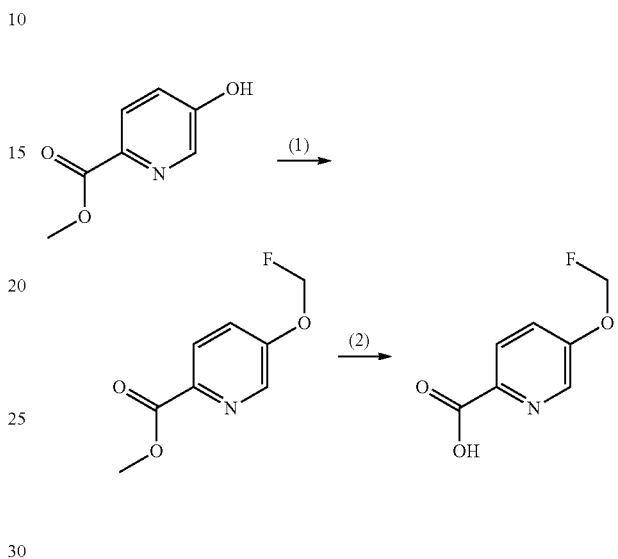

(1) Synthesis of methyl 5-fluoromethoxypyridine-2-carboxylate

A solution containing fluoromethyl toluene-4-sulfonate (233 mg) in DMF was added to a solution containing methyl 5-hydroxypyridine-2-carboxylate (100 mg) and cesium carbonate (532 mg) in DMF (5 mL). The reaction solution was stirred at 70° C. for 3 h. The reaction solution was cooled to RT. EtOAc and saturated aqueous NH$_4$Cl were added to the reaction solution, and the organic layer was separated. The organic layer was dried over anhydrous MgSO$_4$, and the insoluble matter was separated by filtration.

The filtrate was concentrated and the residue was purified by silica gel column chromatography to obtain the title compound (51 mg). $^1$H-NMR (CDCl$_3$) δ (ppm): 4.00 (s, 3H), 5.80 (d, J=45.1 Hz, 2H), 7.51 (ddd, J=0.8, 2.8, 8.8 Hz, 1H), 8.16 (d, J=0.4, 8.8 Hz, 1H), 8.54 (d, J=2.8 Hz, 1H).

(2) Synthesis of 5-fluoromethoxypyridine-2-carboxylic acid

N NaOH (81 μL) was added to a solution containing methyl 5-fluoromethoxypyridine-2-carboxylate (50 mg) in THF/water (2 mL, 3/1), and the mixture was stirred at RT for 10 min. Water (1 mL) was added to the reaction solution, followed by further stirring for 20 min. The reaction solution was made acidic with 5 N hydrochloric acid. EtOAc and a saturated NaCl solution were added to the reaction solution, and the organic layer was separated. The organic layer was dried over anhydrous MgSO$_4$, and the insoluble matter was separated by filtration. The filtrate was concentrated to obtain the title compound (22.6 mg). $^1$H-NMR (CDCl$_3$) δ (ppm): 5.81 (d, J=53.2 Hz, 2H), 7.61 (ddd, J=0.8, 2.8, 8.8 Hz, 1H), 8.25 (d, J=0.8, 8.8 Hz, 1H), 8.42 (d, J=2.4 Hz, 1H).

Preparation Example 17

Synthesis of 5-difluoromethylpyrazine-2-carboxylic acid

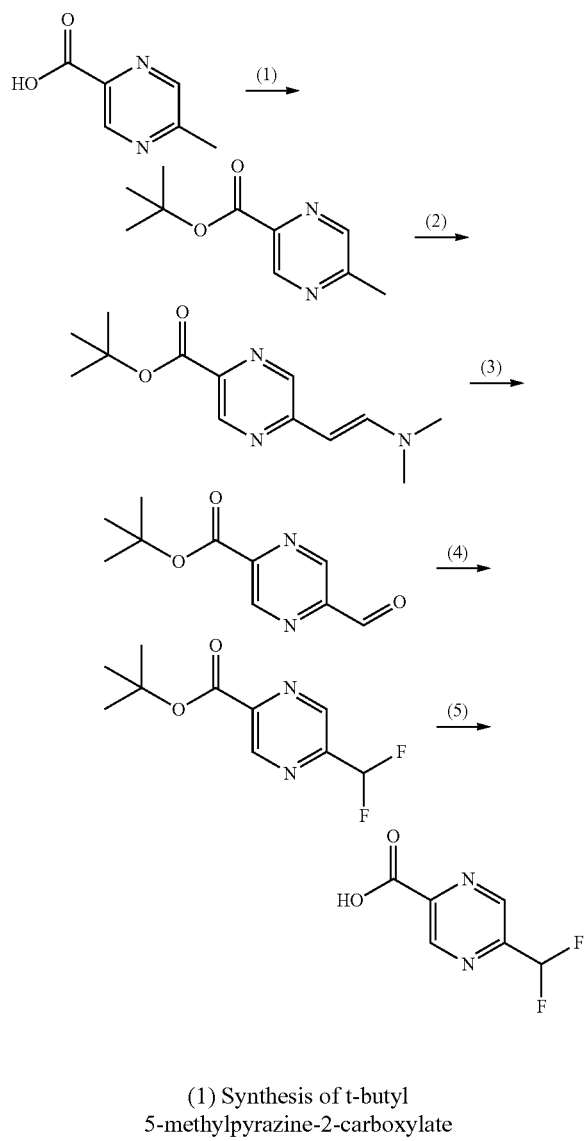

(1) Synthesis of t-butyl 5-methylpyrazine-2-carboxylate

A boron trifluoride-diethyl ether complex (91.7 μL) was added dropwise to a suspension of 2-methylpyrazine-5-carboxylic acid (1 g) and tert-butyl 2,2,2-trichloroacetimidate (4.75 g) in THF (20 mL) under ice-cooling. The reaction solution was warmed to RT, followed by stirring for 2 h. A saturated NaCl solution and EtOAc were added to the reaction solution, and the organic layer was separated. The organic layer was dried over anhydrous MgSO₄, and the insoluble matter was separated by filtration. The filtrate was concentrated and purified by silica gel column chromatography to obtain the title compound (1.4 g). ¹H-NMR (CDCl₃) δ (ppm): 1.65 (s, 9H), 2.65 (s, 3H), 8.57 (d, J=1.2 Hz, 1H), 9.10 (d, J=1.6 Hz, 1H).

(2) Synthesis of t-butyl 5-((E)-2-dimethylamino-vinyl)-pyrazine-2-carboxylate

A mixture of t-butyl 5-methylpyrazine-2-carboxylate (1.35 g), DMF (25 mL) and N,N-dimethylformamide dimethylacetal (25 mL) was stirred at 130° C. for 5 h. The reaction solution was cooled to RT and diluted with EtOAc. The mixture was washed with a saturated NaCl solution three times. The organic layer was dried over anhydrous MgSO₄, and the insoluble matter was separated by filtration. The filtrate was concentrated and the residue was purified by silica gel column chromatography to obtain the title compound (648 mg). ¹H-NMR (CDCl₃) δ (ppm): 1.63 (s, 9H), 3.00 (s, 6H), 5.16 (d, J=12.8 Hz, 1H), 7.72 (d, J=12.8 Hz, 1H), 8.16 (d, J=1.2 Hz, 1H), 8.81 (d, J=1.6 Hz, 1H).

(3) Synthesis of t-butyl 5-formylpyrazine-2-carboxylate

Sodium periodate (1.67 g) was added to a solution of t-butyl 5-((E)-2-dimethylamino-vinyl)-pyrazine-2-carboxylate (645 mg) in 50% THF-water (26 mL), and the mixture was stirred at RT for 4 h. A saturated NaHCO₃ solution and EtOAc were added to the reaction solution, and the organic layer was separated. The organic layer was washed with a saturated NaCl solution and dried over anhydrous MgSO₄. The insoluble matter was separated by filtration and the filtrate was concentrated. The residue was purified by silica gel column chromatography to obtain the title compound (249 mg). ¹H-NMR (CDCl₃) δ (ppm): 1.68 (s, 9H), 9.25 (d, J=1.2 Hz, 1H), 9.36 (d, J=1.6 Hz, 1H), 10.2 (s, 1H).

(4) Synthesis of t-butyl 5-difluoromethylpyrazine-2-carboxylate

[Bis(2-methoxyethyl)amino]sulfur trifluoride (662 μL) was added dropwise to a solution of t-butyl 5-formylpyrazine-2-carboxylate (249 mg) in CH₂Cl₂ (12 mL) under a N₂ atmosphere under ice-cooling. The reaction solution was stirred for 2 h while gradually returning to RT. A saturated NaHCO₃ solution and EtOAc were added to the reaction solution, and the organic layer was separated. The organic layer was washed with a saturated NaCl solution and dried over anhydrous MgSO₄. The insoluble matter was separated by filtration and the filtrate was concentrated. The residue was purified by silica gel column chromatography to obtain the title compound (175 mg). ¹H-NMR (CDCl₃) δ (ppm): 1.67 (s, 9H), 6.75 (t, J=54.4 Hz, 1H), 9.02 (d, J=0.8 Hz, 1H), 9.25 (d, J=0.8 Hz, 1H).

(5) Synthesis of 5-difluoromethylpyrazine-2-carboxylic acid

Trifluoroacetic acid (1 mL) was added to a solution of t-butyl 5-difluoromethylpyrazine-2-carboxylate (175 mg) in dichloromethane (1 mL), and the mixture was stirred at RT for 5 h. Ether and 5 N NaOH were added to the reaction solution. The aqueous layer was separated and made acidic with 5 N hydrochloric acid. EtOAc was added to the aqueous layer, and the organic layer was separated. The organic layer was dried over anhydrous MgSO₄, and the insoluble matter was separated by filtration. The filtrate was concentrated to obtain the title compound (100 mg).

$^1$H-NMR (CDCl$_3$) δ (ppm): 6.80 (t, J=54.4 Hz, 1H), 9.02 (s, 1H), 9.47 (s, 1H).
[No Preparation Examples 18 to 24]
Preparation Example 25
Synthesis of tert-butyl[(4aS,5S,7aS)-7a-(5-amino-2-fluorophenyl)-5-fluoromethyl-4-a,5,7,7a-tetrahydro-4H-furo[3,4-d][1,3]thiazin-2-yl]carbamate 25-(14)
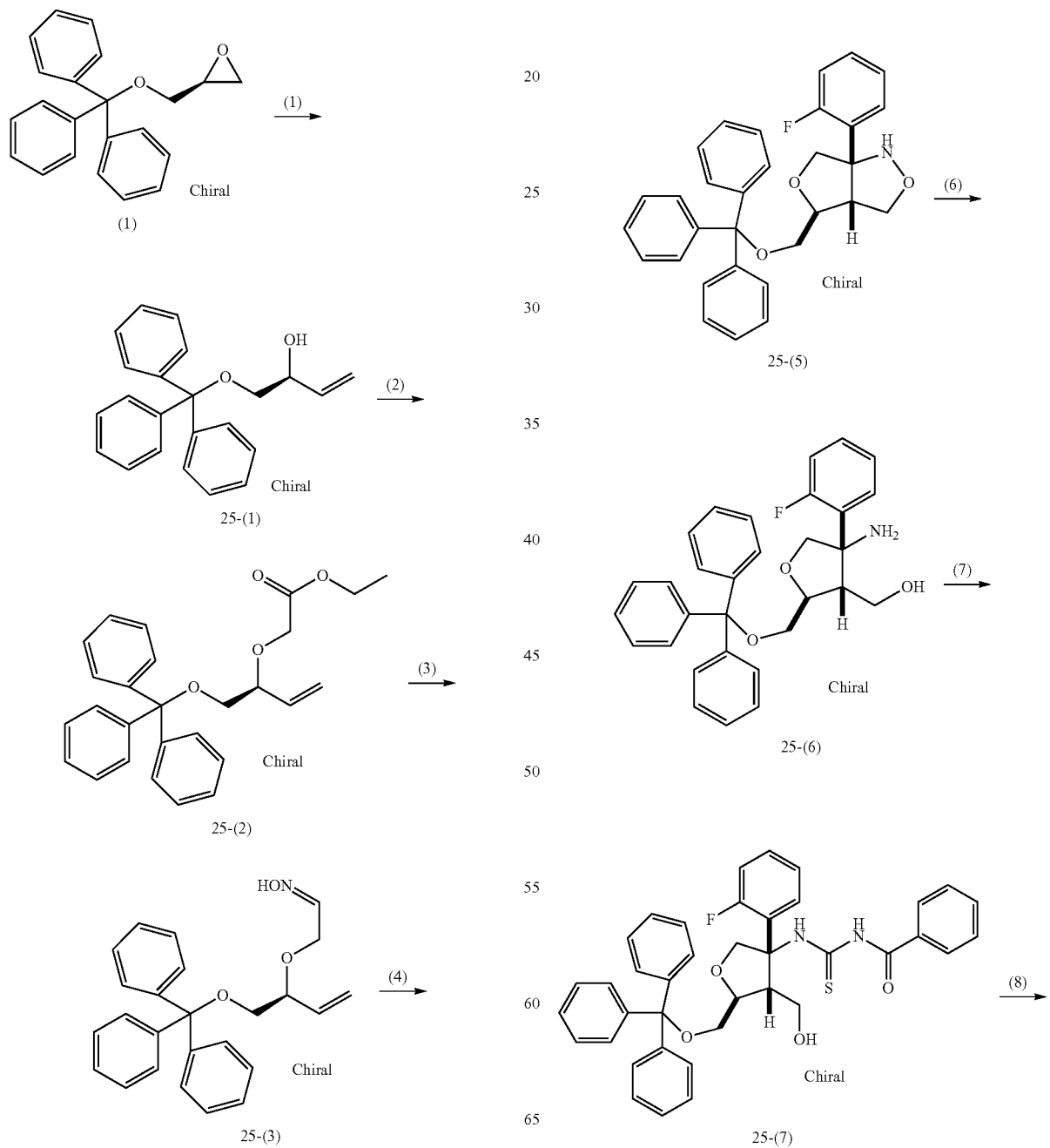

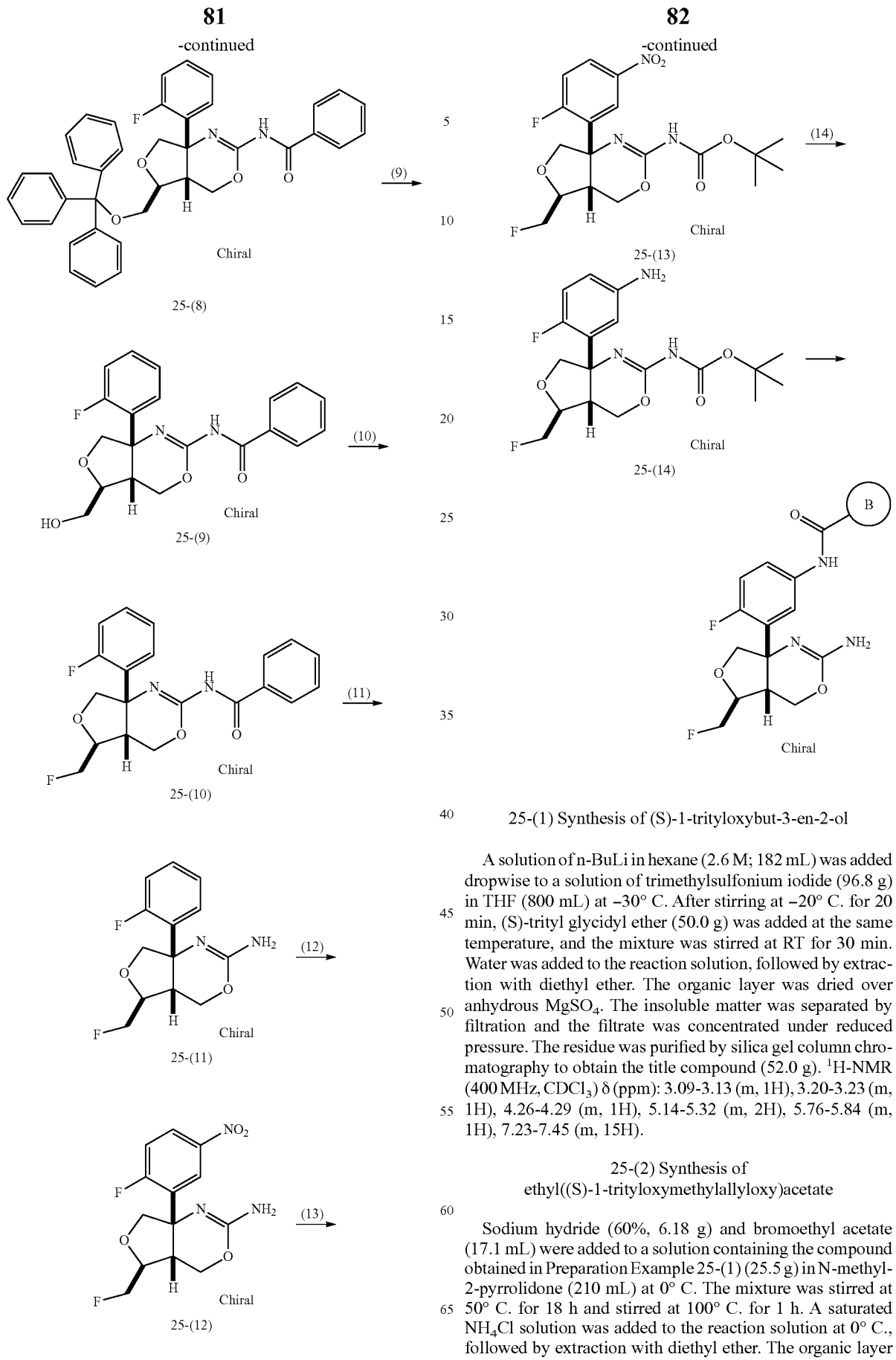

25-(1) Synthesis of (S)-1-trityloxybut-3-en-2-ol

A solution of n-BuLi in hexane (2.6 M; 182 mL) was added dropwise to a solution of trimethylsulfonium iodide (96.8 g) in THF (800 mL) at −30° C. After stirring at −20° C. for 20 min, (S)-trityl glycidyl ether (50.0 g) was added at the same temperature, and the mixture was stirred at RT for 30 min. Water was added to the reaction solution, followed by extraction with diethyl ether. The organic layer was dried over anhydrous $MgSO_4$. The insoluble matter was separated by filtration and the filtrate was concentrated under reduced pressure. The residue was purified by silica gel column chromatography to obtain the title compound (52.0 g). $^1$H-NMR (400 MHz, $CDCl_3$) δ (ppm): 3.09-3.13 (m, 1H), 3.20-3.23 (m, 1H), 4.26-4.29 (m, 1H), 5.14-5.32 (m, 2H), 5.76-5.84 (m, 1H), 7.23-7.45 (m, 15H).

25-(2) Synthesis of ethyl((S)-1-trityloxymethylallyloxy)acetate

Sodium hydride (60%, 6.18 g) and bromoethyl acetate (17.1 mL) were added to a solution containing the compound obtained in Preparation Example 25-(1) (25.5 g) in N-methyl-2-pyrrolidone (210 mL) at 0° C. The mixture was stirred at 50° C. for 18 h and stirred at 100° C. for 1 h. A saturated $NH_4Cl$ solution was added to the reaction solution at 0° C., followed by extraction with diethyl ether. The organic layer was dried over anhydrous MgSO$_4$. The insoluble matter was separated by filtration and the filtrate was concentrated. The residue was purified by silica gel column chromatography to obtain the title compound (15.5 g). $^1$H-NMR (400 MHz, CDCl$_3$) δ (ppm): 1.32 (t, J=7.2 Hz, 3H), 3.13-3.17 (m, 1H), 3.31-3.35 (m, 1H), 3.98-4.27 (m, 5H), 5.28-5.33 (m, 2H), 5.74-5.76 (m, 1H), 7.20-7.47 (m, 15H).

25-(3) Synthesis of ((S)-1-trityloxymethylallyloxy)acetaldehyde oxime

A solution of diisobutylaluminum hydride in toluene (1.0 M; 55.2 mL) was added dropwise to a solution containing the compound obtained in Preparation Example 25-(2) (15.5 g) in CH$_2$Cl$_2$ (74.0 mL) at −78° C. The mixture was stirred at the same temperature for 30 min. A 2 N hydrochloric acid solution was added to the reaction solution, followed by extraction with CH$_2$Cl$_2$. The organic layer was washed with a saturated NaHCO$_3$ solution and dried over anhydrous MgSO$_4$. The insoluble matter was separated by filtration and the filtrate was concentrated. Methanol (70.0 mL), sodium acetate (6.04 g) and hydroxylamine hydrochloride (3.84 g) were added to the residue at RT, and the mixture was stirred at the same temperature for 15 min. EtOAc and water were added to the reaction solution, and the organic layer was separated and dried over anhydrous MgSO$_4$. The insoluble matter was separated by filtration and the filtrate was concentrated. The residue was purified by silica gel column chromatography to obtain the title compound (11.3 g). $^1$H-NMR (400 MHz, CDCl$_3$) δ (ppm): 3.08-3.12 (m, 1H), 3.24-3.26 (m, 1H), 3.81-4.42 (m, 3H), 5.23-5.30 (m, 2H), 5.70-5.72 (m, 1H), 6.95-6.96 (m, 0.5H), 7.21-7.47 (m, 15H), 7.52-7.53 (m, 0.5H).

25-(4) Synthesis of (3aR,4S)-4-trityloxymethyl-3a,4-dihydro-3H,6H-furo[3,4-c]isoxazole A 5% sodium hypochlorite solution (52.2 mL) was added dropwise to a solution containing the compound obtained in Preparation Example 25-(3) (11.3 g) in CH$_2$Cl$_2$ (100 mL) at 0° C., and the mixture was stirred at 0° C. for 30 min. A sodium bisulfite solution was added to the reaction solution at the same temperature. The organic layer was separated and dried over anhydrous MgSO$_4$. The insoluble matter was separated by filtration and the filtrate was concentrated. The residue was purified by silica gel column chromatography to obtain the title compound (5.20 g). $^1$H-NMR (400 MHz, CDCl$_3$) δ (ppm): 3.21-3.35 (m, 1H), 3.37-3.40 (m, 1H), 3.93-4.07 (m, 3H), 4.47-4.57 (m, 3H), 7.23-7.42 (m, 15H).

25-(5) Synthesis of (3aR,4S,6aS)-6a-(2-fluorophenyl)-4-trityloxymethyltetrahydrofuro[3,4-c]isoxazole A solution of n-butyllithium in hexane (2.60 M; 10.4 mL) was added dropwise to a solution containing 2-bromofluorobenzene (2.93 mL) in THF/toluene (10.8 mL/108 mL) under a N$_2$ atmosphere at −78° C. The reaction solution was stirred at the same temperature for 10 min. A boron trifluoride-diethyl ether complex (3.33 mL) and a solution containing the compound obtained in Preparation Example 25-(4) (5.20 g) in toluene (50 mL) were added dropwise to the reaction solution sequentially at the same temperature. After stirring at the same temperature for 40 min, aqueous NH$_4$Cl was added to the reaction solution, followed by warming to RT. Water and EtOAc were added to the reaction solution, and the organic layer was separated. The organic layer was washed with a saturated NaCl solution. The organic layer was dried over anhydrous MgSO$_4$, and the insoluble matter was separated by filtration. The filtrate was concentrated and the residue was purified by silica gel column chromatography to obtain the title compound (6.23 g). $^1$H-NMR (400 MHz, CDCl$_3$) δ (ppm): 3.24-3.49 (m, 3H), 3.91-3.98 (m, 2H), 4.07-4.35 (m, 3H), 7.00-7.62 (m, 19H).

25-(6) Synthesis of [(2S,3R,4S)-4-amino-4-(2-fluorophenyl)-2-trityloxymethyl-tetrahydrofuran-3-yl]methanol Zinc powder (8.44 g) was added to a solution containing the compound obtained in Preparation Example 25-(5) (6.22 g) in acetic acid (50.0 mL) at RT. The reaction solution was stirred at RT for 18 h. The insoluble matter was separated by filtration through celite and the filtrate was concentrated. EtOAc and a NaHCO$_3$ solution were added to the residue, and the organic layer was separated. The organic layer was washed with saturated aqueous NaCl and dried over anhydrous MgSO$_4$. The insoluble matter was separated by filtration and the filtrate was concentrated under reduced pressure. The residue was purified by column silica gel chromatography to obtain the title compound (4.10 g). $^1$H-NMR (400 MHz, CDCl$_3$) δ (ppm): 2.63-2.65 (m, 1H), 3.24-3.31 (m, 2H), 3.61-3.65 (m, 1H), 3.92-3.97 (m, 2H), 4.15-4.26 (m, 1H), 4.37-4.41 (m, 1H), 7.00-7.52 (m, 19H).

25-(7) Synthesis of 1-benzoyl-3-[(3S,4R,5S)-3-(2-fluorophenyl)-4-hydroxymethyl-5-trityloxymethyl-tetrahydrofuran-3-yl]thiourea Benzoyl isothiocyanate (1.37 mL) was added to a solution containing the compound obtained in Preparation Example 25-(6) (4.10 g) in CH$_2$Cl$_2$ (16.0 mL), and the mixture was stirred at RT for 10 min. The reaction solution was concentrated under reduced pressure. The residue was purified by silica gel column chromatography to obtain the title compound (4.32 g). $^1$H-NMR (400 MHz, CDCl$_3$) δ (ppm): 3.19-3.36 (m, 3H), 3.79-4.05 (m, 3H), 4.57-4.58 (m, 2H), 7.03-7.89 (m, 24H), 8.89 (br, 1H).

25-(8) Synthesis of N-[(4aR,5S,7aS)-7a-(2-fluorophenyl)-5-trityloxy-4a,5,7,7a-tetrahydro-4H-furo[3,4-d][1,3]oxazin-2-yl]benzamide N,N'-dicyclohexylcarbodiimide (1.00 g) was added to a solution containing the compound obtained in Preparation Example 25-(7) (2.20 g) in EtOH (35 mL). The reaction was then warmed to 80° C. and stirred at this temperature for 6 h. The reaction solution was then concentrated under reduced pressure. The residue was purified by silica gel column chromatography (0 to 100% EtOAc in hexanes) to obtain the title compound (1.46 g). $^1$H-NMR (400 MHz, CDCl$_3$) δ (ppm): 3.13-3.18 (m, 1H), 3.31-3.38 (m, 2H), 4.05-4.09 (m, 1H), 4.16-4.24 (m, 2H), 4.35-4.41 (m, 2H), 7.05-7.45 (m, 22H), 8.15-8.18 (m, 2H), 11.90 (br, 1H).

25-(9) Synthesis of N-[(4aR,5S,7aS)-7a-(2-fluorophenyl)-5-hydroxymethyl-4a,5,7,7a-tetrahydro-4H-furo[3,4-d][1,3]oxazin-2-yl]benzamide The compound obtained in Preparation Example 25-(8) (1.29 g) was dissolved in formic acid (13 mL) and the solution was allowed to stir at RT overnight. The reaction mixture was then concentrated under reduced pressure. The residue was purified by silica gel column chromatography (10 to 100% EtOAc in hexanes) to obtain the title compound (0.63 g).

¹H-NMR (400 MHz, CDCl₃) δ (ppm): 2.00-2.04 (m, 1H), 3.32 (br d, J 8.3 Hz, 1H), 3.80-3.85 (m, 1H), 3.95-4.00 (m, 1H), 4.18 (dd, J=3.0, 9.6 Hz, 1H), 4.32-4.51 (m, 4H), 7.16-7.28 (m, 2H), 7.39-7.57 (m, 5H), 8.24-8.27 (m, 2H), 12.05 (br s, 1H).

25-(10) Synthesis of N-[(4aR,5S,7aS)-5-fluoromethyl-7a-(2-fluorophenyl)-4a,5,7,7a-tetrahydro-4H-furo[3,4-d][1,3]oxazin-2-yl]benzamide The compound obtained in Preparation Example 25-(9) (600 mg) was dissolved in dry THF (13 mL) under a N₂ atmosphere at 0° C. Triethylamine (1.35 mL, 9.76 mmol), triethylamine trihydrofluoride (0.53 mL, 3.25 mmol) and 1,1,2,2,3,3,4,4,4-nonafluorobutane-1-sulfonyl fluoride (0.58 mL, 3.23 mmol) were added and the reaction was warmed to RT and stirred for 2 h. The reaction mixture was partitioned between EtOAc (50 mL) and sat. sodium bicarbonate (100 mL). The aqueous phase was extracted with EtOAc (50 mL) and the combined organic phase was dried over MgSO₄ and the solvent removed in vacuo. The residue was purified by silica gel column chromatography using a 10% EtOAc in hexane to 100% EtOAc gradient to afford the title compound (474 mg). ¹H-NMR (400 MHz, CDCl₃) δ (ppm): 3.35 (br d, J=7.6 Hz, 1H), 4.17 (dd, J=2.8, 9.6 Hz, 1H), 4.33-4.43 (m, 2H), 4.48-4.66 (m, 3H), 4.70-4.78 (m, 1H), 7.16-7.30 (m, 2H), 7.41-7.59 (m, 5H), 8.26 (d, J=7.3 Hz, 2H), 12.05 (br s, 1H).

25-(11) Synthesis of (4aR,5S,7aS)-5-fluoromethyl-7a-(2-fluorophenyl)-4a,5,7,7a-tetrahydro-4H-furo[3,4-d][1,3]oxazin-2-ylamine The compound obtained in Preparation Example 25-(10) (465 mg) was dissolved in methanol (5 mL), 1,8-diazabicyclo[5.4.0]undec-7-ene (509 mg) was added, and the solution was heated to gentle reflux (heating block temperature 65° C.). After 16 h, the reaction mixture was concentrated under reduced pressure, and the residue purified by silica gel column chromatography (10% to 60% EtOAc in hexanes) to afford the title compound (298 mg). ¹H-NMR (400 MHz, CDCl₃) δ (ppm): 2.94 (dt, J 2.3, 8.1 Hz, 1H), 3.83 (dd, J=3.0, 8.3 Hz, 1H), 3.97 (dd, J 2.5, 11.4 Hz, 1H), 4.04 (dd, J 1.8, 11.4 Hz, 1H), 4.30 (br s, 2H), 4.51-4.72 (m, 2H), 7.06 (ddd, J=13.6, 8.1, 1.1 Hz, 1H) 7.18 (td, J=7.5, 1.1 Hz, 1H) 7.24-7.34 (m, 1H) 7.67 (td, J=8.1, 1.8 Hz, 1H).

25-(12) Synthesis of (4aR,5S,7aS)-5-(fluoromethyl)-7a-(2-fluoro-5-nitrophenyl)-4a,5,7,7a-tetrahydro-4H-furo[3,4-d][1,3]oxazin-2-amine The compound obtained in Preparation Example 25-(11) (315 mg) was dissolved in TFA (2 mL), and the solution was cooled to 0° C. Sulfuric acid (conc., 0.50 mL) was added, followed by fuming nitric acid (56 µL) dropwise. After stirring at 0° C. for 45 mins, the reaction mixture was poured onto ice (25 g) and basified to pH 12 with 5N NaOH (aq.). After allowing the ice to melt, the mixture was extracted with EtOAc (3×25 mL), and the combined organic portions dried over MgSO₄ and evaporated to afford the title compound (464 mg) which was used in the subsequent step without purification. ¹H NMR (400 MHz, CDCl₃) δ ppm 2.80 (br d, J=7.8 Hz, 1H) 3.67 (dd, J=8.6, 2.5 Hz, 1H) 3.79 (dd, J=11.7, 2.4 Hz, 1H) 3.88-3.92 (m, 1H) 4.14-4.29 (m, 2H) 4.37 (d, J=4.3 Hz, 1H) 4.49 (d, J=4.3 Hz, 1H) 7.03 (dd, J=9.1, 10.9 Hz, 1H), 8.01 (ddd, J 3.0, 4.0, 8.8 Hz, 1H) 8.43 (dd, J=6.8, 3.0 Hz, 1H)

25-(13) Synthesis of tert-butyl[(4aR,5S,7aS)-5-fluoromethyl-7a-(2-fluoro-5-nitrophenyl)-4a,5,7,7a-tetrahydro-4H-furo[3,4-d][1,3]oxazin-2-yl]carbamate The compound obtained in Preparation Example 25-(12) (464 mg) was dissolved in DCM (10 mL), and triethylamine (355 mg) and di-tert-butyl dicarbonate (460 mg) was added. After stirring for 16 h, further portions of triethylamine (100 mg) and di-tert-butyl dicarbonate (100 mg) were added. After stirring for a further 4 h, the reaction mixture was concentrated under reduced pressure and the residue purified by silica gel column chromatography to afford the title compound (169 mg). ¹H NMR (400 MHz, CDCl₃) δ ppm 1.51 (s, 9H) 3.16 (br s, 1H) 3.99 (br s, 1H) 4.14 (br s, 1H) 4.28 (d, J=11.9 Hz, 1H), 4.40-4.51 (m, 2H), 4.53-4.64 (m, 1H) 4.65-4.76 (m, 1H) 7.28 (t, J=9.7 Hz, 1H) 8.18-8.34 (m, 1H) 8.44-8.62 (m, 1H).

25-(14) Synthesis of tert-butyl[(4aR,5S,7aS)-7a-(5-amino-2-fluorophenyl)-5-fluoromethyl-4a,5,7,7a-tetrahydro-4H-furo[3,4-d][1,3]oxazin-2-yl]carbamate The compound obtained in Preparation Example 25-(13) (169 mg) was dissolved in ethanol (5 mL) and tin chloride dihydrate (277 mg) was added. After stirring for 18 h, the solution was poured onto NaOH (2N aq., 20 mL), and the resulting mixture was extracted with EtOAc (2×40 mL). The combined organic portions were dried over MgSO₄ and evaporated to afford the title compound (150 mg). ¹H NMR (400 MHz, CDCl₃) δ ppm 1.43 (m, 9H) 3.09 (d, J=7.8 Hz, 1H) 3.64 (br s, 2H) 3.90 (dd, J=9.6, 2.8 Hz, 2H), 4.10-4.20 (m, 2H), 4.32-4.43 (m, 2H) 4.43-4.53 (m, 1H) 4.54-4.66 (m, 1H) 6.50-6.58 (m, 1H) 6.67 (d, J=6.6, 2.8 Hz, 1H) 6.86 (dd, J=8.8, 11.9 Hz, 1H).

Preparation Example 26

Synthesis of tert-butyl[(4aS,5S,7aS)-7a-(5-amino-2-fluorophenyl)-5-trifluoromethyl-4a,5,7,7a-tetrahydro-4H-furo[3,4-d][1,3]thiazin-2-yl]carbamate

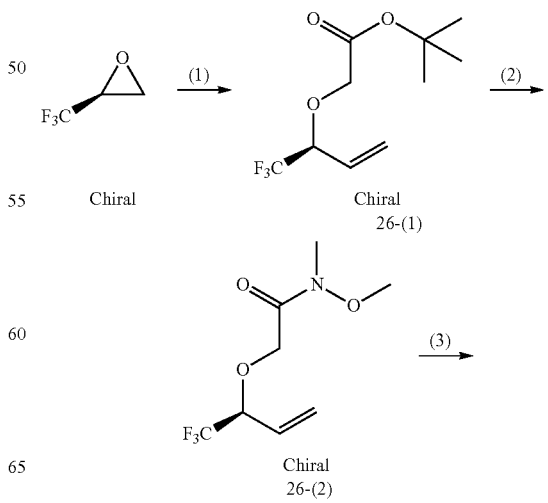

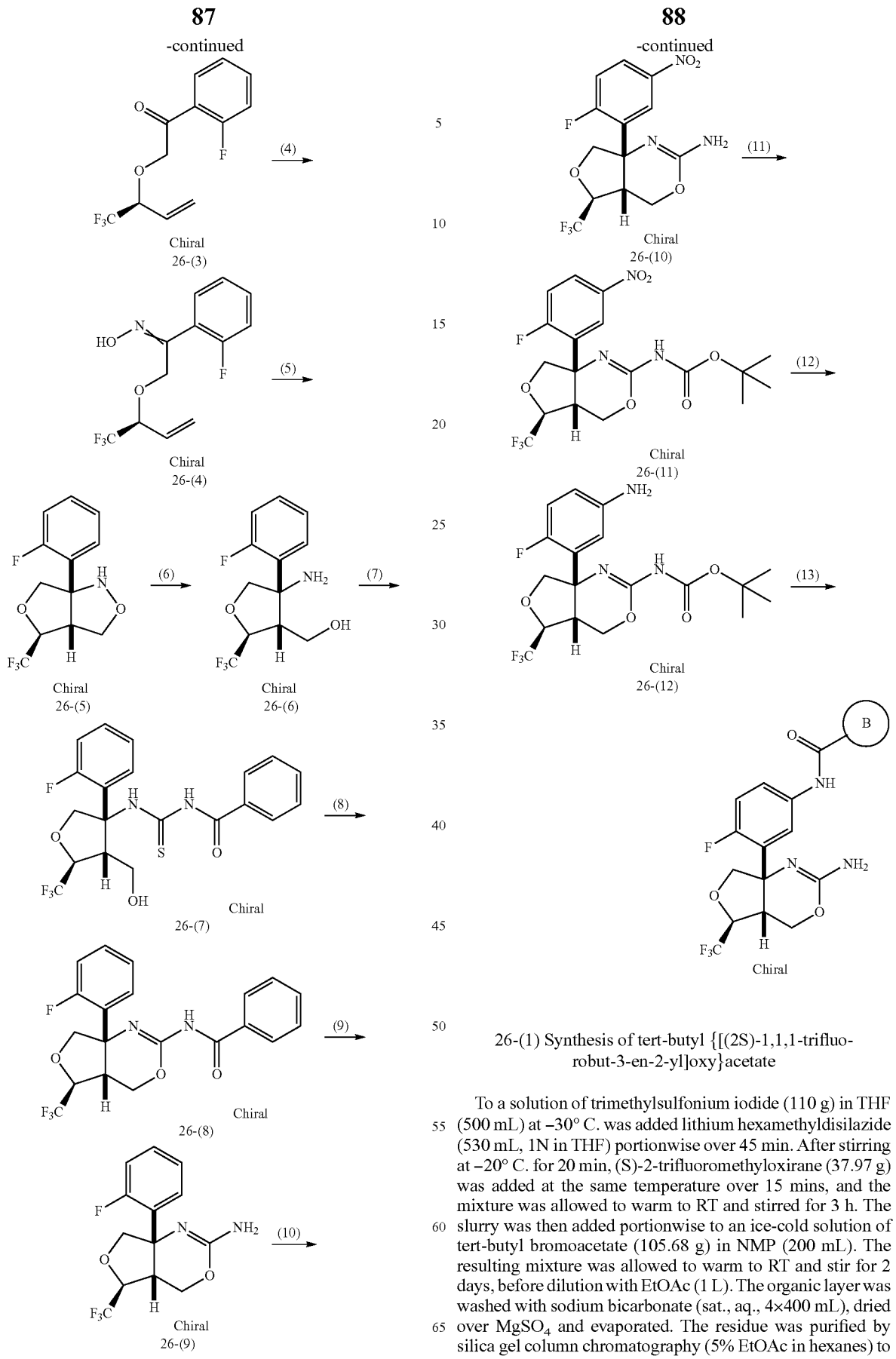

26-(1) Synthesis of tert-butyl {[(2S)-1,1,1-trifluorobut-3-en-2-yl]oxy}acetate

To a solution of trimethylsulfonium iodide (110 g) in THF (500 mL) at −30° C. was added lithium hexamethyldisilazide (530 mL, 1N in THF) portionwise over 45 min. After stirring at −20° C. for 20 min, (S)-2-trifluoromethyloxirane (37.97 g) was added at the same temperature over 15 mins, and the mixture was allowed to warm to RT and stirred for 3 h. The slurry was then added portionwise to an ice-cold solution of tert-butyl bromoacetate (105.68 g) in NMP (200 mL). The resulting mixture was allowed to warm to RT and stir for 2 days, before dilution with EtOAc (1 L). The organic layer was washed with sodium bicarbonate (sat., aq., 4×400 mL), dried over $MgSO_4$ and evaporated. The residue was purified by silica gel column chromatography (5% EtOAc in hexanes) to obtain the title compound (70.1 g) which was used in the subsequent step without purification. ¹H-NMR (400 MHz, CDCl₃) δ (ppm): 1.30 (s, 9H) 3.83-3.96 (m, 2H) 4.14-4.21 (m, 1H) 5.34-5.48 (m, 2H) 5.56-5.71 (m, 1H)

26-(2) Synthesis of (S)—N-methoxy-N-methyl-2-((1,1,1-trifluorobut-3-en-2-yl)oxy)acetamide The compound obtained in Preparation Example 26-(1) (70.1 g, crude) was dissolved in ice-cold formic acid (200 mL). The mixture was allowed to warm to RT and stir overnight. The reaction mixture was then concentrated under reduced pressure, toluene (200 mL) was added, the mixture concentrated, before a second addition of toluene (200 mL) and concentration to an oil. The residue was dissolved in DCM (600 mL), cooled in an ice-bath, and N,N'-carbonyl diimidazole (35 g) was added portionwise over 20 mins. After stirring for 45 mins, N,O-dimethyl hydroxylamine hydrochloride (22 g) was added, and the reaction mixture was allowed to warm to RT and stir overnight. Saturated NaHCO₃ (500 mL) and brine (250 mL) were then added, and the mixture extracted with EtOAc (3×750 mL). The combined organic portions were dried over MgSO₄ and evaporated. The residue was purified by silica gel column chromatography (1% to 30% EtOAc in hexanes) to obtain the title compound (25.17 g).
¹H-NMR (400 MHz, CDCl₃) δ (ppm) 3.21 (s, 3H), 3.71 (m, 3H), 4.36-4.51 (m, 3H), 5.54-5.69 (m, 2H), 5.84 (ddd, J=17.7, 10.4, 7.3 Hz, 1H)

26-(3) Synthesis of (S)-1-(2-fluorophenyl)-2-((1,1,1-trifluorobut-3-en-2-yl)oxy)ethanone A solution of n-butyllithium in hexane (2.50 M; 90 mL) was added dropwise over 25 mins to a solution containing 2-bromofluorobenzene (40.35 g) in THF (250 mL) under a N₂ atmosphere at −78° C. The reaction solution was allowed to warm to −60° C. and stir for 60 min. The compound obtained in Preparation Example 26-(2) (40 g) in THF (25 mL) was added dropwise to the reaction solution, and after stirring at −60° C. for 2 h, aqueous NH₄Cl (100 mL) was added to the reaction solution, followed by warming to RT. Brine (200 mL) was added to the reaction solution, and the mixture was extracted with EtOAc (3×400 mL). The combined organic portions were dried over MgSO₄, evaporated, and the residue was purified by silica gel column chromatography (1% to 10% EtOAc in hexanes) to obtain the title compound (33.59 g). ¹H-NMR (400 MHz, CDCl₃) δ (ppm): 4.40 (pentet, J=6.3 Hz, 1H) 4.81-4.87 (m, 2H), 5.54-5.69 (m, 2H), 5.86 (ddd, J 17.4, 10.4, 7.3 Hz, 1H) 7.12-7.22 (m, 1H) 7.24-7.34 (m, 1H) 7.54-7.63 (m, 1H) 7.94-8.02 (m, 1H).

26-(4) Synthesis of (S)-1-(2-fluorophenyl)-2-((1,1,1-trifluorobut-3-en-2-yl)oxy)ethanone oxime The compound obtained in Preparation Example 26-(3) (41.22 g) was dissolved in anhydrous methanol (400 mL) and hydroxylamine hydrochloride (14.0 g) and sodium acetate (19.0 g) were added. The reaction mixture was heated to 50° C. for 90 min, then cooled to RT, concentrated in vacuo and the residue purified by silica gel chromatography (2% to 15% EtOAc in hexanes) to afford the title compound as a mixture of geometric isomers. ¹H-NMR (400 MHz, CDCl₃) δ (ppm): 4.04-4.15 (m, 0.8H), 4.18-4.26 (s, 0.2H), 4.44-4.57 (m, 0.4H) 4.79-4.90 (m, 1.6H) 5.37-5.56 (m, 2H) 5.64-5.78 (m, 1H) 7.03-7.26 (m, 2H) 7.33-7.54 (m, 2H), 7.90 (bs s, 0.2H), 8.51 (br s, 0.8H).

26-(5) Synthesis of (3aR,4S)-4-(trifluoromethyl)-3,3a,4,6-tetrahydrofuro[3,4-c]isoxazole The compound obtained in Preparation Example 26-(4) (40.54 g) was dissolved in xylenes (400 mL) and hydroquinone (4.0 g) was added. The reaction mixture was heated to reflux (heating block temperature 140° C.) for 22 hrs, then cooled and evaporated. The residue was purified by silica gel column chromatography (1% to 30% EtOAc in hexanes) to obtain the title compound (28.76 g). ¹H-NMR (400 MHz, CDCl₃) δ (ppm): 3.71-3.81 (m, 1H), 4.04-4.35 (m, 3H), 4.51-4.62 (m, 1H), 5.38-5.54 (m, 1H), 7.07-7.26 (m, 2H), 7.32-7.42 (m, 1H), 7.54-7.67 (m, 1H).

26-(6) Synthesis of ((2S,3R,4S)-4-amino-4-(2-fluorophenyl)-2-(trifluoromethyl)tetrahydrofuran-3-yl)methanol The compound obtained in Preparation Example 26-(5) (28.76 g) was dissolved in acetic acid (200 mL) and the reaction mixture cooled to 0° C. Zinc (50 g) was added, and the reaction was allowed to warm and stir at RT. The reaction mixture was then diluted with EtOAc (500 mL) and filtered through celite, washing with a further 500 mL of EtOAc. The combined organic portions were evaporated, dissolved in chloroform (200 mL), and ammonia (28% aq., 250 mL) was added slowly. The layers were separated, and the aqueous portion was further extracted with chloroform (2×250 mL). The combined organic extracts were dried over anhydrous MgSO₄ and evaporated to afford the title compound (31.12 g) which was used in the subsequent step without further purification. ¹H-NMR (400 MHz, CDCl₃) δ (ppm): 2.93 (ddd, J=7.7, 4.9, 2.5 Hz, 1H), 3.84 (dd, J=12.4, 4.8 Hz, 1H), 4.05 (dd, J=9.2, 3.2 Hz, 1H), 4.17 (dd, J=12.4, 2.3 Hz, 1H), 4.31 (d, J=9.3 Hz, 1H), 4.72 (quin, J=7.3 Hz, 1H), 7.13 (ddd, J=13.1, 8.8, 1.3 Hz, 1H), 7.22 (td, J=7.6, 1.3 Hz, 1H), 7.31-7.40 (m, 1H), 7.51 (td, J=8.0, 1.6 Hz, 1H)

26-(7) Synthesis of N-(((3S,4R,5S)-3-(2-fluorophenyl)-4-(hydroxymethyl)-5-(trifluoromethyl)tetrahydrofuran-3-yl)carbamothioyl)benzamide Benzoyl isothiocyanate (19.0 mL) was added to a solution containing the compound obtained in Preparation Example 26-(6) (28.72 g) in DCM (150 mL), and the mixture was stirred at RT for 18 h. Sodium bicarbonate (sat., aq., 200 mL) was then added, the mixture extracted with EtOAc (3×300 mL), dried over MgSO₄ and concentrated under reduced pressure. The residue was purified by silica gel column chromatography (5% to 30% EtOAc in hexanes) to obtain the title compound (37.07 g). ¹H-NMR (400 MHz, CDCl₃) δ (ppm): 3.22 (dd, J=8.1, 4.5 Hz, 1H), 3.31 (td, J=8.0, 3.0 Hz, 1H), 3.94-4.07 (m, 1H), 4.31-4.46 (m, 1H), 4.53 (d, J=9.9 Hz, 1H), 4.83 (d, J=9.9 Hz, 1H), 6.97-7.14 (m, 1H), 7.22 (td, J=7.7, 1.3 Hz, 1H), 7.31-7.45 (m, 1H), 7.49-7.61 (m, 2H), 7.61-7.70 (m, 1H), 7.75 (td, J=8.1, 1.5 Hz, 1H), 7.79-7.93 (m, 2H), 8.90 (s, 1H), 11.85 (s, 1H)

26-(8) Synthesis N-((4aR,5S,7aS)-7a-(2-fluorophenyl)-5-(trifluoromethyl)-4a,5,7,7a-tetrahydro-4H-furo[3,4-d][1,3]oxazin-2-yl)benzamide The compound obtained in Preparation Example 26-(7) (31.1 g) was dissolved in pyridine (150 mL), and the mixture cooled to −20° C. Trifluoromethanesulfonic anhydride (14.0 mL) was added dropwise over 30 min and the reaction was allowed to warm to 0° C. After stirring for 2 h, the reaction was quenched by the addition of ammonium chloride (sat., aq., 400 mL) and extracted with EtOAc (3×500 mL). The combined organic extracts were dried over MgSO$_4$, concentrated in vacuo and purified by silica gel column chromatography (2% to 30% EtOAc/hex) to obtain the title compound (6.88 g, purity about 50%). $^1$H-NMR (400 MHz, CDCl$_3$) δ (ppm): 3.54-3.59 (m, 1H), 4.18-4.24 (m, 1H), 4.30-4.72 (m, 4H), 7.16-7.33 (m, 2H), 7.41-7.59 (m, 5H), 7.82-7.91 (m, 1H), 8.23-8.27 (m, 1H)

26-(9) Synthesis of (4aR,5S,7aS)-7a-(2-fluorophenyl)-5-(trifluoromethyl)-4a,5,7,7a-tetrahydro-4H-furo[3,4-d][1,3]oxazin-2-amine The compound obtained in Preparation Example 26-(8) (8.28 g, crude material of purity around 50%) was dissolved in methanol (30 mL), 1,8-diazabicyclo[5.4.0]undec-7-ene (3.38 g) was added, and the solution was heated to reflux (heating block temperature 80° C.). After 16 h, the reaction mixture was concentrated under reduced pressure, and the residue purified by silica gel column chromatography (10% to 60% EtOAc in hexanes) to afford the title compound (3.91 g). $^1$H-NMR (400 MHz, CDCl$_3$) δ (ppm): 3.29 (d, J=7.6 Hz, 1H), 3.88 (dd, J=8.2, 2.4 Hz, 1H), 3.94-4.02 (m, 1H), 4.02-4.26 (m, 3H), 4.50 (quin, J=7.3 Hz, 1H), 4.58 (d, J=8.1 Hz, 1H), 7.07 (ddd, J=12.5, 8.1, 1.1 Hz, 1H), 7.16-7.23 (m, 1H), 7.24-7.37 (m, 1H), 7.60-7.71 (m, 1H)

26-(10) Synthesis of (4aR,5S,7aS)-7a-(2-fluoro-5-nitrophenyl)-5-(trifluoromethyl)-4-a,5,7,7a-tetrahydro-4H-furo[3,4-d][1,3]oxazin-2-amine The compound obtained in Preparation Example 26-(9) (5.15 g) was dissolved in TFA (40 mL), and the solution was cooled to 0° C. Sulfuric acid (conc., 8 mL) was added, followed by fuming nitric acid (824 μL) dropwise. After stirring at 0° C. for 90 mins, the reaction mixture was poured onto ice (200 g) and basified to pH 12 with 2N NaOH (aq.). After allowing the ice to melt, the mixture was extracted with EtOAc (3×250 mL), and the combined organic portions dried over MgSO$_4$ and evaporated to afford the title compound (8.12 g) which was used in the subsequent step without purification.
$^1$H NMR (400 MHz, CDCl$_3$) δ ppm 3.31 (d, J=6.8 Hz, 1H), 3.85-4.04 (m, 2H), 4.30 (br s, 1H), 4.47-4.59 (m, 2H), 7.21-7.27 (m, 1H), 8.20-8.29 (m, 1H), 8.67 (dd, J=6.7, 2.9 Hz, 1H)

26-(11) Synthesis of tert-butyl((4aR,5S,7aS)-7a-(2-fluoro-5-nitrophenyl)-5-(trifluoromethyl)-4a,5,7,7a-tetrahydro-4H-furo[3,4-d][1,3]oxazin-2-yl)carbamate The compound obtained in Preparation Example 26-(10) (8.12 g, crude) was dissolved in THF (100 mL), di-tert-butyl dicarbonate (6 g) was added and the reaction mixture was heated to 60° C. After stirring for 16 h, the reaction mixture was cooled and sodium bicarbonate (sat., aq., 100 mL) added. The mixture was then extracted with EtOAc (3×150 mL) and the combined organic portions were dried over MgSO$_4$ and evaporated. The residue was purified by silica gel column chromatography (10% to 25% EtOAc in hexanes) to afford the title compound (4.57 g). $^1$H NMR (400 MHz, CDCl$_3$) δ ppm 1.55 (m, 9H), 3.38 (d, J=6.6 Hz, 1H), 3.93 (d, J=8.1 Hz, 1H), 4.06 (d, J=11.1 Hz, 1H), 4.31 (d, J=11.4 Hz, 1H), 4.47-4.66 (m, 2H), 6.74 (br s, 1H), 7.25-7.33 (m, 1H), 8.22-8.31 (m, 1H), 8.57-8.63 (m, 1H)

26-(12) Synthesis of tert-butyl((4aR,5S,7aS)-7a-(5-amino-2-fluorophenyl)-5-(trifluoromethyl)-4a,5,7,7a-tetrahydro-4H-furo[3,4-d][1,3]oxazin-2-yl)carbamate The compound obtained in Preparation Example 26-(11) (4.57 g) was dissolved in ethanol (100 mL) and tin chloride dihydrate (7.0 g) was added. After stirring for 18 h, the solution was poured onto NaOH (2N aq., 200 mL), and the resulting mixture was extracted with EtOAc (2×250 mL). The combined organic portions were dried over MgSO$_4$ and evaporated to afford the title compound (3.16 g). $^1$H NMR (400 MHz, CDCl$_3$) δ ppm 1.48 (s, 9H), 3.36 (q, J=7.2 Hz, 1H), 3.70 (br s, 2H), 3.97 (dd, J=9.1, 3.3 Hz, 1H), 4.18-4.41 (m, 3H), 4.71 (dd, J=11.7, 6.9 Hz, 1H), 6.54 (dt, J=8.6, 3.4 Hz, 1H), 6.84 (dd, J=12.0, 8.7 Hz, 1H), 6.95 (dd, J=6.8, 2.8 Hz, 1H), 7.06 (s, 1H)

Preparation Example 27

Synthesis of 5-ethoxypyrazine-2-carboxylic acid (27-(2)

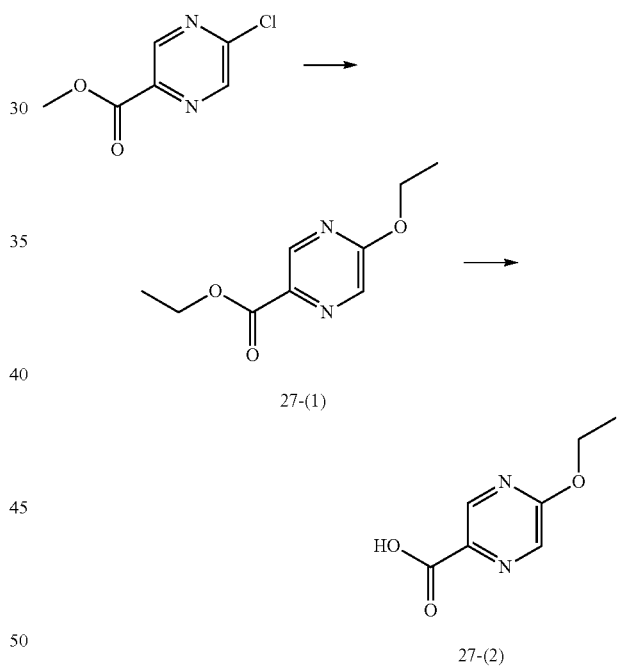

Synthesis of ethyl 5-ethoxypyrazine-2-carboxylate 27-(1)

A stirred solution of methyl 5-chloropyrazine-2-carboxylate (0.50 g) in ethanol (10 mL) was cooled to 0° C., and sodium ethoxide (21% w/w solution in ethanol, 1 mL) was added over 10 mins. After allowing to warm to RT and stir for 2 h, water (100 mL) was added and the mixture extracted with EtOAc (2×150 mL). The combined organic portions were dried over MgSO$_4$ and evaporated to afford the title compound. (0.65 g, purity approx. 85%) $^1$H NMR (400 MHz, CDCl$_3$) δ ppm 1.45 (t, J=7.1 Hz, 3H), 1.46 (t, J=7.1 Hz, 3H), 4.48 (q, J=7.1 Hz, 2H), 4.49 (q, J=7.1 Hz, 2H), 8.28 (d, J=1.3 Hz, 1H), 8.88 (d, J=1.3 Hz, 1H)

Synthesis of 5-ethoxypyrazine-2-carboxylic acid 27-(2)

Ethyl 5-ethoxypyrazine-2-carboxylate (0.65 g, approx. purity 85%) was dissolved in dioxan (3 mL) and water (3 mL) was added, followed by lithium hydroxide monohydrate (255 mg, portionwise over 10 mins). After stirring at RT for 24 h, diethyl ether (25 mL) and NaHCO$_3$ (sat., aq., 25 mL) were added. The layers were separated and the organic layer was extracted with NaOH (1 N, aq., 25 mL). The combined aqueous portions were acidified with 6N HCl to pH 2, and the mixture extracted with EtOAc (3×40 mL). The combined EtOAc extracts were dried over MgSO$_4$ and evaporated to afford the title compound as an off-white powder. $^1$H NMR (400 MHz, CDCl$_3$) δ ppm 1.47 (t, J=7.1 Hz, 3H), 4.53 (q, J=7.1 Hz, 2H), 8.16 (d, J=1.2 Hz, 1H), 8.98 (d, J=1.2 Hz, 1H)

Preparation Example 28

Synthesis of 5-ethoxypyrazine-2-carboxylic acid (28-(3)

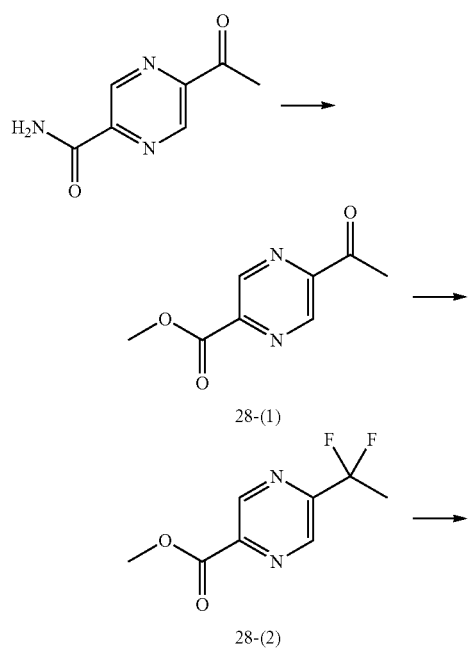

28-(1)

28-(2)

28-(3)

Methyl 5-acetylpyrazine-2-carboxylate 28-(1)

5-Acetylpyrazine-2-carboxamide (3.275 g) was dissolved in methanolic HCl (1.25 N, 150 mL) and the reaction mixture was heated to reflux and stirred overnight. After cooling, sodium bicarbonate was added and the mixture was extracted with EtOAc.

The EtOAc layer was dried over MgSO$_4$ and evaporated to afford the title compound (3.79 g, approx purity 90%). $^1$H NMR (400 MHz, CDCl$_3$) δ ppm 2.78 (s, 3H), 4.10 (s, 3H), 9.33 (d, J=1.5 Hz, 1H), 9.36 (d, J=1.5 Hz, 1H)

Methyl 5-(1,1-difluoroethyl)pyrazine-2-carboxylate 28-(2)

Methyl 5-acetylpyrazine-2-carboxylate (300 mg, approx purity 90%) was dissolved in DCM (15 mL) and cooled to 0° C. under nitrogen. Bis(2-methoxyethyl)aminosulfur trifluoride (0.61 mL) was added dropwise and the reaction mixture allowed to warm to RT and stir overnight. Sodium bicarbonate (sat., aq.) was added cautiously and the mixture extracted with DCM. The organic portions were dried over MgSO$_4$, evaporated and purified by silica gel chromatography (35% EtOAc in hexane) to afford the title compound (155 mg) as a white solid. $^1$H NMR (400 MHz, CDCl$_3$) δ ppm 2.00 (t, J=18.8 Hz, 3H), 4.01 (s, 3H), 8.98 (d, J=1.5 Hz, 1H), 9.24 (d, J=1.5 Hz, 1H)

5-(1,1-Difluoroethyl)pyrazine-2-carboxylic acid 28-(3)

Methyl 5-(1,1-difluoroethyl)pyrazine-2-carboxylate (0.65 g, approx. purity 85%) was dissolved in dioxan (2 mL) and water (2 mL) was added, followed by lithium hydroxide monohydrate (54 mg, portionwise). After stirring at RT for 90 mins, the mixture was concentrated to 2 mL and diethyl ether (20 mL) added. The mixture was then extracted with NaOH (1 N, aq., 20 mL), and the aqueous portions acidified with 6N HCl to pH 2. The aqueous portion was then extracted with EtOAc, dried over MgSO$_4$ and evaporated to afford the title compound as a white solid (119 mg). $^1$H NMR (400 MHz, CDCl$_3$) δ ppm 2.11 (t, J=18.8 Hz, 3H), 9.01 (d, J=1.3 Hz, 1H), 9.47 (d, J=1.3 Hz, 1H)

Preparation Example 29

Synthesis of 5-(fluoromethyl)pyrazine-2-carboxylic acid (29-(3)

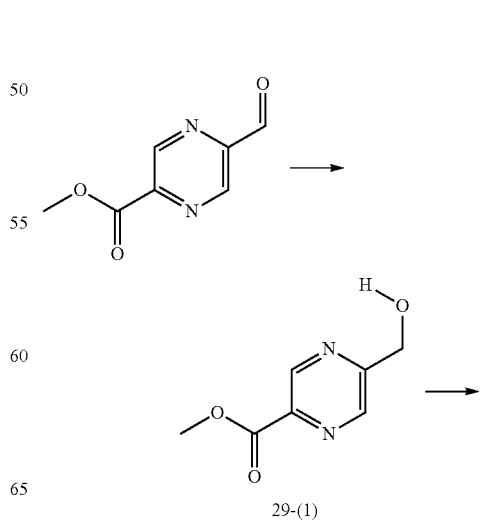

29-(1)

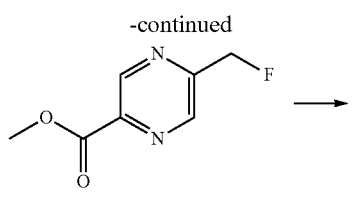

29-(2)

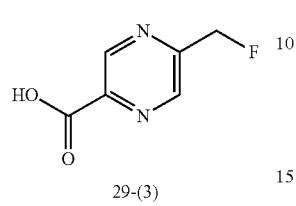

29-(3)

Methyl 5-(hydroxymethyl)pyrazine-2-carboxylate 29-(1)

To a solution of methyl 5-formylpyrazine-2-carboxylate (2.47 g) in THF (20 mL) was added sodium borohydride (170 mg) portionwise over 10 mins. After stirring for 1 h, methanol (10 mL) was added. The reaction mixture was stirred for a further 20 mins, and then HCl (1 N, aq., 20 mL) and brine (20 mL) were added. The mixture was extracted with EtOAc (3×40 mL) and the combined organic portions dried over MgSO$_4$ and evaporated to afford the title compound (1.31 g). $^1$H NMR (400 MHz, CDCl$_3$) δ ppm 4.07 (s, 3H), 4.98 (br. s., 2H), 8.80 (s, 1H), 9.27 (s, 1H)

Methyl 5-(fluoromethyl)pyrazine-2-carboxylate 29-(2)

To a solution of methyl 5-(hydroxymethyl)pyrazine-2-carboxylate (0.64 g) in THF (20 mL) was added triethylamine (2.30 g) and the solution was cooled to 0° C. Triethylamine trihydrofluoride (1.22 g) was then added followed by nonafluorobutanesulfonyl fluoride (2.28 g) dropwise over 5 mins. After warming to RT and stirring for 2 h, NaHCO$_3$ (sat., aq., 100 mL) was added, and the mixture was extracted with EtOAc (2×50 mL). The combined organic portions were dried over MgSO$_4$, evaporated, and purified by silica gel chromatography (5% to 50% EtOAc in hexane) to afford the title compound (94 mg). $^1$H NMR (400 MHz, CDCl$_3$) δ ppm 4.07 (s, 3H), 5.67 (d, J=46.5 Hz, 2H), 8.89 (s, 1H), 9.28 (s, 1H)

5-(Fluoromethyl)pyrazine-2-carboxylic acid 29-(3)

Methyl 5-(fluoromethyl)pyrazine-2-carboxylate (94 mg) was dissolved in dioxan (1 mL) and water (1 mL) was added, followed by lithium hydroxide monohydrate (60 mg). After stirring at RT for 18 h, diethyl ether (20 mL) was added and the mixture was then extracted with NaOH (1 N, aq., 2×20 mL). The aqueous portions were acidified with 6N HCl to pH 1, extracted with EtOAc (2×40 mL), the combined organic portions dried over MgSO$_4$ and evaporated to afford the title compound as a white solid (71 mg).

$^1$H NMR (400 MHz, CDCl$_3$) δ ppm 5.70 (d, J=46.2 Hz, 2H), 8.85 (s, 1H), 9.40 (s, 1H)

General Procedure A: the Coupling of Anilines Prepared in Preparation Examples 25-(14) and 26-(12) with Aryl Carboxylic Acids The aniline (100 mg) was dissolved in DCM (2 mL) and the aryl carboxylic acid (1.2-1.6 equiv.), N,N-diisopropylethylamine (3 equiv.) and (1H-benzotriazol-1-yloxy)tripyrrolidin-1-yl)phosphonium hexafluorophophate (1.2-1.6 equiv.) were added. The reaction mixture was stirred at RT for 16 h-3 days, and sodium bicarbonate (sat., aq., 25 mL) was added. The mixture was extracted with EtOAc (2×40 mL), the combined organic portions were dried over MgSO$_4$, evaporated and purified by silica gel chromatography (EtOAc/hexanes gradient) to afford the amide as a white solid. The amide was dissolved in DCM (2 mL) and TFA (1 mL) was added. After stirring at RT for 1-3 h, the reaction mixture was evaporated and sodium bicarbonate (sat., aq., 25 mL) was added. The mixture was extracted with EtOAc (2×40 mL), and the combined organic portions dried over MgSO$_4$ and evaporated to afford the desired compound as a white solid. On occasions where the product was not pure, purification was effected by silica gel chromatography (MeOH/EtOAc/DCM gradients).

Example 1

N-(3-(((4aR,5S,7aS)-2-amino-5-(fluoromethyl)-4a,5,7,7a-tetrahydro-4H-furo[3,4-d][1,3]oxazin-7a-yl)-4-fluorophenyl)-5-(difluoromethyl)pyrazine-2

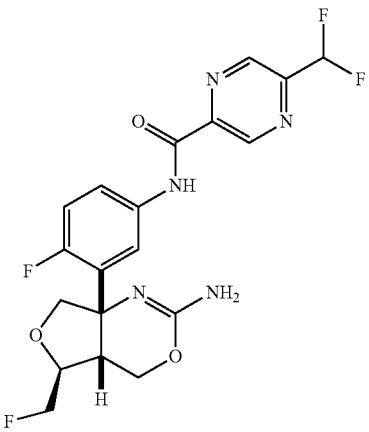

Chiral

Synthesized from tert-butyl[(4aR,5S,7aS)-7a-(5-amino-2-fluorophenyl)-5-fluoromethyl-4a,5,7,7a-tetrahydro-4H-furo[3,4-d][1,3]oxazin-2-yl]carbamate 25-(14) and 5-difluoromethyl-pyrazine-2-carboxylic acid according to General Procedure A.

$^1$H NMR (400 MHz, CDCl$_3$) δ (ppm): 2.94 (d, J=7.8 Hz, 1H), 3.79 (dd, J=8.6, 2.5 Hz, 1H), 3.89-4.05 (m, 2H), 4.28-4.66 (m, 4H), 6.72 (t, J=54.3 Hz, 1H), 7.05 (dd, J=11.6, 8.8 Hz, 1H), 7.67 (dd, J=7.1, 2.8 Hz, 1H), 7.91-8.03 (m, 1H), 8.85 (s, 1H), 9.45 (s, 1H), 9.61 (br s, 1H)

Example 2

N-(3-((4aR,5S,7aS)-2-amino-5-(fluoromethyl)-4a,5,7,7a-tetrahydro-4H-furo[3,4-d][1,3]oxazin-7a-yl)-4-fluorophenyl)-5-cyanopicolinamide

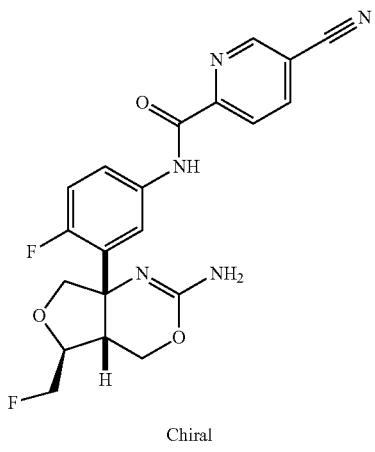

Chiral

Synthesized from tert-butyl[(4aR,5S,7aS)-7a-(5-amino-2-fluorophenyl)-5-fluoromethyl-4a,5,7,7a-tetrahydro-4H-furo[3,4-d][1,3]oxazin-2-yl]carbamate 25-(14) and 5-cyanopyridine-2-carboxylic acid according to General Procedure A.

$^1$H NMR (400 MHz, CDCl$_3$) δ (ppm): 2.93 (dt, J=7.8, 2.0 Hz, 1H), 3.79 (dd, J=8.5, 2.7 Hz, 1H), 3.90-4.02 (m, 2H), 4.28-4.77 (m, 6H), 7.04 (dd, J=11.6, 8.8 Hz, 1H), 7.67 (dd, J=7.1, 2.8 Hz, 1H), 7.91-8.01 (m, 1H), 8.14 (dd, J=8.3, 2.0 Hz, 1H), 8.35 (dd, J=8.2, 0.9 Hz, 1H), 8.82 (dd, J=1.9, 0.9 Hz, 1H), 9.82 (br s, 1H)

Example 3

N-(3-((4aR,5S,7aS)-2-amino-5-(trifluoromethyl)-4a,5,7,7a-tetrahydro-4H-furo[3,4-d][1,3]oxazin-7a-yl)-4-fluorophenyl)-5-cyanopicolinamide

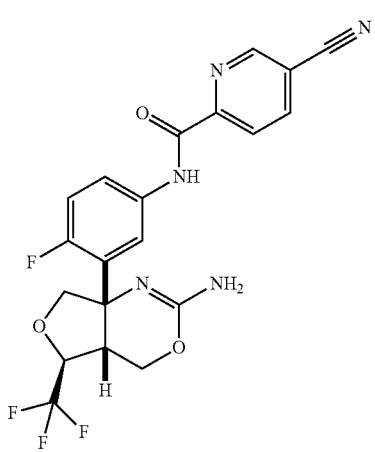

Chiral

Synthesized from tert-butyl[(4aR,5S,7aS)-7a-(5-amino-2-fluorophenyl)-5-trifluoromethyl-4a,5,7,7a-tetrahydro-4H-furo[3,4-d][1,3]oxazin-2-yl]carbamate 26-(12) and 5-cyanopyridine-2-carboxylic acid according to General Procedure A.

$^1$H NMR (400 MHz, CDCl$_3$) δ (ppm): 3.27 (d, J=7.6 Hz, 1H), 3.83 (d, J=8.1 Hz, 1H), 3.90-3.98 (m, 1H), 4.00-4.11 (m, 1H), 4.11-4.85 (m, 4H), 7.06 (dd, J=11.4, 9.1 Hz, 1H), 7.71 (dd, J=6.6, 2.5 Hz, 1H), 7.87-8.00 (m, 1H), 8.14 (ddd, J=8.1, 2.0, 1.0 Hz, 1H), 8.36 (d, J=8.1 Hz, 1H), 8.79-8.88 (m, 1H), 9.82 (br s, 1H)

Example 4

N-(3-((4aR,5S,7aS)-2-amino-5-(trifluoromethyl)-4a,5,7,7a-tetrahydro-4H-furo[3,4-d][1,3]oxazin-7a-yl)-4-fluorophenyl)-5-(difluoromethyl)pyrazine-2

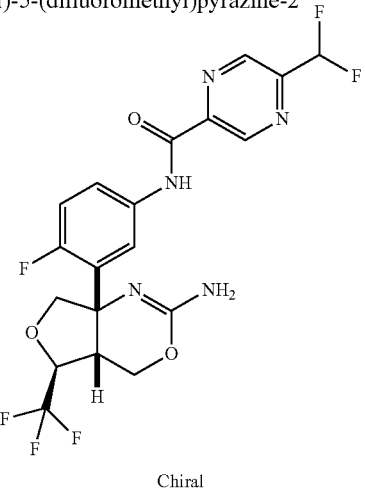

Chiral

Synthesized from tert-butyl[(4aR,5S,7aS)-7a-(5-amino-2-fluorophenyl)-5-trifluoromethyl-4a,5,7,7a-tetrahydro-4H-furo[3,4-d][1,3]oxazin-2-yl]carbamate 26-(12) and 5-difluoromethyl-pyrazine-2-carboxylic acid according to General Procedure A.

$^1$H NMR (400 MHz, CD$_3$OD) δ (ppm): 3.39 (d, J=7.8 Hz, 1H), 3.88 (dd, J=8.3, 2.5 Hz, 1H), 4.00-4.15 (m, 1H), 4.15-4.27 (m, 1H), 4.42-4.66 (m, 2H), 6.97 (t, J 54.6, 1H), 7.21 (dd, J=11.9, 8.8 Hz, 1H), 7.93 (ddd, J=8.8, 4.2, 2.9 Hz, 1H), 8.02 (dd, J=7.3, 2.8 Hz, 1H), 9.05 (s, 1H), 9.42 (s, 1H)

Example 5

N-(3-((4aR,5S,7aS)-2-amino-5-(fluoromethyl)-4a,5,7,7a-tetrahydro-4H-furo[3,4-d][1,3]oxazin-7a-yl)-4-fluorophenyl)-5-methoxypyrazine-2-carboxamide

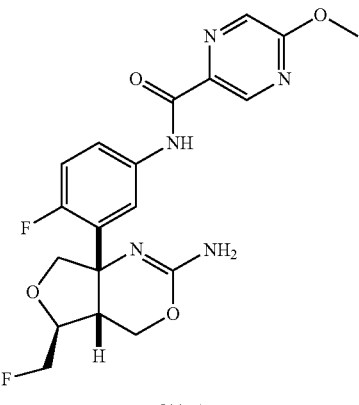

Chiral

Synthesized from tert-butyl[(4aR,5S,7aS)-7a-(5-amino-2-fluorophenyl)-5-fluoromethyl-4a,5,7,7a-tetrahydro-4H-furo[3,4-d][1,3]oxazin-2-yl]carbamate 25-(14) and 5-methoxy-pyrazine-2-carboxylic acid according to General Procedure A.

¹H NMR (400 MHz, CDCl₃) δ (ppm): 3.03 (d, J=7.8 Hz, 1H), 3.90 (dd, J=9.0, 2.4 Hz, 1H), 3.93-4.14 (m, 5H), 4.29-4.41 (m, 2H), 4.43-4.53 (m, 1H), 4.54-4.67 (m, 1H), 7.03 (dd, J=11.6, 8.8 Hz, 1H), 7.62 (dd, J=7.1, 2.8 Hz, 1H), 7.88-7.98 (m, 1H), 8.09 (d, J=1.3 Hz, 1H), 8.93 (d, J=1.3 Hz, 1H), 9.51 (s, 1H)

Example 6

N-(3-((4aR,5S,7aS)-2-amino-5-(trifluoromethyl)-4a,5,7,7a-tetrahydro-4H-furo[3,4-d][1,3]oxazin-7a-yl)-4-fluorophenyl)-5-methoxypyrazine-2-carboxamide

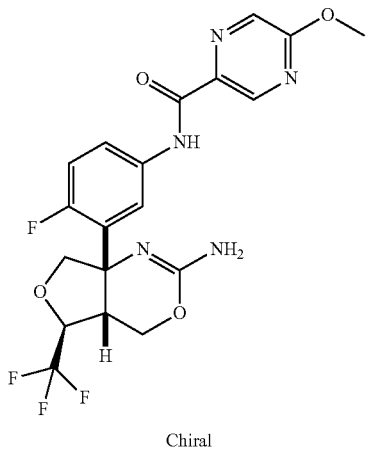

Chiral

Synthesized from tert-butyl[(4aR,5S,7aS)-7a-(5-amino-2-fluorophenyl)-5-trifluoromethyl-4a,5,7,7a-tetrahydro-4H-furo[3,4-d][1,3]oxazin-2-yl]carbamate 26-(12) and 5-methoxypyrazine-2-carboxylic acid according to General Procedure A.

¹H NMR (400 MHz, CDCl₃) δ (ppm): 3.25 (d, J=7.6 Hz, 1H), 3.81 (dd, J=8.1, 2.3 Hz, 1H), 3.90-4.07 (m, 5H), 4.22 (br s, 2H), 4.37-4.52 (m, 2H), 7.03 (dd, J=11.6, 8.8 Hz, 1H), 7.67 (dd, J=7.1, 2.8 Hz, 1H), 7.93 (ddd, J=8.8, 4.2, 2.9 Hz, 1H), 8.05-8.11 (m, 1H), 8.94 (d, J=1.5 Hz, 1H), 9.47 (s, 1H)

Example 7

N-(3-((4aR,5S,7aS)-2-amino-5-(trifluoromethyl)-4a,5,7,7a-tetrahydro-4H-furo[3,4-d][1,3]oxazin-7a-yl)-4-fluorophenyl)-5-methylpyrazine-2-carboxamide

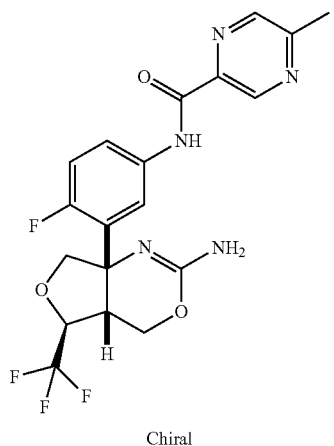

Chiral

Synthesized from tert-butyl[(4aR,5S,7aS)-7a-(5-amino-2-fluorophenyl)-5-trifluoromethyl-4a,5,7,7a-tetrahydro-4H-furo[3,4-d][1,3]oxazin-2-yl]carbamate 26-(12) and 5-methylpyrazine-2-carboxylic acid according to General Procedure A.

¹H NMR (400 MHz, CDCl₃) δ (ppm): 2.71 (s, 3H), 3.44 (d, J=7.3 Hz, 1H), 4.05 (d, J=8.6 Hz, 1H), 4.13-4.29 (m, 2H), 4.47-4.65 (m, 2H), 7.15 (dd, J=11.6, 8.8 Hz, 1H), 7.77 (dd, J=6.9, 2.7 Hz, 1H), 7.98-8.08 (m, 1H), 8.42-8.49 (m, 1H), 9.36 (d, J=1.3 Hz, 1H), 9.72 (s, 1H)

Example 8

N-(3-((4aR,5S,7aS)-2-amino-5-(trifluoromethyl)-4a,5,7,7a-tetrahydro-4H-furo[3,4-d][1,3]oxazin-7a-yl)-4-fluorophenyl)-5-(trifluoromethyl)picolinamide

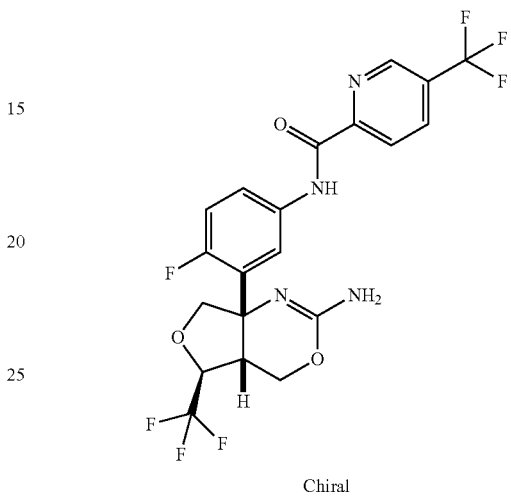

Chiral

Synthesized from tert-butyl[(4aR,5S,7aS)-7a-(5-amino-2-fluorophenyl)-5-trifluoromethyl-4a,5,7,7a-tetrahydro-4H-furo[3,4-d][1,3]oxazin-2-yl]carbamate 26-(12) and 5-(trifluoromethyl)picolinic acid according to General Procedure A.

¹H NMR (400 MHz, CDCl₃) δ (ppm): 3.25 (d, J=7.8 Hz, 1H), 3.81 (dd, J=8.2, 2.1 Hz, 1H), 3.89-3.98 (m, 1H), 3.98-4.10 (m, 1H), 4.17 (br s, 2H), 4.36-4.53 (m, 2H), 7.05 (dd, J=11.6, 8.8 Hz, 1H), 7.72 (dd, J=7.1, 2.8 Hz, 1H), 7.91-8.01 (m, 1H), 8.10 (dd, J=8.1, 2.0 Hz, 1H), 8.36 (d, J=8.1 Hz, 1H), 8.75-8.87 (m, 1H), 9.89 (s, 1H)

Example 9

N-(3-((4aR,5S,7aS)-2-amino-5-(trifluoromethyl)-4a,5,7,7a-tetrahydro-4H-furo[3,4-d][1,3]oxazin-7a-yl)-4-fluorophenyl)-5-(fluoromethyl)pyrazine-2-carboxamide

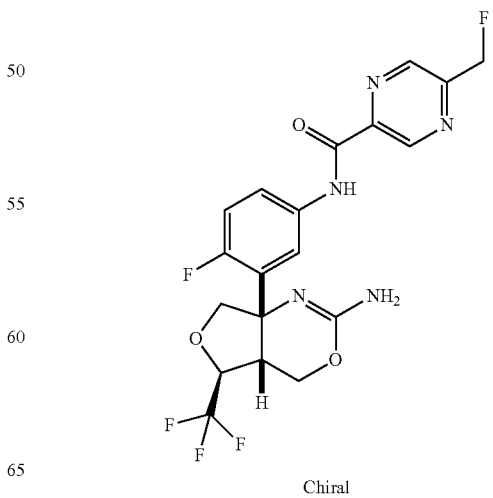

Chiral

Synthesized from tert-butyl[(4aR,5S,7aS)-7a-(5-amino-2-fluorophenyl)-5-trifluoromethyl-4a,5,7,7a-tetrahydro-4H-furo[3,4-d][1,3]oxazin-2-yl]carbamate 26-(12) and 5-fluoromethyl-pyrazine-2-carboxylic acid according to General Procedure A.

¹H NMR (400 MHz, CDCl₃) δ (ppm): 3.33 (d, J=7.6 Hz, 1H), 3.89 (d, J=8.1 Hz, 1H), 4.02 (dd, J=11.6, 1.8 Hz, 1H), 4.06-4.16 (m, 1H), 4.36 (br s, 2H), 4.46-4.61 (m, 2H), 5.67 (d, J=46.5 Hz, 2H), 7.13 (dd, J=11.4, 8.8 Hz, 1H), 7.83 (dd, J=7.1, 2.8 Hz, 1H), 8.00 (dt, J=8.7, 3.5 Hz, 1H), 8.74 (s, 1H), 9.43 (s, 1H), 9.71 (s, 1H)

Example 10

N-(3-((4aR,5S,7aS)-2-amino-5-(trifluoromethyl)-4a,5,7,7a-tetrahydro-4H-furo[3,4-d][1,3]oxazin-7a-yl)-4-fluorophenyl)-5-methylpicolinamide

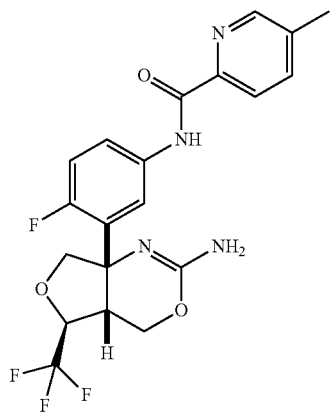

Chiral

Synthesized from tert-butyl[(4aR,5S,7aS)-7a-(5-amino-2-fluorophenyl)-5-trifluoromethyl-4a,5,7,7a-tetrahydro-4H-furo[3,4-d][1,3]oxazin-2-yl]carbamate 26-(12) and 5-methyl picolinic acid according to General Procedure A.

¹H NMR (400 MHz, CD₃OD) δ (ppm): 2.47 (s, 3H), 3.62 (d, J=7.1 Hz, 1H), 4.13 (d, J=10.1 Hz, 1H), 4.43-4.59 (m, 2H), 4.63 (d, J=9.6 Hz, 1H), 4.66-4.76 (m, 1H), 7.29 (dd, J=11.9, 8.8 Hz, 1H), 7.81-7.93 (m, 2H), 8.07-8.20 (m, 2H), 8.57 (d, J=2.0 Hz, 1H)

Example 11

N-(3-((4aR,5S,7aS)-2-amino-5-(trifluoromethyl)-4a,5,7,7a-tetrahydro-4H-furo[3,4-d][1,3]oxazin-7a-yl)-4-fluorophenyl)-5-ethylpicolinamide

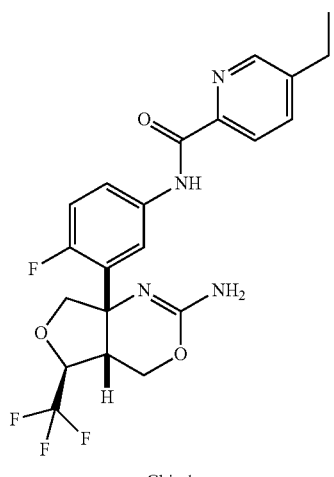

Chiral

Synthesized from tert-butyl[(4aR,5S,7aS)-7a-(5-amino-2-fluorophenyl)-5-trifluoromethyl-4a,5,7,7a-tetrahydro-4H-furo[3,4-d][1,3]oxazin-2-yl]carbamate 26-(12) and 5-ethyl picolinic acid according to General Procedure A.

¹H NMR (400 MHz, CDCl₃) δ (ppm): 1.32 (t, J=7.6 Hz, 3H), 2.77 (q, J=7.6 Hz, 2H), 3.40 (d, J=7.6 Hz, 1H), 4.03 (d, J=8.6 Hz, 1H), 4.07-4.25 (m, 2H), 4.44-4.62 (m, 2H), 7.13 (dd, J=11.6, 8.8 Hz, 1H), 7.70-7.81 (m, 2H), 8.04 (ddd, J=8.8, 4.1, 3.0 Hz, 1H), 8.20 (d, J=7.8 Hz, 1H), 8.39-8.50 (m, 1H), 10.06 (s, 1H)

Example 12

N-(3-((4aR,5S,7aS)-2-amino-5-(trifluoromethyl)-4a,5,7,7a-tetrahydro-4H-furo[3,4-d][1,3]oxazin-7a-yl)-4-fluorophenyl)-5-ethoxypyrazine-2-carboxamide

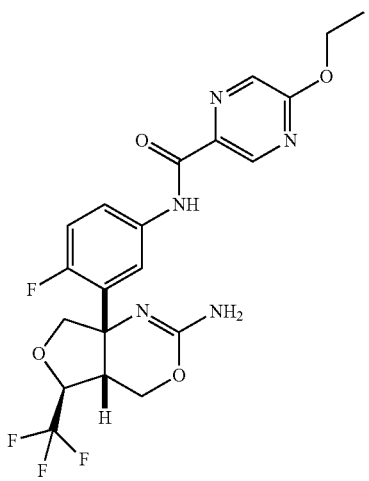

Chiral

Synthesized from tert-butyl[(4aR,5S,7aS)-7a-(5-amino-2-fluorophenyl)-5-trifluoromethyl-4a,5,7,7a-tetrahydro-4H-furo[3,4-d][1,3]oxazin-2-yl]carbamate 26-(12) and 5-methoxypyrazine-2-carboxylic acid according to General Procedure A.

¹H NMR (400 MHz, CDCl₃) δ (ppm): 1.46 (t, J=7.1 Hz, 3H), 3.47 (d, J=7.3 Hz, 1H), 4.07-4.15 (m, 1H), 4.21 (d, J=12.1 Hz, 1H), 4.30 (d, J=11.4 Hz, 1H), 4.45-4.62 (m, 4H), 7.14 (dd, J=11.7, 9.0 Hz, 1H), 7.75 (dd, J=6.9, 2.7 Hz, 1H), 7.96-8.06 (m, 1H), 8.14 (d, J=1.3 Hz, 1H), 8.99 (d, J=1.3 Hz, 1H), 9.60 (s, 1H)

Example 13

N-(3-((4aR,5S,7aS)-2-amino-5-(trifluoromethyl)-4a,5,7,7a-tetrahydro-4H-furo[3,4-d][1,3]oxazin-7a-yl)-4-fluorophenyl)-5-(1,1-difluoroethyl)pyrazine-2-carboxamide

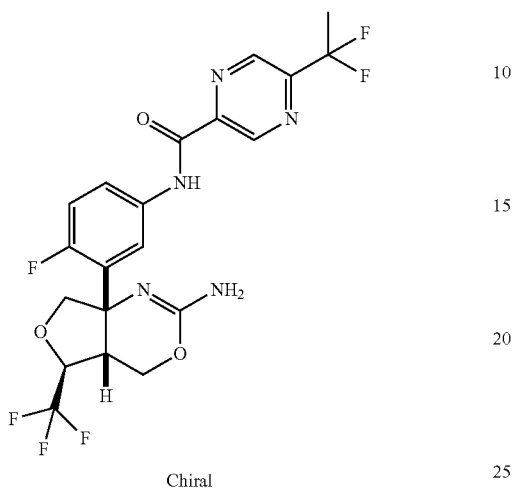

Chiral

Synthesized from tert-butyl[(4aR,5S,7aS)-7a-(5-amino-2-fluorophenyl)-5-trifluoromethyl-4a,5,7,7a-tetrahydro-4H-furo[3,4-d][1,3]oxazin-2-yl]carbamate 26-(12) and 5-(1,1-difluoroethyl)pyrazine-2-carboxylic acid according to General Procedure A.

$^1$H NMR (600 MHz, CDCl$_3$) δ (ppm): 2.13 (t, J=18.8 Hz, 3H), 3.35 (d, J=7.5 Hz, 1H), 3.90 (d, J=8.3 Hz, 1H), 4.03 (dd, J=11.7, 1.9 Hz, 1H), 4.10-4.16 (m, 1H), 4.24 (br s, 2H), 4.53 (quin, J=7.2 Hz, 1H), 4.58 (d, J=8.3 Hz, 1H), 7.16 (dd, J=11.5, 8.8 Hz, 1H), 7.81 (dd, J=6.8, 2.6 Hz, 1H), 8.06 (dt, J=8.8, 3.5 Hz, 1H), 8.92-8.99 (m, 1H), 9.53 (s, 1H), 9.71 (s, 1H)

Preparation Example 30

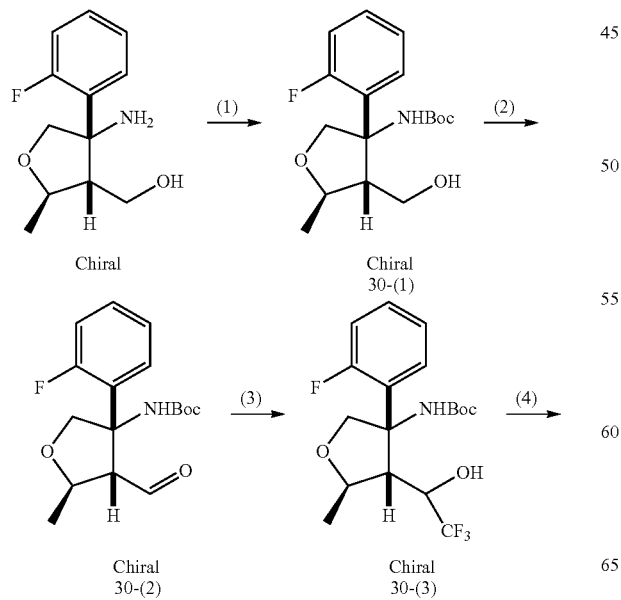

-continued

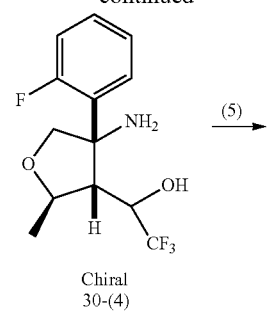
Chiral
30-(4)

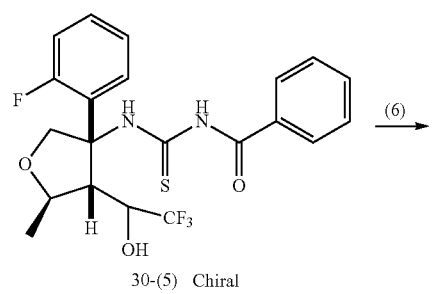
30-(5) Chiral

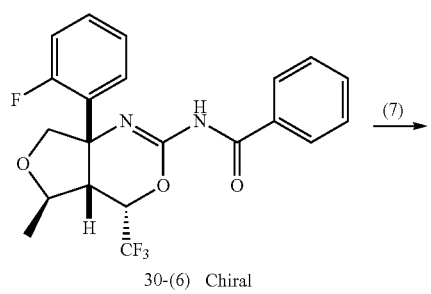
30-(6) Chiral

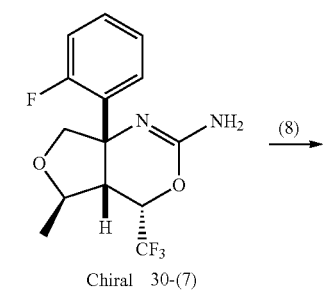
Chiral 30-(7)

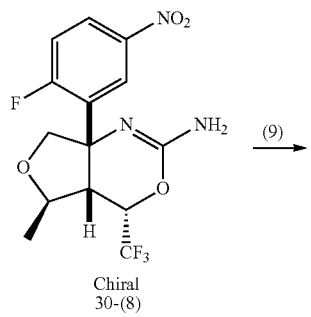
Chiral 30-(8)

-continued

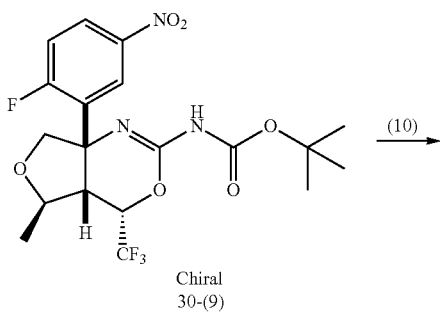

Chiral 30-(9)

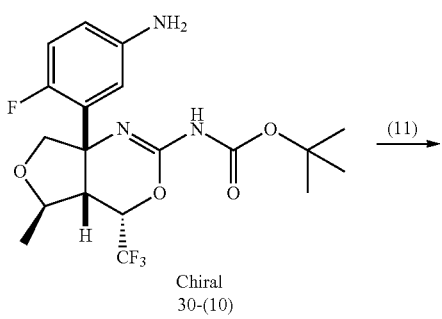

Chiral 30-(10)

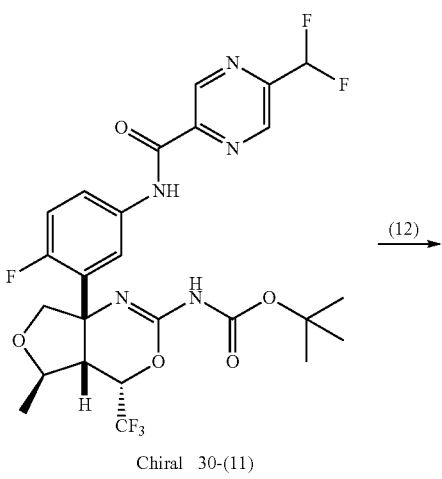

Chiral 30-(11)

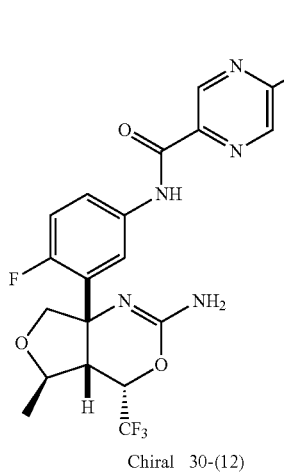

Chiral 30-(12)

30-(1) Synthesis of [(3S,4R,5R)-3-(2-Fluoro-phenyl)-4-hydroxymethyl-5-methyl-tetrahydro-furan-3-yl]-carbamic acid tert-butylester

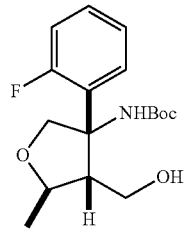

[(2R,3R,4S)-4-Amino-4-(2-fluoro-phenyl)-2-methyl-tetrahydro-furan-3-yl]-methanol (2.5 g, 11.10 mmol) was dissolved in THF. N,N-diethylethanamine (1.34 g, 13.31 mmol) was added to the reaction mixture, followed by di-tert-butyl dicarbonate (2.66 g, 12.20 mmol). The reaction was stirred at RT. The reaction was followed by TLC (Rf 0.60 in Hexane/EtOAc 50%). After 18 h, sat. aq. NaHCO$_3$ (100 ml) was added, then extracted with EtOAc (2×100 ml), dried over MgSO$_4$ and concentrated. The mixture was then purified by flash chromatography (hexane/EtOAc 0-40%). 2.70 g (75% yield) of the title compound was isolated.

30-(2) Synthesis of [(3S,4S,5R)-3-(2-Fluoro-phenyl)-4-formyl-5-methyl-tetrahydro-furan-3-yl]-carbamic acid tert-butyl ester

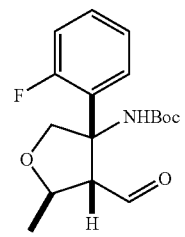

[(3S,4R,5R)-3-(2-Fluoro-phenyl)-4-hydroxymethyl-5-methyl-tetrahydro-furan-3-yl]-carbamic acid tert-butylester (Preparation Example 30-(1)) (1.2 g, 3.60 mmol) dissolved in DCM (26.5 g, 20 mL). 1,1,1-tris(acetyloxy)-,2-benziodoxol-3(1H)-one (3.12 g, 7.3 mmol) was added. The reaction mixture was stirred at RT. The reaction was followed by TLC Hexane/EtOAc 40%. Product Rf was 0.52. The reaction reached completion after 2 h. Work up: 20 ml of sat. aq. NaHCO$_3$ and 20 ml of saturated sodium bisulfite was added. The mixture was then extracted with ether 3×50 ml. The combined organic phases were dried on MgSO$_4$, concentrated and purified by flash chromatography Hexane/EtOAc (5-30%). 900 mg of the title compound was isolated (76% yield).

30-(3) Synthesis of [(3S,4R,5R)-3-(2-Fluoro-phenyl)-5-methyl-4-(2,2,2-trifluoro-1-hydroxy-ethyl)-tetrahydro-furan-3-yl]-carbamic acid tert-butyl ester

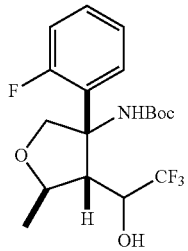

[(3S,4S,5R)-3-(2-Fluoro-phenyl)-4-formyl-5-methyl-tetrahydro-furan-3-yl]-carbamic acid tert-butyl ester (Preparation Example 30-(2)) (2.00 g, 0.62 mmol) dissolved in THF (20 mL). Trimethyl(trifluoromethyl) silane (175.89 mg, 1.23 mmol) was added followed by TBAF (0.080 g, 0.30 mmol). The reaction mixture was stirred at RT and monitored by LCMS (Agilent Method A), retention time 5.61 min (MH+ 294). The reaction went to completion after 2 h. The reaction was then concentrated, saturated aqueous ammonium chloride (10 ml) was added and extracted with DCM (2×20 ml). The combined organic phases were combined, dried over $MgSO_4$ concentrated and purified by flash chromatography (Hexane/EtOAc 5-40%). 1.20 g (49% yield) of the title compound was isolated as a mixture of the 2 epimers (85/15).

30-(4) Synthesis of 1-[(2R,3R,4S)-4-Amino-4-(2-fluoro-phenyl)-2-methyl-tetrahydro-furan-3-yl]-2,2,2-trifluoro-ethanol

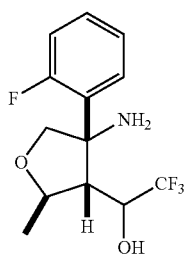

[(3S,4R,5R)-3-(2-Fluoro-phenyl)-5-methyl-4-(2,2,2-trifluoro-1-hydroxy-ethyl)-tetrahydro-furan-3-yl]-carbamic acid tert-butyl ester (Preparation Example 30-(3)) (1.20 g, 0.23 mmol) was dissolved in DCM (20 ml). TFA (10 ml) was added. The reaction mixture was stirred overnight (16 h). The reaction was then concentrated, 10 ml of aqueous saturated sodium carbonate was added then extracted with DCM (2×40 ml). 900 mg (86%) of a mixture of the title compound (85%) and its epimer at the $CF_3$ position (15%) were isolated.

30-(5) Synthesis of 1-Benzoyl-3-[(3S,4R,5R)-3-(2-fluoro-phenyl)-5-methyl-4-(2,2,2-trifluoro-1-hydroxy-ethyl)-tetrahydro-furan-3-yl]-thiourea

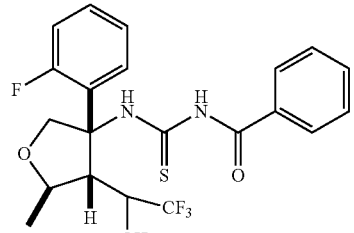

1-[(2R,3R,4S)-4-Amino-4-(2-fluoro-phenyl)-2-methyl-tetrahydro-furan-3-yl]-2,2,2-trifluoro-ethanol (Preparation Example 30-(4)) (550 mg, 1.87 mmol) was dissolved in DCM (15 mL) was transferred into the reaction vessel. Solution was cooled to 0° C. Benzoyl isothiocyanate (1.22 g, 7.50 mmol) was added drop-wise over 20 mins as a solution in DCM (100 mL). Reaction mixture was allowed to warm up to RT and stir overnight. TLC in neat EtOAc showed the weak SM spot was gone from Rf 0.10. Product was at Rf 0.40. (EtOAc:Hex 4:6), product was concentrated. Saturated aqueous sodium bicarbonate (30 ml) was added and then extracted with DCM (3×40 ml). The combined organic phases were combined and purified via flash chromatography (Hexane/EtoAc 0-50%). 0.75 g (87% yield) title compound (85%) and its epimer at the $CF_3$ position (15%) were isolated as a brown solid. $^1$H NMR (400 MHz, $CDCl_3$) ppm 1.36 (d, J=6.06 Hz, 3H) 2.66 (d, J=7.33 Hz, 1H) 4.53-4.59 (m, 1H) 4.59-4.69 (m, 2H) 4.89 (d, J=9.73 Hz, 1H) 7.05 (ddd, J=12.54, 8.18, 1.14 Hz, 1H) 7.12-7.17 (m, 1H) 7.28-7.32 (m, 1H) 7.43 (td, J=8.12, 1.58 Hz, 1H) 7.46-7.51 (m, 2H) 7.58-7.64 (m, 1H) 7.79-7.84 (m, 2H) 9.20 (s, 1H) 11.73 (s, 1H)

30-(6) Synthesis of N-[(4S,4aS,5R,7aS)-7a-(2-fluorophenyl)-5-methyl-4-(trifluoromethyl)-4a,5,7,7a-tetrahydro-4H-furo[3,4-d][1,3]oxazin-2-yl]benzamide

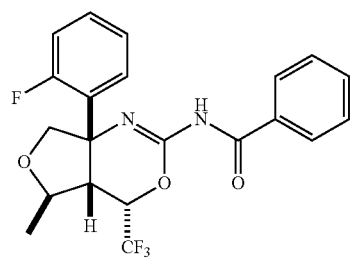

1-Benzoyl-3-[(3S,4R,5R)-3-(2-fluoro-phenyl)-5-methyl-4-(2,2,2-trifluoro-1-hydroxy-ethyl)-tetrahydro-furan-3-yl]- thiourea (Preparation Example 30-(5)) (300 mg, 0.65 mmol) was dissolved in pyridine (1.39 g, 17.61 mmol). The reaction mixture was cooled to 0° C. Triflic anhydride (250 mg, 0.88 mmol) was added drop wise over 30 min, keeping temperature below 10° C. After 1 h, the reaction was concentrated then HCl 1M (50 ml) was added followed by extraction with DCM (2×50 ml). The organic phase was dried on MgSO$_4$ and concentrated. The resulting mixture was purified by flash chromatography (Hexane/EtOAc 10-50%). 278 mg (93% yield) of the title compound (85%) and its isomer (15%) were isolated as a mixture.

30-(7) Synthesis of (4S,4aS,5R,7aS)-7a-(2-fluorophenyl)-5-methyl-4-(trifluoromethyl)-4-a,5,7,7atetrahydro-4H-furo[3,4-d][1,3]oxazin-2-amine

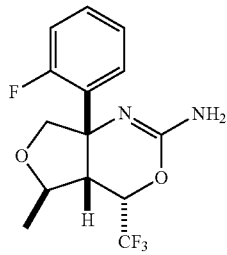

N-[(4S,4aS,5R,7aS)-7a-(2-fluorophenyl)-5-methyl-4-(trifluoromethyl)-4a,5,7,7a-tetrahydro-4H-furo[3,4-d][1,3]oxazin-2-yl]benzamide (Preparation Example 30-(6)) (300 mg, 0.71 mmol) was dissolved in methanol (5 mL). 2,3,4,6,7,8,9,10-octahydropyrimido[1,2-a]azepine (0.22 g, 1.45 mmol) was added. The reaction mixture was heated to reflux. After 13 h, the reaction showed full conversion: LCMS (Agilent Method A) retention time 3.38 min, ES$^+$: 319 [MH]$^+$. The reaction was concentrated and purified by flash chromatography (Hexane/EtOAc 20-100%). 226 mg (99%) of the title compound (85%) and its isomer (15%) were isolated as a mixture.

30-(8) Synthesis of (4S,4aS,5R,7aS)-7a-(2-fluoro-5-nitrophenyl)-5-methyl-4-(trifluoromethyl)-4a,5,7,7a-tetrahydro-4H-furo[3,4-d][1,3]oxazin-2-amine

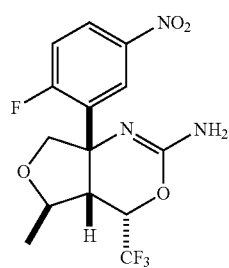

(4S,4aS,5R,7aS)-7a-(2-fluorophenyl)-5-methyl-4-(trifluoromethyl)-4a,5,7,7a-tetrahydro-4H-furo[3,4-d][1,3]oxazin-2-amine (Preparation Example 30-(7)) (226 mg, 0.71 mmol) was dissolved in nitric acid (4.80 g, 76.20 mmol). The reaction was then stirred at RT for 90 min. LCMS (Agilent Method A) retention time 3.25 min, ES$^+$: 364 [MH]$^+$. The reaction was concentrated and purified by flash chromatography (Hexane/EtOAc 20-100%). 218 mg (84% yield) of the title compound (85%) and its isomer (15%) were isolated as a mixture.

30-(9) Synthesis of tert-butyl[(4S,4aS,5R,7aS)-7a-(2-fluoro-5-nitrophenyl)-5-methyl-4-(trifluoromethyl)-4a,5,7,7a-tetrahydro-4H-furo[3,4-d][1,3]oxazin-2-yl)carbamate

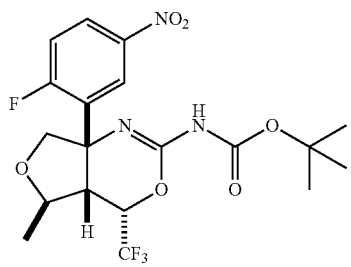

(4S,4aS,5R,7aS)-7a-(2-fluoro-5-nitrophenyl)-5-methyl-4-(trifluoromethyl)-4a,5,7,7a-tetrahydro-4H-furo[3,4-d][1,3]oxazin-2-amine (Preparation Example 30-(8)) (218 mg, 0.60 mmol) was dissolved in THF (5 mL). The reaction mixture was cooled to 0° C. N,N-diethylethanamine (0.19 g, 1.92 mmol) was injected. Di-tert-butyl dicarbonate (235.63 mg, 1.08 mmol) was transferred portion wise over 20 min into the reaction vessel. The reaction mixture was allowed to warm to RT and stir overnight. LCMS (Agilent Method A) retention time 6.53 min, ES$^+$: 464 [MH]$^+$. The reaction was concentrated and purified by flash chromatography (Hexane/EtOAc 20-100%) 255 mg (89%) of the title compound (85%) and its isomer (15%) were isolated as a mixture.

30-(10) synthesis of tert-butyl((4S,4aS,5R,7aS)-7a-(5-amino-2-fluorophenyl)-5-methyl-4-(trifluoromethyl)-4a,5,7,7a-tetrahydro-4H-furo[3,4-d][1,3]oxazin-2-yl)carbamate

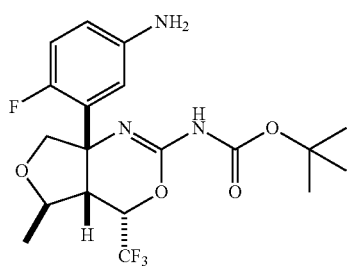

Tert-butyl[(4S,4aS,5R,7aS)-7a-(2-fluoro-5-nitrophenyl)-5-methyl-4-(trifluoromethyl)-4-a,5,7,7atetrahydro-4H-furo

[3,4-d][1,3]oxazin-2-yl]carbamate (Preparation Example 30-(9)) (231.88 mg, 0.50 mmol) was dissolved in ethanol (20 ml). The solution was reduced via H-cube® (ThalesNano), using a 10% Pd/C catalyst, at RT, full-$H_2$. 217 mg (100%) of the title compound (85%) and its isomer (15%) were isolated as a mixture.

30-(11) synthesis of ((1S,4aS,5R,7aS)-7a-{5-[(5-Difluoromethyl-pyrazine-2-carbonyl)-amino]-2-fluoro-phenyl}-5-methyl-4-trifluoromethyl-4a,5,7,7a-tetrahydro-4H-furo[3,4-d][1,3]oxazin-2-yl)-carbamic acid tert-butyl ester

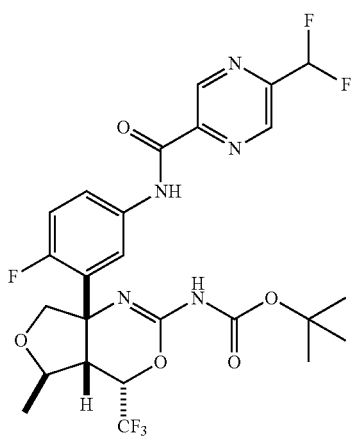

tert-butyl((4S,4aS,5R,7aS)-7a-(5-amino-2-fluorophenyl)-5-methyl-4-(trifluoromethyl)-4-a,5,7,7a-tetrahydro-4H-furo[3,4-d][1,3]oxazin-2-yl)carbamate (Preparation Example 30-(10)) (110.25 mg, 0.25 mmol) dissolved in DCM. 5-(difluoromethyl)pyrazine-2-carboxylic acid (66.43 mg, 0.38 mmol) added. Followed by N-ethyl-N-(propan-2-yl)propan-2-amine (65.75 mg, 0.51 mmol) and N-[(dimethylamino)(3H-[1,2,3]triazolo[4,5-b]pyridin-3-yloxy)methylidene]-N-methylmethanaminium hexafluorophosphate (0.14 g, 0.38 mmol). The reaction was stirred at RT. LCMS (Agilent Method A) Retention time 5.44 min, $ES^+$: 535 $[MH]^+$. After 15 min, the reaction mixture was washed with HCl 1M (2×5 mL) then washed with sat. $NaHCO_3$ (2×5 mL). The organic phase was then concentrated and the crude mixture was purified by flash chromatography. 140 mg (100%) of the title compound (85%) and its isomer (15%) were isolated as a mixture. $^1H$ NMR (400 MHz, $CDCl_3$) ppm 1.45 (d, J=6.19 Hz, 3H) 1.55 (s, 9H) 2.95 (dd, J=8.84, 2.65 Hz, 1H) 3.89 (dd, J=8.84, 2.53 Hz, 1H) 4.30 (qd, J=6.91, 2.27 Hz, 1H) 4.48 (quin, J=6.44 Hz, 1H) 4.56 (dd, J=(dd, J=11.68, 9.03 Hz, 1H) 6.82 (t, J=54.20 Hz, 1H) 7.22 (dd, J=11.6, 7.87 Hz, 1H) 7.55 (dd, J=6.88, 2.84 Hz, 1H) 8.26 (ddd, J=8.87, 4.14, 2.78 Hz, 1H) 8.97 (s, 1H) 9.55 (s, 1H) 9.70 (s, 1H)

30-(12) Synthesis of 5-Difluoromethyl-pyrazine-2-carboxylic acid [3-((1S,4aS,5R,7aS)-2-amino-5-methyl-4-trifluoromethyl-4a,5-dihydro-4H-furo[3,4-d][1,3]oxazin-7a-yl)-4-fluoro-phenyl]-amide (Example 14)

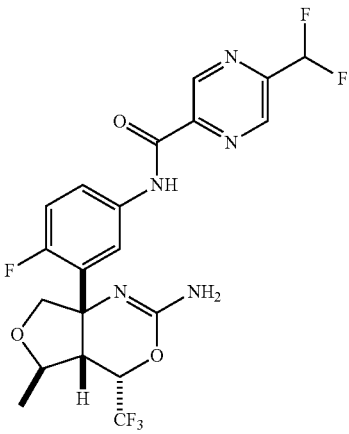

((1S,4aS,5R,7aS)-7a-{5-[(5-Difluoromethyl-pyrazine-2-carbonyl)-amino]-2-fluoro-phenyl}-5-methyl-4-trifluoromethyl-4a,5,7,7a-tetrahydro-4H-furo[3,4-d][1,3]oxazin-2-yl)-carbamic acid tert-butyl ester (Preparation Example 30-(11)) (140.23 mg, 0.24 mmol) dissolved in DCM was transferred into the reaction vessel. TFA was added to the reaction mixture. The reaction mixture was stirred overnight (16 h). The reaction was then concentrated, 10 ml of aqueous sodium carbonate was added then extracted with DCM (2×20 ml) to give 90 mg (87%) of a mixture of the desired compound (85%) and its epimer at the $CF_3$ position (15%). The mixture was further purified by preparative HPLC (Gilson). 30 mg of the desired compound title compound was isolated. 28 mg of the mixed epimers was isolated. $^1H$ NMR (400 MHz, $CDCl_3$) ppm 1.45 (d, J=6.19 Hz, 3H) 2.95 (d, J=6.44 Hz, 1H) 3.78 (d, J=8.46 Hz, 1H) 4.30 (s, 1H) 4.44 (d, J=8.72 Hz, 1H) 4.54 (t, J=6.19 Hz, 1H) 6.82 (t, J=54.2 Hz, 1H) 7.14 (d, J=0.51 Hz, 1H) 7.63-7.73 (m, 1H) 8.05 (d, J=8.72 Hz, 1H) 8.98 (s, 1H) 9.54 (s, 1H) 9.69 (s, 1H)

Test Example 1

Quantification of Aβ Peptide in Culture of Neurons from Rat Fetus Brain (1) Rat Primary Neuronal Culture Primary neuronal cultures were prepared from the cerebral cortex of embryonic day 18 Wistar rats (Charles River Japan, Yokohama, Japan). Specifically, the embryos were aseptically removed from pregnant rats under ether anesthesia. The brain was isolated from the embryo and immersed in an ice-cold L-15 medium (such as Invitrogen Corp. Cat #11415-064, Carlsbad, Calif., USA, or SIGMA L1518). The cerebral cortex was collected from the isolated brain under a stereoscopic microscope. The cerebral cortex fragments collected were enzymatically treated in an enzyme solution containing 0.25% trypsin (Invitrogen Corp. Cat #15050-065, Carlsbad, Calif., USA) and 0.01% DNase (Sigma D5025, St. Louis, Mo., USA) at 37° C. for 30 minutes to disperse the cells. Here, the enzymatic reaction was stopped by adding inactivated horse serum to the solution. The enzymatically treated solution was centrifuged at 1,500 rpm for five minutes to remove the supernatant. 5 to 10 mL of a medium was added to the resulting cell mass. Neurobasal medium (Invitrogen Corp. Cat #21103-049, Carlsbad, Calif., USA) supplemented with 2% B27 supplement (Invitrogen Corp. Cat #17504-044, Carlsbad, Calif., USA), 25 µM 2-mercaptoethanol (2-ME, WAKO Cat #139-06861, Osaka, Japan), 0.5 mM L-glutamine (Invitrogen Corp. Cat #25030-081, Carlsbad, Calif., USA), and Antibiotics-Antimycotics (Invitrogen Corp. Cat #15240-062, Carlsbad, Calif., USA) was used as the medium (Neurobasal/B27/2-ME). However, the above Neurobasal medium not supplemented with 2-ME (Neurobasal/B27) was used for the assay. The cells were redispersed by mild pipetting of the cell mass to which the medium was added. The cell dispersion was filtered through a 40-µm nylon mesh (Cell Strainer, Cat #35-2340, Becton Dickinson Labware, Franklin Lakes, N.J., USA) to remove the remaining cell mass, and thus a neuronal cell suspension was obtained. The neuronal cell suspension was diluted with the medium and then plated in a volume of 100 µL/well at an initial cell density of $5 \times 10^5$ cells/cm$^2$ in a 96-well polystyrene culture plate pre-coated with poly-L or D-lysine (Falcon Cat #35-3075, Becton Dickinson Labware, Franklin Lakes, N.J., USA coated with poly-L-lysine using the method shown below, or BIOCOAT™ cell environments Poly-D-lysine cell ware 96-well plate, Cat #35-6461, Becton Dickinson Labware, Franklin Lakes, N.J., USA). Poly-L-lysine coating was carried out as follows. 100 µg/mL of a poly-L-lysine (SIGMA P2636, St. Louis, Mo., USA) solution was aseptically prepared with a 0.15 M borate buffer (pH 8.5). 100 µg/well of the solution was added to the 96-well polystyrene culture plate and incubated at room temperature for one or more hours or at 4° C. overnight or longer. Thereafter, the coated 96-well polystyrene culture plate was washed with sterile water four or more times, and then dried or rinsed with, for example, sterile PBS or medium, and used for cell plating. The plated cells were cultured in the culture plate at 37° C. in 5% CO$_2$-95% air for one day. Then, the total amount of the medium was replaced with a fresh Neurobasal™/B27/2-ME medium, and then the cells were cultured for a further three days.

(2) Addition of Compound

The drug was added to the culture plate on Day 4 of culture as follows. The total amount of the medium was removed from the wells, and 180 µL/well of Neurobasal medium not containing 2-ME and containing 2% B-27 (Neurobasal/B27) was added thereto. A solution of the test compound in DMSO was diluted with Neurobasal/B27 to a concentration 10-fold higher than the final concentration. 20 µL/well of the dilution was added to and sufficiently mixed with the medium. The final DMSO concentration was 1% or less. Only DMSO was added to the control group.

(3) Sampling

The cells were cultured for three days after addition of the compound, and the total amount of the medium was collected. The resulting medium was used as an ELISA sample. The sample was not diluted for ELISA measurement of Aβx-42 and diluted to 5-fold with a diluent supplied with an ELISA kit for ELISA measurement of Aβx-40.

(4) Evaluation of Cell Survival

Cell survival was evaluated by an MTT assay according to the following procedure. After collecting the medium, 100 µL/well of a pre-warmed medium was added to the wells. Further, 8 µL/well of a solution of 8 mg/mL of MTT (SIGMA M2128, St. Louis, Mo., USA) in D-PBS(−) (Dulbecco's phosphate buffered Saline, SIGMA D8537, St. Louis, Mo., USA) was added to the wells. The 96-well polystyrene culture plate was incubated in an incubator at 37° C. in 5% CO$_2$-95% air for 20 minutes. 100 µL/well of an MTT lysis buffer was added thereto, and MTT formazan crystals were sufficiently dissolved in the buffer in the incubator at 37° C. in 5% CO$_2$-95% air. Then, the absorbance at 550 nm in each well was measured. The MTT lysis buffer was prepared as follows. 100 g of SDS (sodium dodecyl sulfate, sodium lauryl sulfate), WAKO 191-07145, Osaka, Japan) was dissolved in a mixed solution of 250 mL of N,N-dimethylformamide (WAKO 045-02916, Osaka, Japan) with 250 mL of distilled water. 350 µL each of concentrated hydrochloric acid and acetic acid were further added to the solution to allow the solution to have a final pH of about 4.7.

Upon measurement, wells having no cells plated and containing only the medium and MTT solution were set as background (bkg). The measured values were respectively applied to the following formula including subtracting bkg values from them. Thus, the proportion against the control group (group not treated with the drug, CTRL) (% of CTRL) was calculated to compare and evaluate cell survival activities.

% of CTRL=($A550$_sample–$A550$_$bkg$)/
($A550$_CTRL–$bkg$)×100

(A550_sample: absorbance at 550 nm of sample well, A550_bkg: absorbance at 550 nm of background well, A550_CTRL: absorbance at 550 nm of control group well)

(5) Aβ ELISA

Human/Rat β Amyloid (42) ELISA Kit Wako (#290-62601) and Human/Rat β Amyloid (40) ELISA Kit Wako (#294-62501) from Wako Pure Chemical Industries, Ltd. were used for Aβ ELISA. Aβ ELISA was carried out according to the protocols recommended by the manufacturers, described in the documents accompanying the kits. However, the Aβ calibration curve was created using beta-amyloid peptide 1-42, rat and beta-amyloid peptide 1-40, rat (Calbiochem, #171596 [Aβ$_{42}$], #171593 [Aβ$_{40}$]). The results would be shown as percentage to the Aβ concentration in the medium of the control group (% of CTRL).

The compounds of the present invention have an Aβ42 production reducing effect.

The compound of the general formula (I) or pharmaceutically acceptable salt thereof or solvate thereof according to the present invention has an Aβ42 production reducing effect. Thus, the present invention can particularly provide a prophylactic or therapeutic agent for a neurodegenerative disease caused by Aβ such as Alzheimer-type dementia or Down's syndrome.

As measured by Test Example 1, compound Examples 1 to 14 showed IC$_{50}$ values of less than 1 µM.

The invention claimed is:

1. A compound represented by the formula (I):

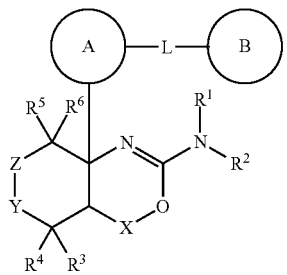

(I)

or a pharmaceutically acceptable salt thereof or a solvate thereof, wherein

Ring A is a $C_{6-14}$ aryl group which optionally has 1 to 3 substituents selected from Substituent Group α, a 5- to 6-membered heteroaryl group which optionally has 1 to 3 substituents selected from Substituent Group α or a 9- to 10-membered benzo-fused heterocyclic group which optionally has 1 to 3 substituents selected from Substituent Group α;

L is a single bond, an oxygen atom, a formula —$NR^eCO$— (wherein $R^e$ is a hydrogen atom or a $C_{1-6}$ alkyl group which optionally has 1 to 3 substituents selected from Substituent Group α), a formula —$NR^eSO_2$— (wherein $R^e$ is a hydrogen atom or a $C_{1-6}$ alkyl group which optionally has 1 to 3 substituents selected from Substituent Group α), a formula —$NR^e$— (wherein $R^e$ is a hydrogen atom or a $C_{1-6}$ alkyl group which optionally has 1 to 3 substituents selected from Substituent Group α), a $C_{1-6}$ alkylene group which optionally has 1 to 3 substituents selected from Substituent Group α, a $C_{2-6}$ alkenylene group which optionally has 1 to 3 substituents selected from Substituent Group α or a $C_{2-6}$ alkynylene group which optionally has 1 to 3 substituents selected from Substituent Group α;

Ring B is a $C_{3-8}$ cycloalkyl group which optionally has 1 to 3 substituents selected from Substituent Group α, a $C_{6-14}$ aryl group which optionally has 1 to 3 substituents selected from Substituent Group α or a 5- to 10-membered heterocyclic group which optionally has 1 to 3 substituents selected from Substituent Group α;

X is a single bond or a $C_{1-3}$ alkylene group which optionally has 1 to 3 substituents selected from Substituent Group α;

Y is a single bond, —$NR^Y$— (wherein $R^Y$ is a hydrogen atom, a $C_{1-6}$ alkyl group which optionally has 1 to 3 substituents selected from Substituent Group α, a $C_{1-6}$ alkylcarbonyl group which optionally has 1 to 3 substituents selected from Substituent Group α, a $C_{6-14}$ arylcarbonyl group which optionally has 1 to 3 substituents selected from Substituent Group α, a $C_{1-6}$ alkylsulfonyl group which optionally has 1 to 3 substituents selected from Substituent Group α, a $C_{6-14}$ arylsulfonyl group which optionally has 1 to 3 substituents selected from Substituent Group α, a $C_{6-14}$ aryl group which optionally has 1 to 3 substituents selected from Substituent Group α or a 5- to 10-membered heterocyclic group which optionally has 1 to 3 substituents selected from Substituent Group α), an oxygen atom, a sulfur atom, a sulfoxide or a sulfone;

Z is a single bond, a $C_{1-3}$ alkylene group which optionally has 1 to 3 substituents selected from Substituent Group α or a $C_{2-3}$ alkenylene group which may have 1 to 3 substituents selected from Substituent Group α;

$R^1$ and $R^2$ are each independently a hydrogen atom, a $C_{1-6}$ alkyl group which optionally has 1 to 3 substituents selected from Substituent Group α, a $C_{1-6}$ alkylcarbonyl group which optionally has 1 to 3 substituents selected from Substituent Group α, a $C_{6-14}$ arylcarbonyl group which optionally has 1 to 3 substituents selected from Substituent Group α, a $C_{1-6}$ alkylsulfonyl group which optionally has 1 to 3 substituents selected from Substituent Group α, a $C_{6-14}$ arylsulfonyl group which optionally has 1 to 3 substituents selected from Substituent Group α, a 3- to 10-membered carbocyclic group which optionally has 1 to 3 substituents selected from Substituent Group α or a 5- to 10-membered heterocyclic group which optionally has 1 to 3 substituents selected from Substituent Group α; and $R^3$, $R^4$, $R^5$ and $R^6$ are independently a hydrogen atom, a halogen atom, a hydroxy group, a $C_{1-6}$ alkyl group which optionally has 1 to 3 substituents selected from Substituent Group α, a $C_{1-6}$ alkoxy group which optionally has 1 to 3 substituents selected from Substituent Group α, a 3- to 10-membered carbocyclic group which optionally has 1 to 3 substituents selected from Substituent Group α or a 5- to 10-membered heterocyclic group which optionally has 1 to 3 substituents selected from Substituent Group α; or $R^4$ and $R^6$ together form a ring represented by the formula (II):

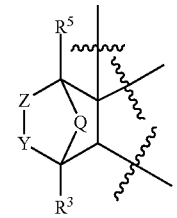

(II)

wherein Y, Z, $R^5$ and $R^3$ are the same as defined above and Q is an oxygen atom, a methylene group or an ethylene group;

wherein Substituent Group α consists of a hydrogen atom, a halogen atom, a hydroxy group, a nitro group, a $C_{1-6}$ alkylthio group, a $C_{6-14}$ aryl group, a $C_{6-14}$ aryloxycarbonyl group, a $C_{6-14}$ arylcarbonyl group, a cyano group, a $C_{3-8}$ cycloalkoxy group, a $C_{3-8}$ cycloalkyl group, a $C_{3-8}$ cycloalkylthio group, a sulfonylamino group (wherein the sulfonylamino group is optionally substituted with a $C_{1-6}$ alkyl group), a $C_{2-6}$ alkenyl group which optionally has 1 to 3 substituents selected from Substituent Group β, a $C_{2-6}$ alkynyl group which optionally has 1 to 3 substituents selected from Substituent Group β, a carbamoyl group which is optionally substituted with one or two $C_{1-6}$ alkyl groups, a $C_{1-6}$ alkoxy group which optionally has 1 to 3 substituents selected from Substituent Group β, a $C_{1-6}$ alkyl group which optionally has 1 to 3 substituents selected from Substituent Group β and a 5- to 10-membered heterocyclic group which optionally has 1 to 3 substituents selected from Substituent Group β; and wherein Substituent Group β consists of a halogen atom, a cyano group, a hydroxy group, a $C_{1-6}$ alkoxy group, a $C_{1-6}$ alkyl group, a $C_{3-8}$ cycloalkyl group and an oxo group].

2. The compound or pharmaceutically acceptable salt thereof or solvate thereof according to claim 1 wherein X is a methylene which optionally has 1 to 2 substituents selected from Substituent Group α.

3. The compound or pharmaceutically acceptable salt thereof or solvate thereof according to claim 1 wherein Y is an oxygen atom.

4. The compound or pharmaceutically acceptable salt thereof or solvate thereof according to claim 1 wherein Z is a single bond.

5. The compound or pharmaceutically acceptable salt thereof or solvate thereof according to claim 1 wherein L is a single bond, a formula —NR$^e$CO— (wherein R$^e$ is a hydrogen atom or a $C_{1-6}$ alkyl group which optionally has 1 to 3 substituents selected from Substituent Group α) or a formula —NR$^e$SO$_2$— (wherein R$^e$ is a hydrogen atom or a $C_{1-6}$ alkyl group which optionally has 1 to 3 substituents selected from Substituent Group α).

6. The compound or pharmaceutically acceptable salt thereof or solvate thereof according to claim 5 wherein L is a formula —NR$^e$CO— (wherein R$^e$ is a hydrogen atom or a $C_{1-6}$ alkyl group which optionally has 1 to 3 substituents selected from Substituent Group α).

7. The compound or pharmaceutically acceptable salt thereof or solvate thereof according to claim 1 wherein Ring A is a $C_{6-14}$ aryl group which optionally has 1 to 3 substituents selected from Substituent Group α.

8. The compound or pharmaceutically acceptable salt thereof or solvate thereof according to claim 1 wherein Ring B is a 5 to 10-membered heterocyclic group which optionally has 1 to 3 substituents selected from Substituent Group α.

9. The compound or pharmaceutically acceptable salt thereof or solvate thereof according to claim 1 wherein the compound is selected from the group consisting of:

N-(3-((4a,5,7a)-2-amino-5-(fluoromethyl)-4a,5,7,7a-tetrahydro-4H-furo[3,4-d][1,3]oxazin-7a-yl)-4-fluorophenyl)-5-(difluoromethyl)pyrazine-2-carboxamide;

N-(3-(2-amino-5-(fluoromethyl)-4a,5,7,7a-tetrahydro-4H-furo[3,4-d][1,3]oxazin-7a-yl)-4-fluorophenyl)-5-methoxypyrazine-2-carboxamide;

N-(3-(2-amino-5-(fluoromethyl)-4a,5,7,7a-tetrahydro-4H-furo[3,4-d][1,3]oxazin-7a-yl)-4-fluorophenyl)-5-(difluoromethoxy)pyrazine-2-carboxamide;

N-(3-(2-amino-5-(fluoromethyl)-4a,5,7,7a-tetrahydro-4H-furo[3,4-d][1,3]oxazin-7a-yl)-4-fluorophenyl)-5-(fluoromethoxy)pyrazine-2-carboxamide;

N-(3-(2-amino-5-(fluoromethyl)-4a,5,7,7a-tetrahydro-4H-furo[3,4-d][1,3]oxazin-7a-yl)-4-fluorophenyl)-5-ethoxypyrazine-2-carboxamide;

N-(3-(2-amino-5-(fluoromethyl)-4a,5,7,7a-tetrahydro-4H-furo[3,4-d][1,3]oxazin-7a-yl)-4-fluorophenyl)-5-fluoropicolinamide;

N-(3-(2-amino-5-(fluoromethyl)-4a,5,7,7a-tetrahydro-4H-furo[3,4-d][1,3]oxazin-7a-yl)-4-fluorophenyl)-5-cyanopicolinamide;

N-(3-(2-amino-5-(fluoromethyl)-4a,5,7,7a-tetrahydro-4H-furo[3,4-d][1,3]oxazin-7a-yl)-4-fluorophenyl)-5-chloropicolinamide;

N-(3-(2-amino-5-(fluoromethyl)-4a,5,7,7a-tetrahydro-4H-furo[3,4-d][1,3]oxazin-7a-yl)-4-fluorophenyl)-5-(trifluoromethyl)picolinamide;

N-(3-(2-amino-5-(fluoromethyl)-4a,5,7,7a-tetrahydro-4H-furo[3,4-d][1,3]oxazin-7a-yl)-4-fluorophenyl)-5-(difluoromethyl)picolinamide;

N-(3-(2-amino-5-(fluoromethyl)-4a,5,7,7a-tetrahydro-4H-furo[3,4-d][1,3]oxazin-7a-yl)-4-fluorophenyl)-5-(fluoromethyl)picolinamide;

N-(3-(2-amino-5-(fluoromethyl)-4a,5,7,7a-tetrahydro-4H-furo[3,4-d][1,3]oxazin-7a-yl)-4-fluorophenyl)-5-methoxypicolinamide;

N-(3-(2-amino-5-(fluoromethyl)-4a,5,7,7a-tetrahydro-4H-furo[3,4-d][1,3]oxazin-7a-yl)-4-fluorophenyl)-5-(difluoromethoxy)picolinamide;

N-(3-((4aR,5S,7aS)-2-amino-5-(trifluoromethyl)-4a,5,7,7a-tetrahydro-4H-furo[3,4-d][1,3]oxazin-7a-yl)-4-fluorophenyl)-5-cyanopicolinamide;

N-(3-((4aR,5S,7aS)-2-amino-5-(trifluoromethyl)-4a,5,7,7a-tetrahydro-4H-furo[3,4-d][1,3]oxazin-7a-yl)-4-fluorophenyl)-5-(difluoromethyl)pyrazine-2-carboxamide;

N-(3-((4aR,5S,7aS)-2-amino-5-(trifluoromethyl)-4a,5,7,7a-tetrahydro-4H-furo[3,4-d][1,3]oxazin-7a-yl)-4-fluorophenyl)-5-methoxypyrazine-2-carboxamide;

N-(3-((4aR,5S,7aS)-2-amino-5-(trifluoromethyl)-4a,5,7,7a-tetrahydro-4H-furo[3,4-d][1,3]oxazin-7a-yl)-4-fluorophenyl)-5-methylpyrazine-2-carboxamide;

N-(3-((4aR,5S,7aS)-2-amino-5-(trifluoromethyl)-4a,5,7,7a-tetrahydro-4H-furo[3,4-d][1,3]oxazin-7a-yl)-4-fluorophenyl)-5-(trifluoromethyl)picolinamide;

N-(3-((4aR,5S,7aS)-2-amino-5-(trifluoromethyl)-4a,5,7,7a-tetrahydro-4H-furo[3,4-d][1,3]oxazin-7a-yl)-4-fluorophenyl)-5-(fluoromethyl)pyrazine-2-carboxamide;

N-(3-((4aR,5S,7aS)-2-amino-5-(trifluoromethyl)-4a,5,7,7a-tetrahydro-4H-furo[3,4-d][1,3]oxazin-7a-yl)-4-fluorophenyl)-5-methylpicolinamide;

N-(3-((4aR,5S,7aS)-2-amino-5-(trifluoromethyl)-4a,5,7,7a-tetrahydro-4H-furo[3,4-d][1,3]oxazin-7a-yl)-4-fluorophenyl)-5-ethylpicolinamide;

N-(3-((4aR,5S,7aS)-2-amino-5-(trifluoromethyl)-4a,5,7,7a-tetrahydro-4H-furo[3,4-d][1,3]oxazin-7a-yl)-4-fluorophenyl)-5-ethoxypyrazine-2-carboxamide;

N-(3-((4aR,5S,7aS)-2-amino-5-(trifluoromethyl)-4a,5,7,7a-tetrahydro-4H-furo[3,4-d][1,3]oxazin-7a-yl)-4-fluorophenyl)-5-(1,1-difluoroethyl)pyrazine-2-carboxamide; and 5-Difluoromethyl-pyrazine-2-carboxylic acid [3-((1S,4aS,5R,7aS)-2-amino-5-methyl-4-trifluoromethyl-4a,5-dihydro-4H-furo[3,4-d][1,3]oxazin-7a-yl)-4-fluoro-phenyl]-amide.

10. The compound or pharmaceutically acceptable salt thereof or solvate thereof according to claim 1 wherein the compound has the following stereochemistry:

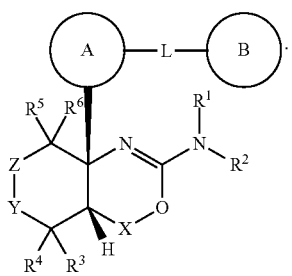

11. A pharmaceutical composition comprising the compound or pharmaceutically acceptable salt thereof or solvate thereof according to claim 1 as an active ingredient.

12. A method of treating Down's syndrome, comprising administering to a human subject suffering from Down's syndrome an effective amount of the compound according to claim 1 or pharmaceutically acceptable salt thereof or solvate thereof.

13. A method of treating Alzheimer-type dementia, comprising administering to a human subject suffering from Alzheimer-type dementia an effective amount of the compound according to claim 1 or pharmaceutically acceptable salt thereof or solvate thereof.

14. A pharmaceutical composition comprising the compound or pharmaceutically acceptable salt thereof or solvate thereof according to claim 9 as an active ingredient.

15. A method of treating Down's syndrome, comprising administering to a human subject suffering from Down's syndrome an effective amount of the compound according to claim 9 or pharmaceutically acceptable salt thereof or solvate thereof.

16. A method of treating Alzheimer-type dementia, comprising administering to a human subject suffering from Alzheimer-type dementia an effective amount of the compound according to claim 9 or pharmaceutically acceptable salt thereof or solvate thereof.

17. A compound which is N-(3-((4aR,5S,7aS)-2-amino-5-(trifluoromethyl)-4a,5,7,7a-tetrahydro-4H-furo[3,4-d][1,3]oxazin-7a-yl)-4-fluorophenyl)-5-cyanopicolinamide or a pharmaceutically acceptable salt thereof or a solvate thereof.

18. A compound which is N-(3-((4aR,5S,7aS)-2-amino-5-(trifluoromethyl)-4a,5,7,7a-tetrahydro-4H-furo[3,4-d][1,3]oxazin-7a-yl)-4-fluorophenyl)-5-(fluoromethyl)pyrazine-2-carboxamide or a pharmaceutically acceptable salt thereof or a solvate thereof.

19. A pharmaceutical composition comprising the compound or pharmaceutically acceptable salt thereof or solvate thereof according to claim 17 as an active ingredient.

20. A method of treating Down's syndrome, comprising administering to a human subject suffering from Down's syndrome an effective amount of the compound or pharmaceutically acceptable salt thereof or solvate thereof according to claim 17.

21. A method of treating Alzheimer-type dementia, comprising administering to a human subject suffering from Alzheimer-type dementia an effective amount of the compound or pharmaceutically acceptable salt thereof or solvate thereof according to claim 17.

22. A pharmaceutical composition comprising the compound or pharmaceutically acceptable salt thereof or solvate thereof according to claim 18 as an active ingredient.

23. A method of treating Down's syndrome, comprising administering to a human subject suffering from Down's syndrome an effective amount of the compound or pharmaceutically acceptable salt thereof or solvate thereof according to claim 18.

24. A method of treating Alzheimer-type dementia, comprising administering to a human subject suffering from Alzheimer-type dementia an effective amount of the compound or pharmaceutically acceptable salt thereof or solvate thereof according to claim 18.

25. A compound which is N-(3-((4aR,5S,7aS)-2-amino-5-(trifluoromethyl)-4a,5,7,7a-tetrahydro-4H-furo[3,4-d][1,3]oxazin-7a-yl)-4-fluorophenyl)-5-methoxypyrazine-2-carboxamide or a pharmaceutically acceptable salt thereof or a solvate thereof.

26. A pharmaceutical composition comprising the compound or pharmaceutically acceptable salt thereof or solvate thereof according to claim 25 as an active ingredient.

27. A method of treating Down's syndrome, comprising administering to a human subject suffering from Down's syndrome an effective amount of the compound or pharmaceutically acceptable salt thereof or solvate thereof according to claim 25.

28. A method of treating Alzheimer-type dementia, comprising administering to a human subject suffering from Alzheimer-type dementia an effective amount of the compound or pharmaceutically acceptable salt thereof or solvate thereof according to claim 25.

* * * * *

UNITED STATES PATENT AND TRADEMARK OFFICE
CERTIFICATE OF CORRECTION

PATENT NO. : 9,079,914 B2  
APPLICATION NO. : 13/386092  
DATED : July 14, 2015  
INVENTOR(S) : John Mark Ellard, Christopher Neil Farthing and Adrian Hall Page 1 of 1

It is certified that error appears in the above-identified patent and that said Letters Patent is hereby corrected as shown below:

In the claims

Column 116, Claim 1

Line 52, delete "Group a" and insert -- Group α --.

Signed and Sealed this
Ninth Day of February, 2016

Michelle K. Lee
*Director of the United States Patent and Trademark Office*